(12) United States Patent
Dube et al.

(10) Patent No.: US 7,238,706 B2
(45) Date of Patent: Jul. 3, 2007

(54) 4-OXO-1-(3-SUBSTITUTED PHENYL-1,4-DIHYDRO-1,8-NAPHTHYRIDINE -3-CARBOXAMIDE PHOSPHODIESTERASE-4 INHIBITORS

(75) Inventors: Daniel Dube, St. Lazare (CA); Laurence Dube, Pierrefonds (CA); Michel Gallant, Montreal (CA); Patrick Lacombe, Montreal (CA); Renee Aspiotis, Montreal (CA); Yves Girard, Ile Bizard (CA); Dwight Macdonald, Lle Bizard (CA)

(73) Assignee: Merck Frosst Canada, Ltd., Kirkland, Quebec (CA)

( * ) Notice: Subject to any disclaimer, the term of this patent is extended or adjusted under 35 U.S.C. 154(b) by 286 days.

(21) Appl. No.: 10/764,229

(22) Filed: Jan. 23, 2004

(65) Prior Publication Data
US 2005/0107402 A1    May 19, 2005

Related U.S. Application Data

(63) Continuation of application No. PCT/CA03/01800, filed on Nov. 19, 2003.

(60) Provisional application No. 60/428,611, filed on Nov. 22, 2002.

(51) Int. Cl.
   A01N 43/42    (2006.01)
   A61K 31/44    (2006.01)
   C07D 471/02   (2006.01)

(52) U.S. Cl. ................ 514/300; 546/123
(58) Field of Classification Search ........... 546/123; 514/300
See application file for complete search history.

(56) References Cited

U.S. PATENT DOCUMENTS

| | | | |
|---|---|---|---|
| 4,284,629 A | | 8/1981 | Grohe et al. |
| 5,321,029 A * | | 6/1994 | Maschler et al. ...... 514/263.36 |
| 5,631,256 A | | 5/1997 | Demuth, Jr. et al. |
| 5,753,666 A | | 5/1998 | Beasley et al. |
| 5,817,670 A | | 10/1998 | Takayama et al. |
| 6,306,869 B1 * | | 10/2001 | Flockerzi ................ 514/287 |
| 6,677,351 B2 * | | 1/2004 | Li et al. ................. 514/300 |
| 2006/0058316 A1 * | | 3/2006 | Dube et al. .............. 514/256 |

FOREIGN PATENT DOCUMENTS

| WO | WO 99/07704 | | 2/1999 |
|---|---|---|---|
| WO | WO 02/09823 | * | 11/2002 |
| WO | WO 02/094823 | | 11/2002 |

OTHER PUBLICATIONS

Houslay, et al., "Phosphodiesterase-4 as a therapeutic target", Drug Discovery Today, 10 (22), Nov. 2005, pp. 1503-1519.*
Meijsing, et al., "Effects of the phosphodiestease-IV inhibitor EMD 95832/3 on tumour growth . . . ", Cancer Letters, 188 (2002), pp. 53-58.*
Ochi, et al., "Necessity of intracellular cyclic AMP in inducing gastric acid secretion . . . ", Life Sciences, 77 (205), pp. 2040-2050.*
Kayanoki, et al., "The effect of cilostazol, a cyclic nucleotide phosphodiesterase III inhibitor . . . ", Biochemical and Biophysical research communications, vol. 238, issue 2, Sep. 18, 1997, abstract.*
Vlachopoulos, et al., "Type 5 phosphodiesterase inhibition by sildenafil . . . ", American journal of hypertension, vol. 17, issue 11, Nov. 2004, abstract.*
Compton, et al., "Cilomilast, a Selective Phosphodiesterase-4 Inhibitor for Treatment of Patients with Chronic Obstructive Pulmonary disease: A Randomised, Dose-Ranging Study", The Lancet, vol. 358, pp. 265-270, 2001.
Rabe, et al., "Roflumilast-An Oral Anti-Inflammatory Treatment For Chronic Obstructive Pulmonary Disease: A Randomised Controlled Trial", The Lancet, vol. 366, pp. 563-571, 2005.
Rose, et al., "Phosphodiesterase Inhibitors for Cognitive Enhancement", Current Pharmaceutical Design, vol. 11, pp. 3329-3334, 2005.

* cited by examiner

Primary Examiner—Margaret D. Seaman
Assistant Examiner—Niloofar Rahmani
(74) Attorney, Agent, or Firm—Sylvia A. Ayler; William Krovatin

(57) ABSTRACT

Compounds represented by Formula (I):

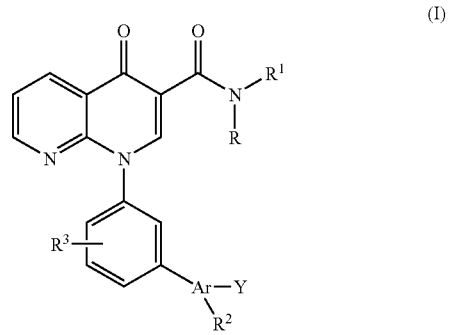

or a pharmaceutically acceptable salt thereof, are phosphodiesterase 4 inhibitors useful in the treatment of asthma and inflammation and useful for the enhancement of cognition.

15 Claims, No Drawings

4-OXO-1-(3-SUBSTITUTED PHENYL-1,4-DIHYDRO-1,8-NAPHTHYRIDINE-3-CARBOXAMIDE PHOSPHODIESTERASE-4 INHIBITORS

CROSS-REFERENCE TO RELATED APPLICATIONS

This application is a Continuation of PCT/CA03/01800, filed Nov. 19, 2003, and also claims priority from U.S. Provisional application 60/428,611, filed Nov. 22, 2002.

BACKGROUND OF THE INVENTION

1. Field of the Invention

The present invention is directed to 4-oxo-1-(3-substituted phenyl-1,4-dihydro-1,8-naphthyridine-3-carboxamide compounds, which are useful as inhibitors of Phosphodiesterase-4.

2. Related Background

Hormones are compounds that variously affect cellular activity. In many respects, hormones act as messengers to trigger specific cellular responses and activities. Many effects produced by hormones, however, are not caused by the singular effect of just the hormone. Instead, the hormone first binds to a receptor, thereby triggering the release of a second compound that goes on to affect the cellular activity. In this scenario, the hormone is known as the first messenger while the second compound is called the second messenger. Cyclic adenosine monophosphate (adenosine 3',5'-cyclic monophosphate, "cAMP" or "cyclic AMP") is known as a second messenger for hormones including epinephrine, glucagon, calcitonin, corticotrophin, lipotropin, luteinizing hormone, norepinephrine, parathyroid hormone, thyroid-stimulating hormone, and vasopressin. Thus, cAMP mediates cellular responses to hormones. Cyclic AMP also mediates cellular responses to various neurotransmitters.

Phosphodiesterases ("PDE") are a family of enzymes that metabolize 3', 5' cyclic nucleotides to 5' nucleoside monophosphates, thereby terminating cAMP second messenger activity. A particular phosphodiesterase, phosphodiesterase-4 ("PDE4", also known as "PDE-IV"), which is a high affinity, cAMP specific, type IV PDE, has generated interest as potential targets for the development of novel anti-asthmatic and anti-inflammatory compounds. PDE4 is known to exist as at lease four isoenzymes, each of which is encoded by a distinct gene. Each of the four known PDE4 gene products is believed to play varying roles in allergic and/or inflammatory responses. Thus, it is believed that inhibition of PDE4, particularly the specific PDE4 isoforms that produce detrimental responses, can beneficially affect allergy and inflammation symptoms. It would be desirable to provide novel compounds and compositions that inhibit PDE4 activity.

A major concern with the use of PDE4 inhibitors is the side effect of emesis which has been observed for several candidate compounds as described in C. Burnouf et al., ("Burnouf"), Ann. Rep. In Med. Chem., 33:91–109(1998). B. Hughes et al., Br. J. Pharmacol., 118:1183–1191(1996); M. J. Perry et al., Cell Biochem. Biophys., 29: 113–132(1998); S. B. Christensen et al., J. Med. Chem., 41:821–835(1998); and Burnouf describe the wide variation of the severity of the undesirable side effects exhibited by various compounds. As described in M. D. Houslay et al., Adv. In Pharmacol., 44:225–342(1998) and D. Spina et al., Adv. In Pharmacol., 44:33–89(1998), there is great interest and research of therapeutic PDE4 inhibitors.

International Patent Publication WO9422852 describes quinolines as PDE4 inhibitors. International Patent Publication WO9907704 describes 1-aryl-1,8-naphthylidin-4-one derivatives as PDE4 inhibitors.

A. H. Cook, et al., J. Chem. Soc., 413–417(1943) describes gamma-pyridylquinolines. Other quinoline compounds are described in Kei Manabe et al., J. Org. Chem., 58(24):6692–6700(1993); Kei Manabe et al., J. Am. Chem. Soc., 115(12):5324–5325(1993); and Kei Manabe et al., J. Am. Chem. Soc., 114(17):6940–6941(1992).

Compounds that include ringed systems are described by various investigators as effective for a variety of therapies and utilities. For example, International Patent Publication No. WO 98/25883 describes ketobenzamides as calpain inhibitors, European Patent Publication No. EP 811610 and U.S. Pat. Nos. 5,679,712, 5,693,672 and 5,747,541 describe substituted benzoylguanidine sodium channel blockers, U.S. Pat. No. 5,736,297 describes ring systems useful as a photosensitive composition.

U.S. Pat. Nos. 5,491,147, 5,608,070, 5,622,977, 5,739,144, 5,776,958, 5,780,477, 5,786,354, 5,798,373, 5,849,770, 5,859,034, 5,866,593, 5,891,896, and International Patent Publication WO 95/35283 describe PDE4 inhibitors that are tri-substituted aryl or heteroaryl phenyl derivatives. U.S. Pat. No. 5,580,888 describes PDE4 inhibitors that are styryl derivatives. U.S. Pat. No. 5,550,137 describes PDE4 inhibitors that are phenylaminocarbonyl derivatives. U.S. Pat. No. 5,340,827 describes PDE4 inhibitors that are phenylcarboxamide compounds. U.S. Pat. No. 5,780,478 describes PDE4 inhibitors that are tetra-substituted phenyl derivatives. International Patent Publication WO 96/00215 describes substituted oxime derivatives useful as PDE4 inhibitors. U.S. Pat. No. 5,633,957 describes PDE4 inhibitors that are cyclo(alkyl and alkenyl)phenyl-alkenyl (aryl and heteroaryl) compounds.

However, there remains a need for novel compounds and compositions that therapeutically inhibit PDE4 with minimal side effects.

SUMMARY OF THE INVENTION

The present invention is directed to biaryl substituted 1,8-naphthylidin-4(1H)-ones represented by Formula (I):

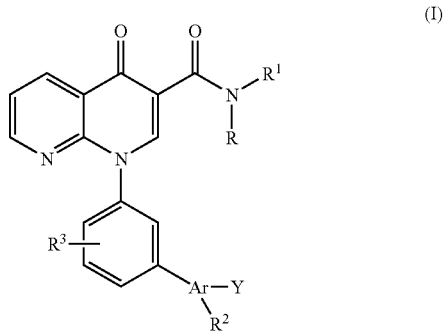

or pharmaceutically acceptable salts thereof, which are phosphodiesterase-4 inhibitors.

This invention also provides a pharmaceutical composition which includes an effective amount of the novel biaryl substituted 1,8-naphthyridin-4(1H)-ones and a pharmaceutically acceptable carrier. This invention further provides a method of treatment in mammals of, for example, asthma, chronic bronchitis, chronic obstructive pulmonary disease (COPD), eosinophilic granuloma, psoriasis and other benign or malignant proliferative skin diseases, endotoxic shock (and associated conditions such as laminitis and colic in horses), septic shock, ulcerative colitis, Crohn's disease, reperfusion injury of the myocardium and brain, inflammatory arthritis, osteoporosis, chronic glomerulonephritis, atopic dermatitis, urticaria, adult respiratory distress syndrome, infant respiratory distress syndrome, chronic obstructive pulmonary disease in animals, diabetes insipidus, allergic rhinitis, allergic conjunctivitis, vernal conjunctivitis, arterial restenosis, atherosclerosis, neurogenic inflammation, pain, cough, rheumatoid arthritis, ankylosing spondylitis, transplant rejection and graft versus host disease, hypersecretion of gastric acid, bacterial, fungal or viral induced sepsis or septic shock, inflammation and cytokine-mediated chronic tissue degeneration, osteoarthritis, cancer, cachexia, muscle wasting, depression, memory impairment, monopolar depression, acute and chronic neurodegenerative disorders with inflammatory components, Parkinson disease, Alzheimer's disease, spinal cord trauma, head injury, multiple sclerosis, tumour growth and cancerous invasion of normal tissues by the administration of an effective amount of the compounds of Formula I or a precursor compound which forms in vivo the compounds of Formula I which are phosphodiesterase-4 inhibitors. This invention further provides a method of enhancing cognition in healthy subjects.

DETAILED DESCRIPTION OF THE INVENTION

In one embodiment the invention is directed to compounds represented by Formula (I):

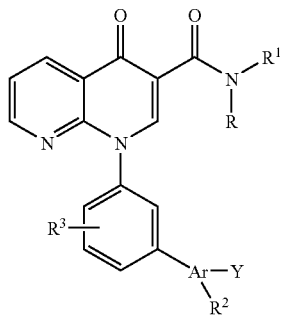

(I)

and pharmaceutically acceptable salts thereof, wherein

Ar is phenyl, pyridyl, pyrimidyl, indolyl, quinolinyl, thienyl, pyridonyl, oxazolyl, oxadiazolyl, thiadiazolyl, or imidazolyl; or oxides thereof when Ar is a heteroaryl;

Y is —COOH, —$C_{1-6}$alkyl($C_{1-4}$alkyl)$_n$—COOH, —$C_{3-4}$cycloalkyl($C_{1-4}$alkyl)$_m$—COOH, wherein the —$C_{1-6}$alkyl and the $C_{3-4}$cycloalkyl are optionally substituted with halogen, alkoxy, hydroxy or nitrile, and the ($C_{1-4}$alkyl) substituents are optionally linked to form a $C_{3-4}$cycloalkyl; wherein n is 0, 1, 2, 3 or 4, m is 0, 1 or 2;

R is H or —$C_{1-6}$alkyl;

$R^1$ is H, or —$C_{1-6}$alkyl, —$C_{3-6}$cycloalkyl, —$C_{1-6}$alkoxy, —$C_{2-6}$alkenyl, —$C_{3-6}$alkynyl, heteroaryl, or heterocycle group, optionally substituted with 1–3 independent halo$C_{1-6}$alkyl, —$C_{1-6}$alkyl, —$C_{1-6}$alkoxy, OH, amino, —($C_{0-6}$alkyl)—SO$_p$—($C_{1-6}$alkyl), nitro, CN, =N—O—$C_{1-6}$alkyl, —O—N=$C_{1-6}$alkyl, or halogen substituents, wherein p is 0, 1 or 2;

$R^2$ is H, halogen, —CN, —NO$_2$, —$C_{1-6}$alkyl, —$C_{3-6}$cycloalkyl, —O—$C_{3-6}$cycloalkyl, O—$C_{1-6}$alkyl, O—$C_{3-6}$cycloalkyl—$C_{1-6}$alkyl($C_{3-6}$cycloalkyl)($C_{3-6}$cycloalkyl), —$C_{1-6}$alkoxy, phenyl, heteroaryl, heterocycle, amino, —C(O)—$C_{1-6}$alkyl, —C(O)—O—$C_{1-6}$alkyl, —$C_{1-6}$alkyl (=N—OH), —C(N=NOH)$C_{1-6}$alkyl, —$C_{0-6}$alkyl(oxy)$C_{1-6}$alkyl-phenyl, —SO$_k$NH($C_{0-6}$alkyl), or —($C_{0-6}$alkyl)—SO$_k$—($C_{1-6}$alkyl), wherein the phenyl, heteroaryl or heterocycle is optionally substituted with halogen, —$C_{1-6}$alkyl, —$C_{1-6}$alkoxy, hydroxy, amino, or —C(O)—O—$C_{1-6}$alkyl, and wherein the alkyl or cycloalkyl is optionally substituted with 1–6 independently selected halogens or —OH, and wherein k is 0, 1, or 2;

$R^3$ is selected from H, halogen, CN, —$C_{1-6}$alkyl, —$C_{3-6}$cycloalkyl, nitro, —C(O)—$C_{1-6}$alkyl, —C(O)—O—$C_{0-6}$alkyl, —SO$_n$NH($C_{0-6}$alkyl), or —($C_{0-6}$alkyl)—SO$_{n'}$—($C_{1-6}$alkyl), O—$C_{1-6}$alkyl, O—$C_{3-6}$cycloalkyl, wherein n' is 0, 1, or 2 and wherein the alkyl and cycloalkyl is optionally substituted with 1–6 independently selected halogen or OH;

In an alternative, the group Y:

is

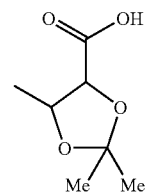

or —$C_{3-6}$cycloalkyl($C_{1-4}$alkyl)$_m$—COOH, wherein the $C_{3-6}$cycloalkyl is optionally substituted with halogen, alkoxy, hydroxy or nitrile, and the ($C_{1-4}$alkyl) substituents are optionally linked to form a $C_{3-6}$cycloalkyl; wherein n is 0, 1, 2, 3 or 4, m is 0, 1.

Within this embodiment there is a genus of compounds and pharmaceutically acceptable salts thereof wherein:

Y is —$C_{3-4}$cycloalkyl($C_{1-4}$alkyl)$_m$—COOH, wherein the $C_{3-4}$cycloalkyl is optionally Substituted with halogen, alkoxy, hydroxy or nitrile, and the ($C_{1-4}$alkyl) substituents are optionally linked to form a $C_{3-4}$cycloalkyl wherein n is 0, 1, 2, 3 or 4, m is 0, 1 or 2.

Within this embodiment there is another genus of compounds and pharmaceutically acceptable salts thereof wherein:

Y is cyclopropyl-COOH; and

Ar is phenyl.

Within this genus there is a sub-genus of compounds and pharmaceutically acceptable salts thereof wherein:

$R^1$ is —$C_{1-6}$alkyl optionally substituted with 1–3 independent —$C_{1-6}$alkyl, —$C_{1-6}$alkoxy, OH, amino, —($C_{0-6}$alkyl)—SO$_p$—($C_{1-6}$alkyl), nitro, CN, =N—O—$C_{1-6}$alkyl, —O—N=$C_{1-6}$alkyl, or halogen substituents.

Within this genus there is another sub-genus of compounds and pharmaceutically acceptable salts thereof wherein:

$R^1$ is —$C_{3-6}$cycloalkyl optionally substituted with 1–3 independent —$C_{1-6}$alkyl, —$C_{1-6}$alkoxy, OH, amino, —($C_{0-6}$alkyl)—SO$_p$—($C_{1-6}$alkyl), nitro, CN, =N—O—$C_{1-6}$alkyl, —O—N=$C_{1-6}$alkyl, or halogen substituents.

Within this genus there is another sub-genus of compounds and pharmaceutically acceptable salts thereof wherein:

R is hydrogen.

Within this genus there is another sub-genus of compounds and pharmaceutically acceptable salts thereof wherein:

$R^2$ is hydrogen or —$C_{1-3}$alkyl or halogen.

$R^3$ is, hydrogen or halogen.

Within this genus there is another sub-genus of compounds and pharmaceutically acceptable salts thereof wherein:

R is —$C_{3-6}$cycloalkyl optionally substituted with methyl or halo; and

R is hydrogen.

Within this genus there is another sub-genus of compounds and pharmaceutically acceptable salts thereof wherein:

$R^1$ is cyclopropyl optionally substituted with methyl or halo; and

R and $R^2$ are hydrogen;

$R_3$ is hydrogen or halogen.

In another aspect, within the embodiment described above, there is another genus of compounds and pharmaceutically acceptable salts thereof wherein:

Y is cyclopropyl—COOH; and

Ar is pyridyl, pyrimidyl, or oxide thereof.

Within this genus there is a sub-genus of compounds and pharmaceutically acceptable salts thereof wherein:

$R^1$ is —$C_{1-6}$alkyl optionally substituted with 1–3 independent —$C_{1-6}$alkyl, —$C_{1-6}$alkoxy, OH, amino, —($C_{0-6}$alkyl)—$SO_p$—($C_{1-6}$alkyl), nitro, CN, =N—O—$C_{1-6}$alkyl, —O—N=$C_{1-6}$alkyl, or halogen substituents.

Within this genus there is another sub-genus of compounds and pharmaceutically acceptable salts thereof wherein:

$R^1$ is —$C_{3-6}$cycloalkyl optionally substituted with 1–3 independent —$C_{1-6}$alkyl, —$C_{1-6}$alkoxy, OH, amino, —($C_{0-6}$alkyl)—$SO_p$—($C_{1-6}$alkyl), nitro, CN, =N—O—$C_{1-6}$alkyl, —O—N=$C_{1-6}$alkyl, or halogen substituents.

Within this genus there is another sub-genus of compounds and pharmaceutically acceptable salts thereof wherein:

R is hydrogen.

Within this genus there is another sub-genus of compounds and pharmaceutically acceptable salts thereof wherein:

$R^2$ is hydrogen or —$C_{1-3}$alkyl;

$R^3$ is hydrogen or halogen.

Within this genus there is another sub-genus of compounds and pharmaceutically acceptable salts thereof wherein:

$R^1$ is —$C_{3-6}$cycloalkyl optionally substituted with methyl or halo; and

R is hydrogen.

Within this genus there is another sub-genus of compounds and pharmaceutically acceptable salts thereof wherein:

$R^1$ is cyclopropyl optionally substituted with methyl or halo; and

R and $R^2$ are hydrogen;

$R_3$ is hydrogen or halogen

Illustrating the compounds of the invention are:

2-(trans)-{3'-[3-[(cyclopropylamino)carbonyl]-4-oxo-1,8-naphthyridin-1(4H)-yl]-1,1'-biphenyl-4-yl}cyclopropanecarboxylic acid;

2-{3'-[3-[(cyclopropylamino)carbonyl]-4-oxo-1,8-naphthyridin-1(4H)-yl]-1,1'-biphenyl-3-yl}cyclopropanecarboxylic acid;

2-{3'-[3-[(cyclopropylamino)carbonyl]-4-oxo-1,8-naphthyridin-1(4H)-yl]-1,1'-biphenyl-3-yl}-2-methylpropanoic acid;

2-{3'-[3-[(cyclopropylamino)carbonyl]-4-oxo-1,8-naphthyridin-1(4H)-yl]-1,1'-biphenyl-4-yl}-2-methylpropanoic acid;

3-{3'-[3-[(cyclopropylamino)carbonyl]-4-oxo-1,8-naphthyridin-1(4H)-yl]-1,1'-biphenyl-4-yl}-3-methylbutanoic acid;

{3'-[3-[(cyclopropylamino)carbonyl]-4-oxo-1,8-naphthyridin-1(4H)-yl]-1,1'-biphenyl-4-yl}(hydroxy)acetic acid;

1-{3'-[3-[(cyclopropylamino)carbonyl]-4-oxo-1,8-naphthyridin-1(4H)-yl]-1,1'-biphenyl-4-yl}cyclopropanecarboxylic acid;

2-(cis)-{3'-[3-[(cyclopropylamino)carbonyl]-4-oxo-1,8-naphthyridin-1(4H)-yl]-1,1'-biphenyl-4-yl}cyclopropanecarboxylic acid;

5-{3'-[3-[(cyclopropylamino)carbonyl]-4-oxo-1,8-naphthyridin-1(4H)-yl]-1,1'-biphenyl-4-yl}-2,2-dimethyl-1,3-dioxolane-4-carboxylic acid;

1-{3'-[3-[(cyclopropylamino)carbonyl]-4-oxo-1,8-naphthyridin-1(4H)-yl]-1,1'-biphenyl-3-yl}cyclopropanecarboxylic acid;

1-cyano-3-{3'-[3-[(cyclopropyl amino)carbonyl]-4-oxo-1,8-naphthyridin-1(4H)-yl]-1,1'-biphenyl-4-yl}-2,2-dimethylcyclopropanecarboxylic acid;

2-{3'-[3-[(cyclopropylamino)carbonyl]-4-oxo-1,8-naphthyridin-1(4H)-yl]-3-fluoro-1,1'-biphenyl-4-yl}cyclopropanecarboxylic acid;

(cis)-2-{3'-[3-[(cyclopropylamino)carbonyl]-4-oxo-1,8-naphthyridin-1(4H)-yl]1,1'-biphenyl-3-yl}cyclopropanecarboxylic acid;

2-{3'-bromo-5'-[3-[(cyclopropylamino)carbonyl]-4-oxo-1,8-naphthyridin-1(4H)-yl]-1,1'-biphenyl-4-yl}cyclopropanecarboxylic acid;

2-{3'-[3-[(cyclopropylamino)carbonyl]-4-oxo-1,8-naphthyridin-1(4H)-yl]-3-methyl-1,1'-biphenyl-4-yl}cyclopropanecarboxylic acid;

2-{3'-[3-[(cyclopropylamino)carbonyl]-4-oxo-1,8-naphthyridin-1(4H)-yl]-2-methyl-1,1'-biphenyl-4-yl}cyclopropanecarboxylic acid;

2-{3-chloro-3'-[3-[(cyclopropylamino)carbonyl]-4-oxo-1,8-naphthyridin-1(4H)-yl]-1,1'-biphenyl-4-yl}cyclopropanecarboxylic acid;

2-(cis)-{3'-[3-[(cyclopropylamino)carbonyl]-4-oxo-1,8-naphthyridin-1(4H)-yl]-3-fluoro-1,1'-biphenyl-4-yl}cyclopropanecarboxylic acid;

3'-[3-[(cyclopropylamino)carbonyl]-4-oxo-1,8-naphthyridin-1(4H)-yl]1,1'-biphenyl-4-carboxylic acid;

2-{3'-[3-(morpholin-4-ylcarbonyl)-4-oxo-1,8-naphthyridin-1(4H)-yl]1,1'-biphenyl-4-yl}cyclopropanecarboxylic acid;

2-{3'-[4-oxo-3-({[5-(trifluoromethyl)-1,3,4-thiadiazol-2-yl]amino}carbonyl)-1,8-naphthyridin-1(4H)-yl]1,1'-biphenyl-4-yl}cyclopropanecarboxylic acid;

2-{3'-[3-({[2-(methylthio)ethyl]amino}carbonyl)-4-oxo-1,8-naphthyridin-1(4H)-yl]-1,1'-biphenyl-4-yl}cyclopropanecarboxylic acid;

2-{3'-[3-({[2-(methylsulfonyl)ethyl]amino}carbonyl)-4-oxo-1,8-naphthyridin-1(4H)-yl]-1,1'-biphenyl-4-yl}cyclopropanecarboxylic acid;

2-{3'-[4-oxo-3-{[(2,2,2-trifluoroethyl)amino]carbonyl}-1,8-naphthyridin-1(4H)-yl]-1,1'-biphenyl-4-yl}cyclopropanecarboxylic acid;

2-(5-{3-[3-[(cyclopropylamino)carbonyl]-4-oxo-1,8-naphthyridin-1(4H)-yl]phenyl}thien-2-yl)cyclopropanecarboxylic acid;

2-{3'-[3-{[(cyclopropylmethyl)amino]carbonyl}-4-oxo-1,8-naphthyridin-1(4H)-yl]-1,1'-biphenyl-4-yl}cyclopropanecarboxylic acid;

2-{3'-[3-{[(1-cyanocyclopropyl)amino]carbonyl}-4-oxo-1,8-naphthyridin-1(4H)-yl]-1,1'-biphenyl-4-yl}cyclopropanecarboxylic acid, 3-{3'-[3-[(isopropylamino)carbonyl]-4-oxo-1,8-naphthyridin-1(4H)-yl]-1,1'-biphenyl-4-yl}-3-methylbutanoic acid; and pharmaceutically acceptable salts thereof.

In another embodiment the invention emcompasses a compound represented by Formula (I):

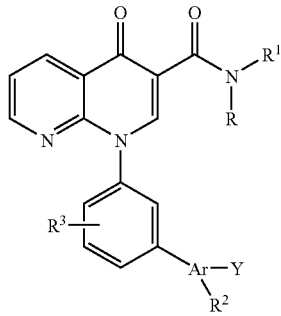

or a pharmaceutically acceptable salt thereof, wherein

Ar is phenyl, pyridyl, pyrimidyl, indolyl, quinolinyl, thienyl, pyridonyl, oxazolyl, oxadiazolyl, thiadiazolyl, or imidazolyl; or oxides thereof when Ar is a heteroaryl;

Y is —COOR$^4$, —C$_{1-6}$alkyl(C$_{1-4}$alkyl)$_n$—COOR$^4$, —C$_{3-4}$cycloalkyl(C$_{1-4}$alkyl)$_m$—COOR$^4$, wherein the —C$_{1-6}$alkyl and the C$_{3-4}$cycloalkyl is optionally substituted with halogen, alkoxy, hydroxy or nitrile, and the (C$_{1-4}$alkyl) substituents are optionally linked to form a C$_{3-4}$cycloalkyl; wherein n is 0, 1, 2, 3 or 4, m is 0, 1 or 2;

R and R4 are each independently selected from H and —C$_{1-6}$alkyl;

R$^1$ is H, or —C$_{1-6}$alkyl, —C$_{3-6}$cycloalkyl, —C$_{1-6}$alkoxy, —C$_{2-6}$alkenyl, —C$_{3-6}$alkynyl, heteroaryl, or heterocycle group, optionally substituted with 1–3 independent haloC$_{1-6}$alkyl, —C$_{1-6}$alkyl, —C$_{1-6}$alkoxy, OH, amino, —(C$_{0-6}$alkyl)—SO$_p$—(C$_{1-6}$alkyl), nitro, CN, =N—O—C$_{1-6}$alkyl, —O—N=C$_{1-6}$alkyl, or halogen substituents, wherein p is 0, 1 or 2, or R$^1$ is —C$_{1-6}$alkyl mono or di-substituted with substituents selected from phenyl and —C$_{3-6}$cycloalkyl;

R$^2$ is H, halogen, —CN, —NO$_2$, —C$_{1-6}$alkyl, —C$_{3-6}$cycloalkyl, —O—C$_{3-6}$cycloalkyl, O—C$_{1-6}$alkyl, O—C$_{3-6}$cycloalkyl—C$_{1-6}$alkyl(C$_{3-6}$cycloalkyl)(C$_{3-6}$cycloalkyl), —C$_{1-6}$alkoxy, phenyl, heteroaryl, heterocycle, amino, —C(O)—C$_{1-6}$alkyl, —C(O)—O—C$_{1-6}$alkyl, —C$_{1-6}$alkyl (=N—OH), —C(N=NOH)C$_{1-6}$alkyl, —C$_{0-6}$alkyl(oxy)C$_{1-6}$alkyl-phenyl, —SO$_k$NH(C$_{0-6}$alkyl), or —(C$_{0-6}$alkyl)—SO$_k$—(C$_{1-6}$alkyl), wherein the phenyl, heteroaryl or heterocycle is optionally substituted with halogen, —C$_{1-6}$alkyl, —C$_{1-6}$alkoxy, hydroxy, amino, or —C(O)—O—C$_{1-6}$alkyl, and wherein the alkyl or cycloalkyl is optionally substituted with 1–6 independently selected halogens or —OH, and wherein k is 0, 1, or 2;

R$^3$ is selected from H, halogen, CN, —C$_{1-6}$alkyl, —C$_{3-6}$cycloalkyl, nitro, —C(O)—C$_{1-6}$alkyl, —C(O)—O—C$_{0-6}$alkyl, —SO$_n$NH(C$_{0-6}$alkyl), or —(C$_{0-6}$alkyl)—SO$_n$—(C$_{1-6}$alkyl), O—C$_{1-6}$alkyl, O—C$_{3-6}$cycloalkyl, wherein n' is 0, 1 or 2 and wherein the alkyl and cycloalkyl is optionally substituted with 1–6 independently selected halogen or OH.

In one aspect, the compounds of the invention are useful in the treatment of cognitive deficit (such as memory impairment, mentioned elsewhere in this specification) due to psycological dysfunction, neurological deficit (such as stroke) or psychiatric dysfunction.

In another aspect, the present invention is directed to a method of enhancing cognition in a healthy subject comprising administering a safe cognition enhancing amount of a phosphodiesterase-4 inhibitor. In particular, this invention is directed to a method of enhancing memory, learning, retention, recall, awareness and judgement in health subjects comprising administering a safe and effective amount of a phosphodiesterase-4 inhibitor of Formula I.

For purposes of this application is defined as a subject with cognition in the normal range for the subjects age or other classification. Cognition of a healthy subject as well as cognition enhancement of the healthy subject is illustrated shown by testing the compounds in the Morris water maze as reported by McNamara and Skelton, *Psychobiology*, 1993, 21, 101–108. Further details of relevant methodology are described in WO 96/25948. Other assessments for measuring cognition enhancement include, but are not limited to the "T" Maze Test; Radial Arm Maze Test; Delayed Non-Match or Delayed Match Test; Passive Avoidance Procedure; 5 Choice Test, disclosed in WO 01/87281 A2, published Nov. 22, 2001.

For purposes of this specification, classes of healthy subjects includes juveniles, adults and seniors of average cognition; juveniles, adults and seniors of above average cognition; and juveniles, adults and seniors of below average cognition.

For purposes of this specification, juvenile human subjects is defined as a human subject less than 18 years of age. For purposes of this specification, adult human subject is defined as a human subject 18 years of age or older. Within this classification is a human adult 18 to 40 years of age. For purposes of this specification, senior human subjects is defined as a human subject 40 years of age or older. Within this classification is a human subject 55 years of age or older; 65 years of age or older; and 70 years of age or older.

As appreciated by those of skill in the art, beginning at about age 25, the cognition of the healthy human declines at a measurable and reproducible rates, as for example, measured by CAmbridge Neuropsychological Test Automated Battery (CANTAB, de Jager C A, Milwain E, Budge M. Early detection of isolated memory deficits in the elderly: the need for more sensitive neuropsychological tests. Psychol Med 2002 April; 32(3):483–91) or the Cognitive Drug Reseach Battery (CDR, Barker A, Jones R, Simpson P, Wesnes K. (1995). Scopolamine induced cognitive impairment as a predictor of cognitive decline in healthy elderly volunteers. International Journal of Geriatric Psychiatry 10: 1059–1062). Thus, by the time a human subject becomes a senior 40 years of age the decline in cognitive function has declined significant and would benefit from a method of memory enhancement.

As used herein, "alkyl" as well as other groups having the prefix "alk" such as, for example, alkoxy, alkanoyl, alkenyl, alkynyl and the like, means carbon chains which, may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains containing at least one unsaturated C—C bond.

The term "haloalkyl", such as "haloC$_{1-6}$alkyl", means alkyl substituted with one or more halo groups.

The term "cycloalkyl" means carbocycles containing no heteroatoms, and includes mono-, bi- and tricyclic saturated carbocycles, as well as fused ring systems. Such fused ring systems can include one ring that is partially or fully unsaturated such as a benzene ring to form fused ring systems such as benzofused carbocycles. Cycloalkyl includes such fused ring systems as spirofused ring systems. Examples of cycloalkyl include cyclopropyl, cyclobutyl, cyclopentyl, cyclohexyl, decahydronaphthalene, adamantane, indanyl, indenyl, fluorenyl, 1,2,3,4-tetrahydronaphalene and the like. Similarly, "cycloalkenyl" means carbocycles containing no heteroatoms and at least one non-aromatic C—C double bond, and include mono-, bi- and tricyclic partially saturated carbocycles, as well as benzofused cycloalkenes. Examples of cycloalkenyl include cyclohexenyl, indenyl, and the like.

The term "cycloalkyloxy" unless specifically stated otherwise includes a cycloalkyl group connected to the oxy connecting atom.

The term "alkoxy" unless specifically stated otherwise includes an alkyl group connected to the oxy connecting atom.

The term "aryl" unless specifically stated otherwise includes multiple ring systems as well as single ring systems such as, for example, phenyl or naphthyl.

The term "aryloxy" unless specifically stated otherwise includes multiple ring systems as well as single ring systems such as, for example, phenyl or naphthyl, connected through the oxy connecting atom to the connecting site.

Ther term "$C_0$–$C_6$alkyl" includes alkyls containing 6, 5, 4, 3, 2, 1, or no carbon atoms. An alkyl with no carbon atoms is a hydrogen atom substituent or a direct bond—depending on whether the alkyl is a terminus or a bridging moiety.

The term "hetero" unless specifically stated otherwise includes one or more O, S, or N atoms. For example, heterocycloalkyl and heteroaryl include ting systems that contain one or more O, S, or N atoms in the ring, including mixtures of such atoms. The hetero atoms replace ring carbon atoms. Thus, for example, a heterocyclo$C_5$alkyl is a five membered ring containing from 5 to no carbon atoms.

Examples of heteroaryl include, for example, pyridinyl, quinolinyl, isoquinolinyl, pyridazinyl, pyrimidinyl, pyrazinyl, quinoxalinyl, furyl, benzofuryl, dibenzofuryl, thienyl, benzothienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl, tetrazolyl.

The term "heteroaryloxy" unless specifically stated otherwise describes a heteroaryl group connected through an oxy connecting atom to the connecting site.

Examples of heteroaryl($C_{1-6}$)alkyl include, for example, furylmethyl, furylethyl, thienylmethyl, thienylethyl, pyrazolylmethyl, oxazolylmethyl, oxazolylethyl, isoxazolylmethyl, thiazolylmethyl, thiazolylethyl, imidazolylmethyl, imidazolylethyl, benzimidazolyl methyl, oxadiazolylmethyl, oxadiazolylethyl, thiadilazolylmethyl, thiadiazolylethyl, triazolylmethyl, triazolylethyl, tetrazolylmethyl, tetrazolylethyl, pyridinylmethyl, pyridinylethyl, pyridazinylmethyl, pyrimidinylmethyl, pyrazinylmethyl, quinolinylmethyl, isoquinolinylmethyl and quinoxalinylmethyl.

Examples of heterocyclo$C_{3-7}$alkyl include, for example, azetidinyl, pyrrolidinyl, piperidinyl, piperazinyl, morpholinyl, tetrahydrofuranyl, imidazolinyl, pyrolidin-2-one, piperidin-2-one, and thiomorpholinyl.

Examples of aryl($C_{1-6}$)alkyl include, for example, phenyl($C_{1-6}$)alkyl, and naphthyl($C_{1-6}$)alkyl.

Examples of heterocyclo$C_{3-7}$alkylcarbonyl($C_{1-6}$)alkyl include, for example, azetidinyl carbonyl($C_{1-6}$)alkyl, pyrrolidinyl carbonyl($C_{1-6}$)alkyl, piperidinyl carbonyl($C_{1-6}$)alkyl, piperazinyl carbonyl($C_{1-6}$)alkyl, morpholinyl carbonyl($C_{1-6}$)alkyl, and thiomorpholinyl carbonyl($C_{1-6}$)alkyl.

The term "amine" unless specifically stated otherwise includes primary, secondary and tertiary amines.

Unless otherwise stated, the term "carbamoyl" is used to include —NHC(O)O$C_1$–$C_4$alkyl, and —OC(O) NH$C_1$–$C_4$alkyl.

The term "halogen" includes fluorine, chlorine, bromine and iodine atoms.

The term "optionally substituted" is intended to include both substituted and unsubstituted. Thus, for example, optionally substituted aryl could represent a pentafluorophenyl or a phenyl ring. Further, the substitution can be made at any of the groups. For example, substituted aryl($C_{1-6}$) alkyl includes substitution on the aryl group as well as substitution on the alkyl group.

The term "oxide" of heteroaryl groups is used in the ordinary well-known chemical sense and include, for example, N-oxides of nitrogen heteroatoms.

Compounds described herein contain one or more double bonds and may thus give rise to cis/trans isomers as well as other conformational isomers. The present invention includes all such possible isomers as well as mixtures of such isomers.

Compounds described herein can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are benzenesulfonic, citric, hydrobromic, hydrochloric, maleic, phosphoric, sulfuric, and tartaric acids.

The pharmaceutical compositions of the present invention comprise a compound represented by Formula I (or pharmaceutically acceptable salts thereof) as an active ingredient, a pharmaceutically acceptable carrier and optionally other therapeutic ingredients or adjuvants. Such additional therapeutic ingredients include, for example, i) Leukotriene receptor antagonists, ii) Leukotriene biosynthesis inhibitors, iii) corticosteroids, iv) H1 receptor antagonists, v) beta 2 adrenoceptor agonists, vi) COX-2 selective inhibitors, vii) statins viii) non-steroidal anti-inflammatory drugs ("NSAID"), and ix) M2/M3 antagonists. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

Creams, ointments, jellies, solutions, or suspensions containing the compound of Formula I can be employed for topical use. Mouth washes and gargles are included within the scope of topical use for the purposes of this invention.

Dosage levels from about 0.001 mg/kg to about 140 mg/kg of body weight per day are useful in the treatment of conditions such as i) Pulmonary disorders such as asthma, chronic bronchitis, chronic obstructive pulmonary disease (COPD), adult respiratory distress syndrome, infant respiratory distress syndrome, cough, chronic obstructive pulmonary disease in animals, adult respiratory distress syndrome, and infant respiratory distress syndrome, ii) Gastrointestinal disorders such as ulcerative colitis, Crohn's disease, and hypersecretion of gastric acid, iii) Infectious diseases such as bacterial, fungal or viral induced sepsis or septic shock, endotoxic shock (and associated conditions such as laminitis and colic in horses), and septic shock, iv) Neurological disorders such as spinal cord trauma, head injury, neurogenic inflammation, pain, and reperfusion injury of the brain, v) Inflammatory disorders such as psoriatic arthritis, rheumatoid arthritis, ankylosing spondylitis, osteoarthritis, inflammation and cytokine-mediated chronic tissue degeneration, vi) Allergic disorders such as allergic rhinitis, allergic conjunctivitis, and eosinophilic granuloma, vii) Psychiatric disorders such as depression, memory impairment, and monopolar depression, viii) Neurodegenerative disorders such as Parkinson disease, Alzheimer's disease, acute and chronic multiple sclerosis, ix) Dermatological disorders such as psoriasis and other benign or malignant proliferative skin diseases, atopic dermatitis, and ulticaria, x) Oncological diseases such as cancer, tumor growth and cancerous invasion of normal tissues, xi) Metabolic disorders such as diabetes insipidus, xii) Bone disorders such as osteoporosis, xiii) Cardiovascular disorders such as arterial restenosis, atherosclerosis, reperfusion injury of the myocardium, and xiv) Other disorders such as chronic glomerulonephritis, vernal conjunctivitis, transplant rejection and graft versus host disease, and cachexia—which are responsive to PDE4 inhibition, or alternatively about 0.05 mg to about 7 g per patient per day. For example, inflammation may be effectively treated by the administration of from about 0.01 mg to 50 mg of the compound per kilogram of body weight per day, or alternatively about 0.5 mg to about 2.5 g per patient per day. Further, it is understood that the PDE4 inhibiting compounds of this invention can be administered at prophylactically effective dosage levels to prevent the above-recited conditions.

The amount of active ingredient that may be combined with the carrier materials to produce a single dosage form will vary depending upon the host treated and the particular mode of administration. For example, a formulation intended for the oral administration to humans may conveniently contain from about 0.5 mg to about 5 g of active agent, compounded with an appropriate and convenient amount of carrier material which may vary from about 5 to about 95 percent of the total composition. Unit dosage forms will generally contain between from about 0.01 mg to about 1000 mg of the active ingredient, typically 0.01 mg, 0.05 mg, 0.25 mg, 1 mg, 5 mg, 25 mg, 50 mg, 100 mg, 200 mg, 300 mg, 400 mg, 500 mg, 600 mg, 800 mg or 1000 mg.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

In practice, the compounds represented by Formula I, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compound represented by Formula I, or pharmaceutically acceptable salts thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

The compounds and pharmaceutical compositions of this invention have been found to exhibit biological activity as PDE4 inhibitors. Accordingly, another aspect of the invention is the treatment in mammals of, for example, i) Pulmonary disorders such as asthma, chronic bronchitis, chronic obstructive pulmonary disease (COPD), adult respiratory distress syndrome, infant respiratory distress syndrome, cough, chronic obstructive pulmonary disease in animals, adult respiratory distress syndrome, and infant respiratory distress syndrome, ii) Gastrointestinal disorders such as ulcerative colitis, Crohn's disease, and hypersecretion of gastric acid, iii) Infectious diseases such as bacterial, fungal or viral induced sepsis or septic shock, endotoxic shock (and associated conditions such as laminitis and colic in horses), and septic shock, iv) Neurological disorders such as spinal cord trauma, head injury, neurogenic inflammation, pain, and reperfusion injury of the brain, v) Inflammatory disorders such as psoriatic arthritis, rheumatoid arthritis, ankylosing spondylitis, osteoarthritis, inflammation and cytokine-mediated chronic tissue degeneration, vi) Allergic disorders such as allergic rhinitis, allergic conjunctivitis, and eosinophilic granuloma, vii) Psychiatric disorders such as depression, memory impairment, and monopolar depression, viii) Neurodegenerative disorders such as Parkinson disease, Alzheimer's disease, acute and chronic multiple sclerosis, ix) Dermatological disorders such as psoriasis and other benign or malignant proliferative skin diseases, atopic dermatitis, and urticaria, x) Oncological diseases Such as cancer, tumor growth and cancerous invasion of normal tissues, xi) Metabolic disorders such as diabetes insipidus, xii) Bone disorders such as osteoporosis, xiii) Cardiovascular disorders such as arterial restenosis, atherosclerosis, reperfusion injury of the myocardium, and xiv) Other disorders such as chronic glomerulonephritis, vernal conjunctivitis, transplant rejection and graft versus host disease, and cachexia—maladies that are amenable to amelioration through inhibition of the PDE4 isoenzyme and the resulting elevated cAMP levels—by the administration of an effective amount of the compounds of this invention. The term "mammals" includes humans, as well as other animals such as, for example, dogs, cats, horses, pigs, and cattle. Accordingly, it is understood that the treatment of mammals other than humans is the treatment of clinical correlating afflictions to those above recited examples that are human afflictions.

Further, as described above, the compound of this invention can be utilized in combination with other therapeutic compounds. In particular, the combinations of the PDE4 inhibiting compound of this invention can be advantageously used in combination with i) Leukotriene receptor antagonists, ii) Leukotriene biosynthesis inhibitors, iii) COX-2 selective inhibitors, iv) statins, v) NSAIDs, vi) M2/M3 antagonists, vii) corticosteroids, viii) H1 (histamine) receptor antagonists and ix) beta 2 adrenoceptor agonist.

Thus, for example, pulmonary disorders such as asthma, chronic bronchitis, chronic obstructive pulmonary disease (COPD), adult respiratory distress syndrome, infant respiratory distress syndrome, cough, chronic obstructive pulmonary disease in animals, adult respiratory distress syndrome, and infant respiratory distress syndrome can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

Gastrointestinal disorders such as ulcerative colitis, Crohn's disease, and hypersecretion of gastric acid can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

Infectious diseases such as bacterial, fungal or viral induced sepsis or septic shock, endotoxic shock (and associated conditions such as laminitis and colic in horses), and septic shock can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

Neurological disorders such as spinal cord trauma, head injury, neurogenic inflammation, pain, and reperfusion injury of the brain can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

Inflammatory disorders such as psoriatic arthritis, rheumatoid arthritis, ankylosing spondylitis, osteoarthritis, inflammation and cytokine-mediated chronic tissue degeneration can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

Allergic disorders such as allergic rhinitis, allergic conjunctivitis, and eosinophilic granuloma can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

Psychiatric disorders such as depression, memory impairment, and monopolar depression can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

Neurodegenerative disorders such as Parkinson disease, Alzheimer's disease, acute and chronic multiple sclerosis can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

Dermatological disorders such as psoriasis and other benign or malignant proliferative skin diseases, atopic dermatitis, and urticaria can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

Oncological diseases such as cancer, tumor growth and cancerous invasion of normal tissues can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

Metabolic disorders such as diabetes insipidus can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

Bone disorders such as osteoporosis, cardiovascular disorders such as arterial restenosis, atherosclerosis, reperfusion injury of the myocardium, and other disorders such as chronic glomerulonephritis, vernal conjunctivitis, transplant rejection and graft versus host disease, and cachexia can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

For enhancement of cognition (such as for of enhancied memory, learning, retention, recall, awareness and judgement), dosage levels from about 0.0001 mg/kg to about 50 mg/kg of body weight per day are useful or about 0.005 mg to about 2.5 g per patient per day. Alternatively, dosage levels from about 0.001 mg to 10 mg of the compound per kilogram of body weight per day, or alternatively about 0.05 mg to about 500 mg per patient per day.

The amount of active ingredient that may be combined with the carrier materials to produce a single dosage form will vary depending upon the host treated and the particular mode of administration. For example, a formulation intended for the oral administration to humans may conveniently contain from about 0.005 mg to about 2.5 g of active agent, compounded with an appropriate and convenient amount of carrier materia. Unit dosage forms will generally contain between from about 0.005 mg to about 1000 mg of the active ingredient, typically 0.005, 0.01 mg, 0.05 mg, 0.25 mg, 1 mg, 5 mg, 25 mg, 50 mg, 100 mg, 200 mg, 300 mg, 400 mg, 500 mg, 600 mg, 800 mg or 1000 mg, administered once, twice or three times a day.

The abbreviations used herein have the following tabulated meanings. Abbreviations not tabulated below have their meanings as commonly used unless specifically stated otherwise.

| | |
|---|---|
| Ac = | Acetyl |
| Bn = | Benzyl |
| CAMP | cyclic adenosine-3',5'-monophosphate |
| DBU = | 1,8-diazabicyclo[5.4.0]undec-7-ene |
| DIBAL = | diisobutylaluminum hydride |
| DMAP = | 4-(dimethylamino)pyridine |
| DMF = | N,N-dimethylformamide |
| Et$_3$N = | Triethylamine |
| GST | glutathione transferase |
| HMDS | Hexamethyldisilazide |
| LDA = | lithium diisopropylamide |
| m-CPBA = | metachloroperbenzoic acid |
| MMPP = | monoperoxyphthalic acid |
| MPPM = | monoperoxyphthalic acid, magnesium salt 6H$_2$O |
| Ms = | methanesulfonyl = mesyl = SO$_2$Me |
| Ms0 = | methanesulfonate = mesylate |
| NSAID = | non-steroidal anti-inflammatory drug |
| o-Tol = | ortho-tolyl |
| OXONE ® = | 2KHSO$_5$.KHSO$_4$.K$_2$SO$_4$ |
| PCC = | pyridinium chlorochromate |
| PDC = | pyridinium dichromate |
| PDE | Phosphodiesterase |
| Ph = | Phenyl |
| Phe = | Benzenediyl |
| PMB = | para-methoxybenzyl |
| Pye = | Pyridinediyl |
| r.t. = | room temperature |
| Rac. = | Racemic |
| SAM = | aminosulfonyl or sulfonamide or SO$_2$NH$_2$ |
| SEM = | 2-(trimethylsilyl)ethoxymethoxy |
| SPA = | scintillation proximity assay |
| TBAF = | tetra-n-butylammonium fluoride |
| TEA = | triethylamine |
| Th = | 2- or 3-thienyl |
| TFA = | trifluoroacetic acid |
| TFAA = | trifluoroacetic acid anhydride |
| THF = | Tetrahydrofuran |
| Thi = | Thiophenediyl |
| TLC = | thin layer chromatography |
| TMS-CN = | trimethylsilyl cyanide |
| TMSI | trimethylsilyl iodide |
| Tz = | 1H (or 2H)-tetrazol-5-yl |
| CAN | ceric ammonium nitrate |
| C$_3$H$_5$ = | Allyl |

Alkyl Group Abbreviations

| | |
|---|---|
| Me = | Methyl |
| Et = | ethyl |
| n-Pr = | normal propyl |
| i-Pr = | isopropyl |
| n-Bu = | normal butyl |
| i-Bu = | isobutyl |
| s-Bu = | secondary butyl |
| t-Bu = | tertiary butyl |
| c-Pr = | cyclopropyl |
| c-Bu = | Cyclobutyl |
| c-Pen = | cyclopentyl |
| c-Hex = | cyclohexyl |

Assays Demonstrating Biological Activity

LPS and FMLP-Induced TNF-α and LTB$_4$ Assays in Human Whole Blood

Whole blood provides a protein and cell-rich milieu appropriate for the study of biochemical efficacy of anti-inflammatory compounds such as PDE4-selective inhibitors. Normal non-stimulated human blood does not contain detectable levels of TNF-α and LTB$_4$. Upon stimulation with LPS, activated monocytes express and secrete TNF-α up to 8 hours and plasma levels remain stable for 24 hours. Published studies have shown that inhibition of TNF-α by increasing intracellular cAMP via PDE4 inhibition and/or enhanced adenylyl cyclase activity Occurs at the transcriptional level. LTB$_4$ synthesis is also sensitive to levels of intracellular cAMP and can be completely inhibited by PDE4-selective inhibitors. As there is little LTB$_4$ produced during a 24 hour LPS stimulation of whole blood, an additional LPS stimulation followed by fMLP challenge of human whole blood is necessary for LTB$_4$ synthesis by activated neutrophils. Thus, by using the same blood sample, it is possible to evaluate the potency of a compound on two surrogate markers of PDE4 activity in the whole blood by the following procedure.

Fresh blood was collected in heparinized tubes by venipuncture from healthy human volunteers (male and female). These subjects had no apparent inflammatory conditions and had not taken any NSAIDs for at least 4 days prior to blood collection. 500 µL aliquots of blood were pre-incubated with either 2 µL of vehicle (DMSO) or 2 µL of test compound at varying concentrations for 15 minutes at 37° C. This was followed by the addition of either 10 µL vehicle (PBS) as blanks or 10 µL LPS (1 µg/mL final concentration, #L-2630 (Sigma Chemical Co., St. Louis, Mo.) from *E. coli*, serotype 0111:B4; diluted in 0.1% w/v BSA (in PBS)). After 24 hours of incubation at 37° C., another 10 µL of PBS (blank) or 10 µL of LPS (1 µg/mL final concentration) was added to blood and incubated for 30 minutes at 37° C. The blood was then challenged with either 10 µL of PBS (blank) or 10 µL of fMLP (1 µM final concentration, #F-3506 (Sigma); diluted in 1% w/v BSA (in PBS)) for 15 minutes at 37° C. The blood samples were centrifuged at 1500×g for 10 minutes at 4° C. to obtain plasma. A 50 µL aliquot of plasma was mixed with 200 µL methanol for protein precipitation and centrifuged as above. The supernatant was assayed for LTB$_4$ using an enzyme immunoassay kit (#520111 from Cayman Chemical Co., Ann Arbor, Mich.) according to the manufacturer's procedure. TNF-α was assayed in diluted plasma (in PBS) using an ELISA kit (Cistron Biotechnology, Pine Brook, N.J.) according to manufacturer's procedure. The IC$_{50}$ values of the Examples generally ranged from 0.075 µM to 25 µM.

The IC$_{50}$ values of selected examples (TNF-α):

| Example: | IC50 (µM) |
|---|---|
| 1 | 0.3 |
| 2 | 0.1 |
| 5 | 0.075 |
| 8-(−)-isomer | 0.16 |
| 12-(−)-isomer | 0.5 |
| 17 | 0.09 |
| 24-(+)-isomer | 0.16 |
| 26 | 0.16 |
| 29 | 0.1 |
| 30 | 1.8 |

Anti-Allergic Activity In Vivo

Compounds of the invention have been tested for effects on an IgE-mediated allergic pulmonary inflammation induced by inhalation of antigen by sensitized guinea pigs. Guinea pigs were initially sensitized to ovalbumin under mild cyclophosphamide-induced immunosuppression, by intraperitoneal injection of antigen in combinations with aluminum hydroxide and pertussis vaccine. Booster doses of antigen were given two and four weeks later. At six weeks, animals were challenged with aerosolized ovalbumin while under cover of an intraperitoneally administered anti-histamine agent (mepyramine). After a further 48 h, bronchial alveolar lavages (BAL) were performed and the numbers of eosinophils and other leukocytes in the BAL fluids were counted. The lungs were also removed for histological examination for inflammatory damage. Administration of compounds of the Examples (0.001–10 mg/kg i.p. or p.o.), up to three times during the 48 h following antigen challenge, lead to a significant reduction in the eosinophilia and the accumulation of other inflammatory leukocytes. There was also less inflammatory damage in the lungs of animals treated with compounds of the Examples.

SPA Based PDE Activity Assay Protocol

Compounds which inhibit the hydrolysis of cAMP to AMP by the type-IV cAMP-specific phosphodiesterases were screened in a 96-well plate format as follows:

In a 96 well-plate at 30° C. was added the test compound (dissolved in 2 μL DMSO), 188 mL of substrate buffer containing [2,8-$^3$H] adenosine 3',5'-cyclic phosphate (cAMP, 100 nM to 50 μM), 10 mM MgCl$_2$, 1 mM EDTA, 50 mM Tris, pH 7.5. The reaction was initiated by the addition of 10 mL of human recombinant PDE4 (the amount was controlled so that ~10% product was formed in 10 min.). The reaction was stopped after 10 min. by the addition of 1 mg of PDE-SPA beads (Amersham Pharmacia Biotech, Inc., Piscataway, N.J.). The product AMP generated was quantified on a Wallac Microbeta® 96-well plate counter (EG&G Wallac Co., Gaithersburg, Md.). The signal in the absence of enzyme was defined as the background. 100% activity was defined as the signal detected in the presence of enzyme and DMSO with the background subtracted. Percentage of inhibition was calculated accordingly. IC$_{50}$ value was approximated with a non-linear regression fit using the standard 4-parameter/multiple binding sites equation from a ten point titration.

The IC$_{50}$ values of the Examples disclosed here under were determined with 100 nM cAMP using the purified GST fusion protein of the human recombinant phosphodiesterase IVb (met-248) produced from a baculovirus/Sf-9 expression system. The IC$_{50}$ values of the Examples disclosed here under ranged from 0.0.1 nM to 2300 nM.

The IC$_{50}$ values of selected examples:

| Example: | IC50 (nM) |
|---|---|
| 1 | 0.3 |
| 2 | 0.2 |
| 5 | 0.6 |
| 8-(−)-isomer | 0.7 |
| 12-(−)-isomer | 0.4 |
| 17 | 0.1 |
| 24-(+)-isomer | 0.4 |
| 26 | 0.2 |
| 29 | 0.3 |
| 30 | 0.4 |

The examples that follow are intended as an illustration of certain preferred embodiments of the invention and no limitation of the invention is implied.

Unless specifically stated otherwise, the experimental procedures were performed under the following conditions. All operations were carried out at room or ambient temperature—that is, at a temperature in the range of 18–25° C. Evaporation of solvent was carried out using a rotary evaporator under reduced pressure (600–4000 pascals: 4.5–30 mm Hg) with a bath temperature of up to 60° C. The course of reactions was followed by thin layer chromatography (TLC) and reaction times are given for illustration only. Melting points are uncorrected and "d" indicates decomposition. The melting points given are those obtained for the materials prepared as described. Polymorphism may result in isolation of materials with different melting points in some preparations. The structure and purity of all final products were assured by at least one of the following techniques: TLC, mass spectrometry, nuclear magnetic resonance (NMR) spectrometry or microanalytical data. When given, yields are for illustration only. When given, NMR data is in the form of delta (δ) values for major diagnostic protons, given in parts per million (ppm) relative to tetramethylsilane (TMS) as internal standard, determined at 300 MHz, 400 MHz or 500 MHz using the indicated solvent. Conventional abbreviations used for signal shape are: s. singlet; d. doublet; t. triplet; m. multiplet; br. broad; etc. In addition, "Ar" signifies an aromatic signal. Chemical symbols have their usual meanings; the following abbreviations have also been used: v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

Methods of Synthesis

Compounds of the present invention can be prepared according to the following methods. The substituents are the same as in Formula I except where defined otherwise.

The 1-(3-Bromo-phenyl)-1,4-dihydro-[1,8]naphthyridin-4-one-3-carboxamide of the general structure VII were prepared according to the general method described in Scheme 1. First, ethyl 2-chloronicotinoyl acetate (II) was condensed with triethyl orthoformate in the presence of acetic anhydride to afford 2-chloronicotinoyl acrylate (III). Upon addition of an appropriately substituted haloaryl amine of formula IV, the resulting 3-arylamino acrylate of type V is obtained. Cyclization of the V to the 1-haloaryl-1,4-dihydro[1,8]naphthyridin-4-one carboxylate of formula VI is achieved in presence of an excess of a strong base at room temperature. Alternatively, the intermediate VI can be obtained from a one pot procedure using for example 2-chloronicotynoyl chloride and ethyl N,N-dimethylamino acrylate and a haloaryl amine IV in presence of a base like triethylamine in a solvent such as acetonitrile. Hydrolysis of VI and subsequent coupling of the resulting carboxylic acid to an amine (RR$^1$NH$_2$) using HATU and Hunig's base affords the desired key arylbromide intermediate VII.

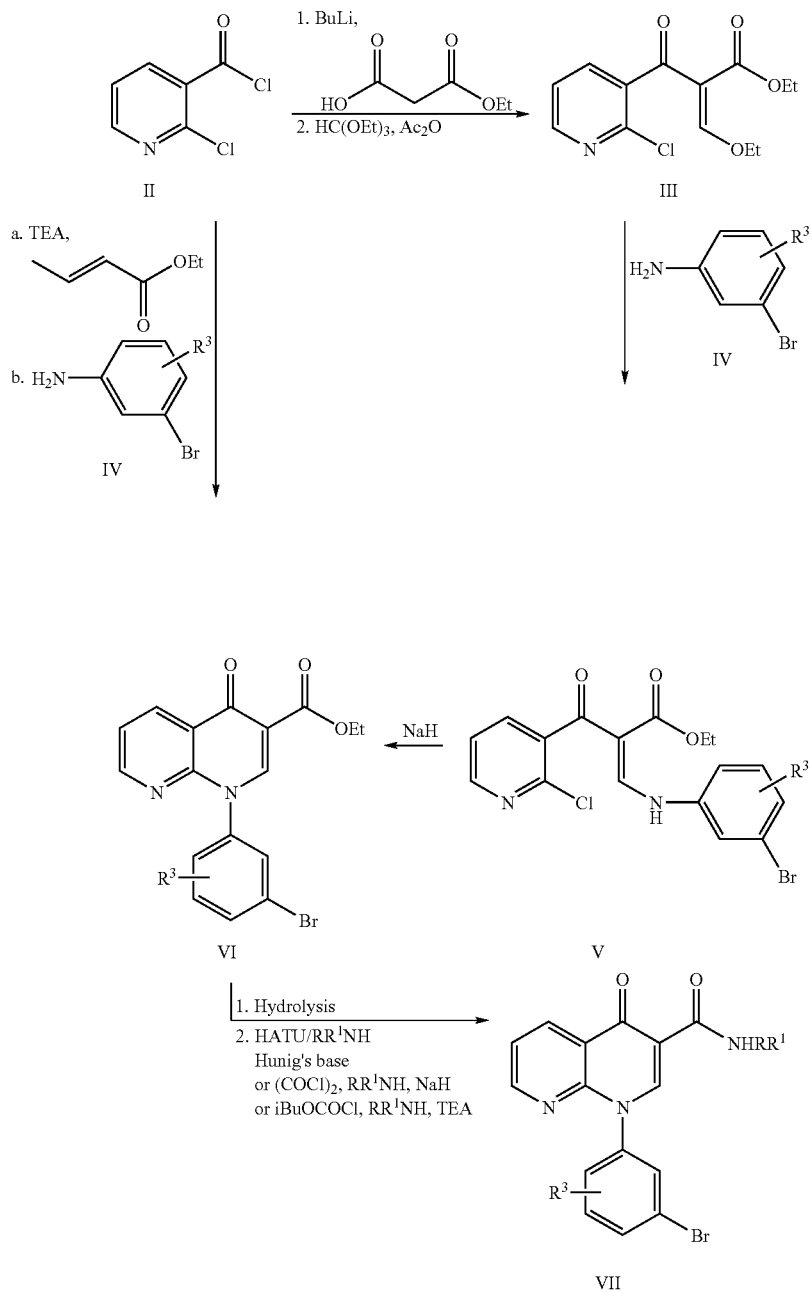

Scheme 1

Compounds of formula I were prepared using either of the following three general approaches. A palladium catalyzed Suzuki-Miyaura coupling between an aryl bromide of type VII and a properly substituted aryl pinacol boronate of type VIII can afford the desired compound I or the corresponding alkyl-ester IX. The ester LX can be hydrolyzed using LiOH in THF/MeOH to afford the desired acid I. Alternatively, the aryl bromide VII can be converted to the pinacol boronate XI by a palladium catalyzed coupling with pinacol-diborane. The previously described Suzuki-Miyaura reaction between XI and an aryl bromide of type XII can provide the acid I or the corresponding alkyl ester IX. Finally, a Stille coupling between an aryl bromide of type VII and a properly substituted aryl stannane of type X will also generate the desired acid of formula I.

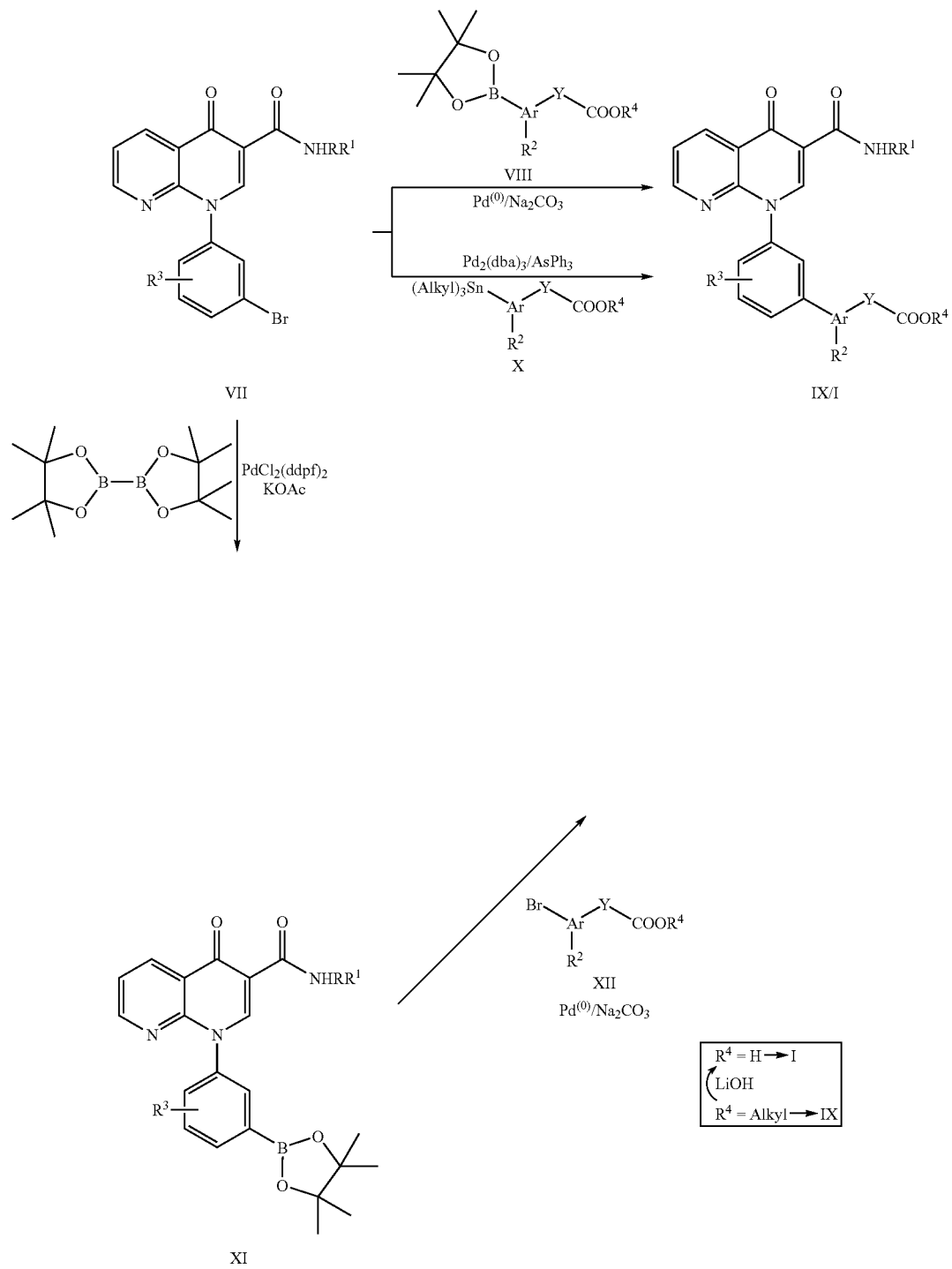

The boronate ester of type VIII and the stannane of type X (Scheme 3) can be both prepared from the aryl bromide XII intermediate by a palladium catalyzed coupling reaction using pinacol-diborane and hexaalkylditin respectively.

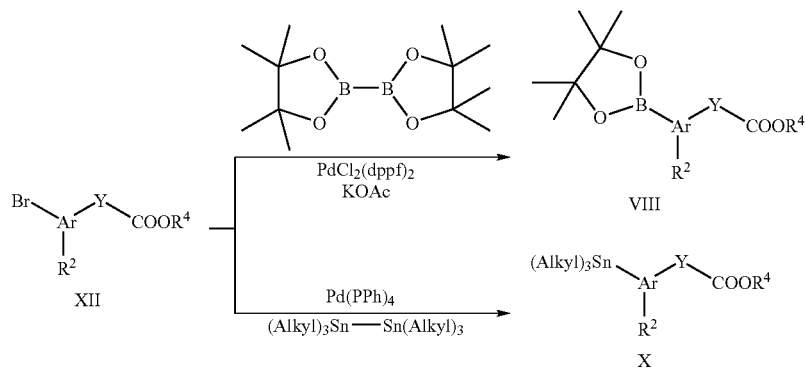

Scheme 3

Intermediates of type XII in which Y is a cyclopropane, as in compound of formula XIV can be prepared using either of the following four general procedures (Scheme 4). Cinnamic ester of type XIII, commercially available or prepared by a Horner-Emmons reaction from the corresponding aldehyde XV, can be cyclopropanated using diazomethane in the presence of a catalytic amount of palladium diacetate. The resulting trans cyclopropane ester XIV can be resolved by HPLC using a Chiral-Pak column to afford the two separate enantiomers. In a second approach, the aldehyde XV can be converted to the corresponding styrene XVI by a Wittig reaction followed by an enantioselective cyclopropanation using a bis-oxazoline chiral ligand/copper complex and diazoacetate (Evans et al. *J. Am. Chem. Soc.* 1991, 113, 726). The resulting mixture of trans XIV and cis XVII cyclopropane can be separated by selective hydrolysis under basic condition (rate of hydrolysis; trans>cis). Individual enantiomers (XIV or XVII) can be obtained by using either the R or S chiral ligand. The cis cyclopropane ester XIV can also be prepared from the cis-cinnamic ester XVIII, using the diazomethane/Pd(Ac)$_2$ procedure described earlier. The cis-cinnamic ester XVIII can by generated by a modified Horner-Emmons olefenation using a bis(trifluoroethyl) phosphonoester and a strong base (Still et al. *Tetrahedron Lett,* 1983, 24, 4405).

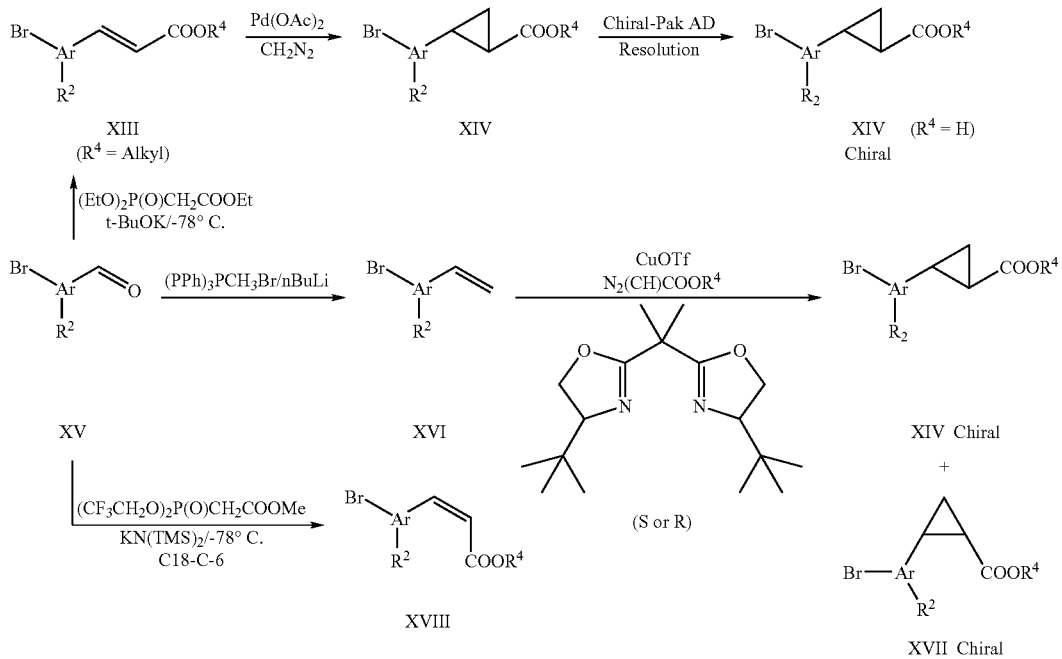

Scheme 4

Cis and trans chiral cyclopropane intermediates of type XIV and XVII respectively, can also be prepared by the following two methods. The cinnamic acid XIII in presence of CDI is converted to the acyl-imidazole XIX, which under basic condition reacts with the optically pure oxazolidinone XX to afford the chiral cinnamate-oxazolidinone XXI. Cyclopropanation of XXI following previously described method gives rise to a separable (crystallization, $SiO_2$) mixture (>5 to 1) of diastereoisomers XXII. Hydrolysis of the latter will afford the desired chiral cyclopropyl XIV. Similarly, a racemic mixture of cyclopropyl of type XIV (XVII) can be converted in two steps to the 1:1 diastereoisomeric mixture of the previously described cinnamate-oxazolidinone XXI.

NaOH in refluxing ethanol will give the desired acid XXX. The (1,1-dimethyl)ethyl-aryl of type XXXIII can be prepared in three steps. A (2-Chloro-1,1-dimethyl-ethyl)-aryl of type XXXI can be converted to the corresponding ester XXXII by first quenching the Grignard salt of XXXI with carbon dioxide followed by esterification of the resulting acid with diazomethane. Electrophilic substitution on the aryl ester XXXII in a media generating iodonium cation will afford the desired iodoaryl XXXIII (*J. Am. Chem. Soc.* 1948, 70, 370).

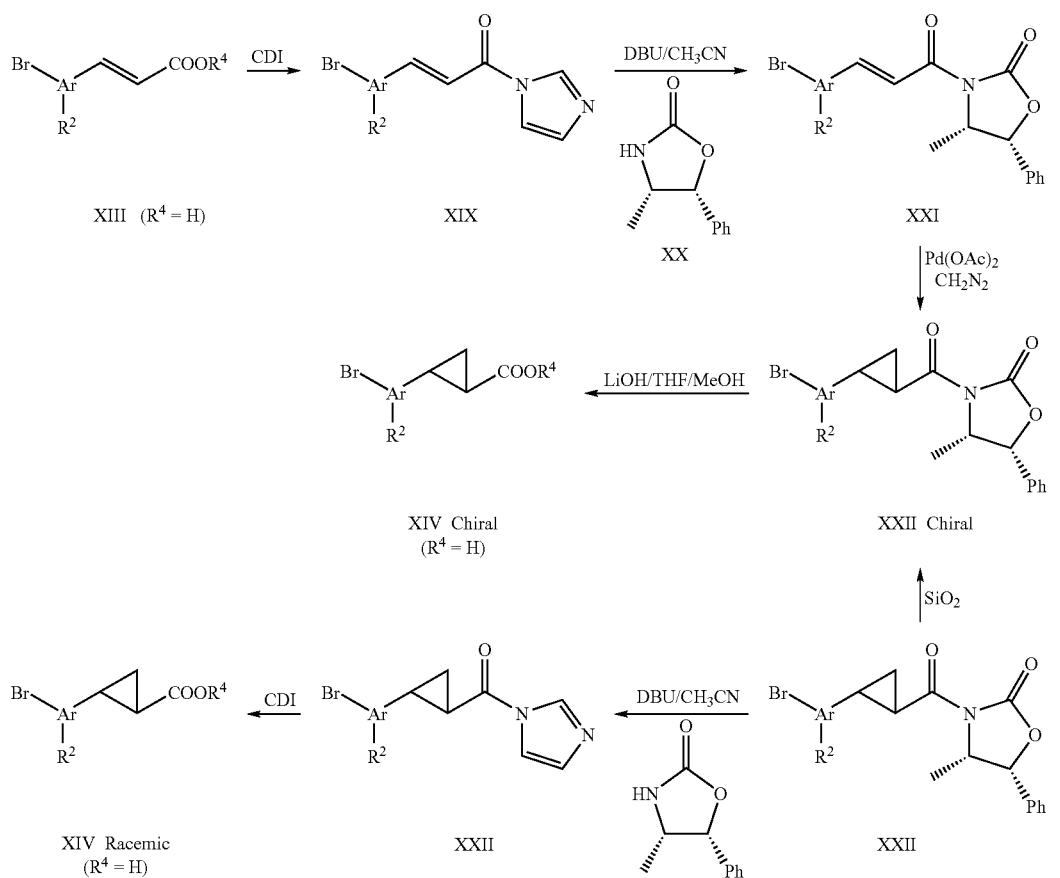

Intermediates of the type XXV (Scheme 6) can be obtained by deprotonation of an ester of type XXIV using an excess of strong base in presence of an alkylating agent such as $R^5I$. The relative amount of base and alkylating agent to the starting ester will establish to level of substitution (mono vs. bis). For propionic analogs of type XXVII, the tert-butyl ester XXVI can be deprotonated using a sterically hindered base. Addition of an alkylating reagent will give a mixture of mono and bis alkylated compound. Repeating the procedure will give mainly ester of type XXVII. The cyclopropyl analog of type XXX can be prepared in two steps from the corresponding aryl acetonitrile XXVIII. A phase transfer reaction using the nitrile XXVIII and 2-chloro bromoethane in strong aqueous base will yield the cyclopropylnitrile XXIX (*Org. Prep. & Proc.* 1995, 27, 355). Hydrolysis using

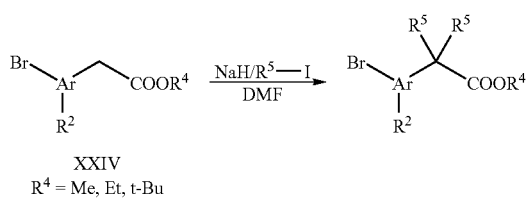

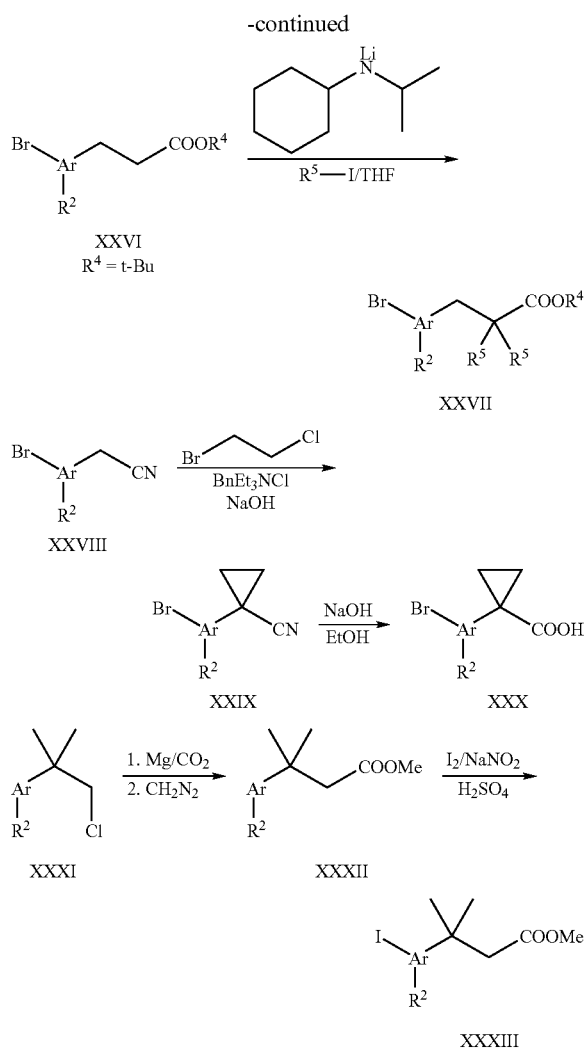
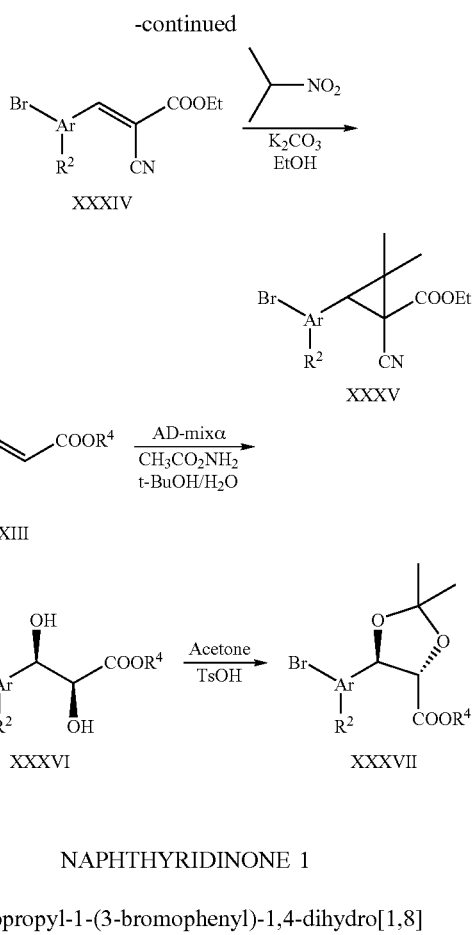

Substituted cyclopropyl of type XXXV can be prepared in two steps (Scheme 7). The Knoevenagel adduct XXXIV, resulting from the condensation of aldehyde XV and ethyl cyanoacetate, can be converted to the cyclopropyl XXXV in presence of 2-nitropropane and base in refluxing ethanol (*Tetrahedron Lett.* 1985, 26, 1923). Finally, cyclic acetal intermediates of type XXXVII can be prepared in two steps from the cinnamate XIII. Bis-hydroxylation of the cinnamate XIII using the condition developed by Sharpless et al. (AD-mix, J. Org. Chem. 1992, 57, 2768) will, after condensation with acetone in presence of a catalytic amount of acid of the diol XXXVI, afford the desired chiral acetal XXXVII.

Scheme 7

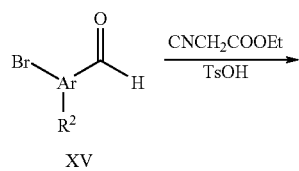

NAPHTHYRIDINONE 1

N-Isopropyl-1-(3-bromophenyl)-1,4-dihydro[1,8]naphthyridin-4-one-3-carboxamide

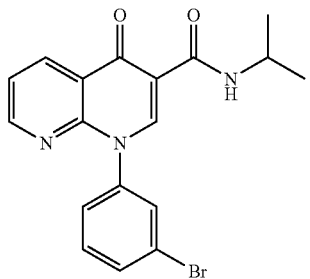

Step 1: Ethyl 3-(3-bromoanilino)-2-(2-chloronicotinoyl)acrylate

A mixture of ethyl 2-chloronicotinoyl acetate (prepared following a procedure described in J. Het. Chem., 30, 855, 1993) (1 eq), triethyl orthoformate (1.5 eq) and acetic anhydride (5 eq) was heated at 130° C. for 2.5 hours. The volatile components were distilled off and the residue was co-evaporated twice with xylene. The oily residue was dissolved in methylene chloride and 3-bromoaniline (1.2 eq) was added slowly. The resulting solution was stirred at room temperature for 18 hours, and the solvent evaporated away. The resulting crude compound was used as such in the next step.

Step 2: Ethyl 1-(3-bromophenyl)-1,4-dihydro[1,8]naphthyridin-4-one-3-carboxylate.

The crude compound from Step 1 was dissolved in tetrahydrofuran (0.3 M), the solution was cooled to 0° C., and sodium hydride (as a 60% dispersion in oil, 1.3 eq) was added in portions. After stirring at 0° C. for 1 hour, the mixture was allowed to warm up to room temperature. After 2 hours, water was added to the suspension and and the insoluble solid was filtered and washed copiously with water. When dry, the solid was stirred in ether at room temperature for 24 hours and filtered to afford the title compound as a cream-colored solid.

$^1$H NMR (Acetone-d$_6$) δ 1.32 (t, 3H), 4.29 (q, 2H), 7.54–7.63 (m, 2H), 7.69 (dd, 1H), 7.78 (dd, 1H), 7.93 (s, 1H), 8.66–8.71 (m, 3H).

Alternatively, the following procedure for step 1 to 2 can be used:

A mixture of 2-chloronicotinoyl chloride (1 eq), triethylamine (4 eq) and ethyl 3,3-dimethylaminoacrylate (1.5 eq) in acetonitrile (0.5M) was heated to reflux for 3 h, cooled to 40–50° C. and 3-bromoaniline (1 eq) was added. The reaction was heated to reflux overnight, cooled to rt, diluted with water (2 volume). The product was isolated by filtration and washed with water, ether or acetonitrile-water (1:1).

Step 3: 1-(3-Bromophenyl)-1,4-dihydro[1,8]naphthyridin-4-one-3-carboxylic acid

A suspension of ethyl 1-(3-bromophenyl)-1,4-dihydro[1,8]naphthyridin-4-one-3-carboxylate from Step 2 (1 eq) in a mixture of tetrahydrofuran-methanol (0.15M) and 1N aqueous sodium hydroxide (2 eq) was heated at ca 50° C. with stirring for 20 minutes. After cooling, the mixture was diluted with water and acidified with 1N aqueous HCl. After stirring for 45 minutes, the precipitate was filtered, washed well with water and dried to afford the title acid as a cream-colored solid.

$^1$H NMR (Acetone-d$_6$) δ 7.65 (t, 1H), 7.76 (m, 2H), 7.84 (d, 1H), 7.99 (s, 1H), 8.87 (m, 2H), 9.01 (s, 1H).

Step 4: N-Isopropyl-1-(3-bromophenyl)-1,4-dihydro[1,8]naphthyridin-4-one-3-carboxamide.

To a suspension of 1-(3-bromophenyl)-1,4-dihydro[1,8]naphthyridin-4-one-3-carboxylic acid from Step 3 (1 eq) and triethylamine (3 eq) in tetrahydrofuran (0.08M) at 0° C. was added isobutyl chloroformate (1.8 eq). After stirring at 0° C. for 2 hours, isopropylamine (5 eq) was added and the mixture was allowed to warm up to room temperature and stirred overnight. The mixture was then partitioned between ethyl acetate and water, the organic phase was dried and evaporated to a solid which was stirred in ether at room temperature for 3 hours and filtered to afford the N-Isopropyl-1-(3-bromophenyl)-1,4-dihydro[1,8]naphthyridin-4-one-3-carboxamide as a white solid.

$^1$H NMR (Acetone-d$_6$) δ 1.25 (d, 6H), 4.17 (m, 1H), 7.59–7.63 (m, 2H), 7.70 (d, 1H), 7.80 (d, 1H), 7.94 (s, 1H), 8.73 (m, 1H), 8.78 (d, 1H), 8.85 (s, 1H), 9.61 (br, NH).

NAPHTHYRIDINONE 2

N-Cyclopropyl-1-(3-bromophenyl)-1,4-dihydro[1,8]naphthyridin-4-one-3-carboxamide

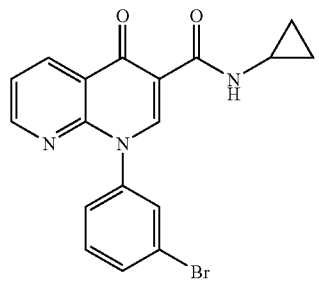

Following the procedure of NAPHTHYRIDINONE 1, but substituting cyclopropylamine for isopropylamine in step 4, the title compound was obtained as a fluffy white solid.

$^1$H NMR (Acetone-d$_6$) δ 0.59 (m, 2H), 0.80 (m, 2H), 2.96 (m, 1H), 7.59–7.68 (m, 2H), 7.72 (dd, 1H), 7.82 (dd, 1H), 7.97 (s, 1H), 8.72–8.81 (m, 2H), 8.89 (s, 1H), 9.70 (br, NH).

NAPHTHYRIDINONE 3

N-Cyclopropyl-4-oxo-1-[3-(4,4,5,5-tetramethyl-1,3,2-dioxaborolan-2-yl)phenyl]-1,4-dihydro-1,8-naphthyridine-3-carboxamide

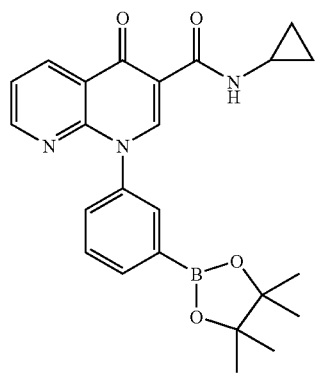

A mixture of NAPHTHYRIDINONE 2 (1.0 eq), pinacol diborane (1.5 eq), KOAc (4 eq) and PdCl$_2$(dppf) (0.05 eq) in DMF (0.2M) was stirred at 70–80° C. for 3 h. The mixture was cooled to rt, diluted with EtOAc and a NH$_4$Cl solution. The organic extracts were washed with H$_2$O, brine, dried over MgSO$_4$, filtered and concentrated. Crystallization from ether and flash chromatography (CH$_2$Cl$_2$:EtOAc, 50:50) of the mother liquor afforded the title compound as a white solid.

$^1$H NMR (500 MHz, acetone-d$_6$): δ 9.78 (s, 1H), 8.90 (s, 1H), 8.79 (dd, 1H), 8.72 (dd, 1H), 7.94 (d, 1H), 7.91 (s, 1H), 7.80 (d, 1H), 7.69 (t, 1H), 7.62 (dd, 1H), 2.9 (m, 1H), 1.38 (s, 12H), 0.80 (m, 2H), 0.60 (m, 2H).

NAPHTHYRIDINONE 4

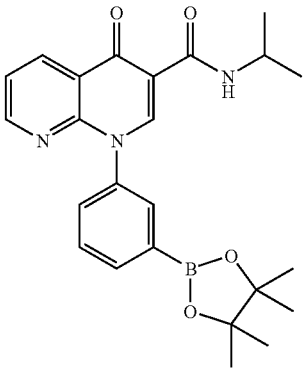

Prepared according to the procedure described in NAPHTHYRIDINONE 3 but using NAPHTHYRIDINONE 1 as starting material.

EXAMPLE 1

2-(trans)-{3'-[3-[(Cyclopropylamino)carbonyl]-4-oxo-1,8-naphthyridin-1(4H)-yl]-1,1'-biphenyl-4-yl}cyclopropanecarboxylic acid

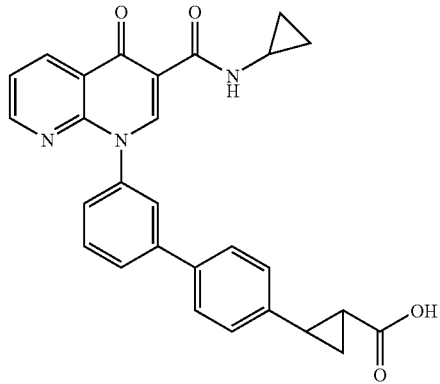

Step 1: Ethyl 2-(trans)-(4-bromophenyl)cyclopropanecarboxylate

To a mixture of ethyl 4-bromocinnamate and Pd(OAc)$_2$ (0.05 eq) in methylene chloride (1M) at 0° C. was added dropwise a solution of CH$_2$N$_2$ in ether until the reaction was completed by NMR analysis. The mixture was filtered through a plug of silica gel and concentrated to afford the title compound as an oil.

Step 2: Ethyl 2-(trans)-[4-(4,4,5,5-tetramethyl-1,3,2-dioxaborolan-2-yl)phenyl]cyclopropanecarboxylate A mixture of bromide from step 1 (1.0 eq), pinacol diborane ester (1.4 eq), KOAc (3.5 eq) and PdCl$_2$(dppf)$_2$ (0.03 eq) in DMF (0.14M) was stirred at 60° C. for 24 h. The resulting mixture was cooled to rt, diluted with EtOAc: hexane (1:1). The organic phase was washed with water (3×), brine, dried over MgSO$_4$, filtered and concentrated. Flash chromatography (hexane:EtOAc; 90:10) afforded the title compound.

Step 3: 2-(trans)-[4-(4,4,5,5-Tetramethyl-1,3,2-dioxaborolan-2-yl)phenyl]cyclopropanecarboxylic acid A mixture of ester from step 2 and NaOH (20%, 30 mL) was heated to 100° C. for 1.5 h, cooled to rt, acidified with HCl 10% and extracted with EtOAc. The organic extract was dried over Na$_2$SO$_4$ and the solvent evaporated to afford the title compound.

Step 4: 2-(trans)-{3'-[3-[(Cyclopropylamino)carbonyl]-4-oxo-1,8-naphthyridin-1(4H)-yl]-1,1'-biphenyl-4-yl}cyclopropanecarboxylic acid A mixture of NAPHTHYRIDINONE 2 (1.0 eq), acid from step 3 (1.5 eq), Na$_2$CO$_3$ (3.5 eq; 2M in H$_2$O), Pd(OAc)$_2$ (0.05 eq.) and PPh$_3$ (0.15 eq.) or PdCl$_2$dppf (0.05 eq) in n-propanol-DMF (1:1, 0.1M) was stilled at 70° C. for 2 h. The mixture was cooled to it, quenched with AcOH and diluted with EtOAc. The combined organic extracts were washed with brine, dried over Na$_2$SO$_4$, filtered and concentrated. Flash chromatography (CH$_2$Cl$_2$:EtOAc, 60:40, 2% AcOH) afforded the title compound as a white solid.

$^1$H NMR (500 MHz, CDCl$_3$): δ 9.9 (d, 1H), 9.08 (s, 1H), 8.77 (dd, 1H), 8.69 (dd, 1H), 7.71 (d, 1H), 7.60 (m, 2H), 7.52 (d, 2H), 7.45 (m, 1H), 7.38 (d, 1H), 7.13 (d, 2H), 2.97 (m, 1H), 2.54 (m, 1H), 1.87 (m, 1H), 1.60 (m, 1H), 1.35 (m, 1H), 0.85 (m, 2H), 0.65 (m, 2H). MS(H$^-$):464.2

The optically active isomers of EXAMPLE 1 can be isolated separately by chromatography using chiral column; for example Chiral Pak AD eluting with hexane:EtOH or hexane:iPrOH containing 0.2% TFA.

Alternatively, separation can be achieved on intermediate (trans)-2-(4-bromophenyl)cyclopropanecarboxylic acid (trans)-2-(4-Bromophenyl)cyclopropanecarboxylic acid To a solution of ester from step 1 in THF-MeOH (4:1, 0.5M) was added LiOH (3 eq, 2M) and the mixture was stirred at 50° C. for 1 h. The organic solvent evaporated, aqueous was acidified with HCl 1N and the acid extracted with EtOAc (3×). The organic was washed with brine, dried and solvent evaporated to afford 2-(4-bromophenyl)cyclopropanecarboxylic acid.

Optically active precursors are obtained by separation on chiral column (Chiral Pak AD) eluting with hexane:EtOH or hexane:iPrOH containing 0.2% TFA.

Another alternative is using a chiral auxiliary as follows,

Step 1: (trans)-3-(4-Bromo-phenyl)-1-imidazol-1-yl-propenone

To a solution of (trans)-3-(4-bromo-phenyl)acrylic acid (1.0 eq) in toluene (0.2M) was added CDI (1.5 eq). The mixture was stirred for 3 h at rt. The resulting precipitate was isolated by filtration to afford the title compound as a white solid.

Step 2: (trans)-3-[3-(4-Bromo-phenyl)-acryloyl]-4-methyl-5-phenyl-oxazolidin-2-one A mixture of 3-(4-bromo-phenyl)-1-imidazol-1-yl-propenone (1.05 eq) from Step 1, (4R, 5S)-(+)-4-methyl-5-phenyl-2-oxazolidinone (1.0 eq) or (−)-isomer and Et$_3$N (1.2 eq) in CH$_3$CN (0.2M) was refluxed overnight. The resulting mixture was cooled to rt, filtered on a pad of silica gel and concentrated. Crystallization in hexane:Et$_2$O afforded the title compound as a white solid.

Step 3: (trans)-3-[2-(4-Bromo-phenyl)cyclopropanecarbonyl]-4-methyl-5-phenyl-oxazolidin-2-one To a solution of (trans)-3-[3-(4-bromo-phenyl)-acryloyl]-4-methyl-5-phenyl-oxazolidin-2-one from Step 2 and Pd(OAc)$_2$ (0.05 eq.) in THF (0.2M) was added portionwise CH$_2$N$_2$ until the reaction was completed. NMR of aliquots monitored the reaction. The resulting mixture was concentrated and flash chromatography (Hex:EtOAc; 3:2) to afford the two separate diastereoisomers. Each diastereoisomer were submitted separately to next procedures to afford the (+) and (−) enantiomers of EXAMPLE 1.

Step 4: 2-(trans)-(4-Bromophenyl)cyclopropanecarboxylic acid

To a solution of amide from step 3 in THF-EtOH-H$_2$O (4:1:1, 0.1M) was added LiOH (2.4 eq, 2M) and the mixture was stirred at rt for 2 h. The mixture was neutralized to pH 7 with HCl 1N, the organic solvent evaporated and the resulting residue dissolved in ether. The organic was washed with NaOH 1N (2×). The combined aqueous layers were acidified and extracted with ether (3×). The organic extract was washed brine, dried and solvent evaporated to afford (+) or (−)-(trans)-2-(4-bromophenyl)cyclopropanecarboxylic acid as a white solid.

Step 5: 2-(trans)-{3'-[3-[(Cyclopropylamino)carbonyl]-4-oxo-1,8-naphthyridin-1(4H)-yl]-1,1'-biphenyl-4-yl cyclopropanecarboxylic acid A mixture of NAPHTHYRIDINONE 3 (1.0 eq), 2-(trans)-(4-bromophenyl)cyclopropanecarboxylic acid (1.2 eq.) from step 4, Na$_2$CO$_3$ (3.5 eq; 2M in H$_2$O), Pd(OAc)$_2$ (0.05 eq.) and PPh$_3$ (0.15 eq) in n-propanol (0.1M) was stirred at 70° C. for 4 h. The mixture was cooled to rt, poured in water and extracted with EtOAc (2×). The combined organic extracts were washed with brine, dried over Na$_2$SO$_4$, filtered and concentrated. Flash chromatography (CH$_2$Cl$_2$:EtOAc, 50:50, 2% AcOH) afforded the title compound as a white solid.

Another alternative is an enantioselective cyclopropanation using for example a bis-oxazoline chiral ligand/copper complex and diazoacetate (Evans et al. *J. Am. Chem. Soc.* 1991, 113, 726) to prepare optically active ethyl 2-(trans)-(4-bromophenyl)cyclopropanecarboxylate from 4-bromostyrene. Selective hydrolysis of the mixture of cis and trans isomer with LiOH (1 eq based on the trans ester) gave 2-(trans)-(4-bromophenyl)cyclopropanecarboxylic acid and ethyl 2-(cis)-(4-bromophenyl)cyclopropanecarboxylate which can be used in EXAMPLE 8.

EXAMPLE 2

2-{3'-[3-[(Cyclopropylamino)carbonyl]-4-oxo-1,8-naphthyridin-1(4H)-yl]-1,1'-biphenyl-3-yl}cyclopropanecarboxylic acid

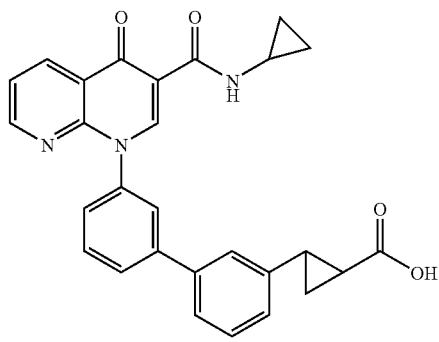

Step 1: Methyl 2-(trans)-(3-bromophenyl)cyclopropanecarboxylate

To a mixture of 3-bromocinnamic acid and Pd(OAc)$_2$ (0.05 eq) in methylene chloride (1M) at 0° C. was added dropwise a solution of CH$_2$N$_2$ in ether until the reaction was completed by NMR analysis. The mixture was filtered through a plug of silica gel and concentrated to afford the title compound.

Step 2: 2-(3-Bromophenyl)cyclopropanecarboxylic acid

To a solution of ester from step 1 in THF-MeOH (4:1, 0.5M) was added LiOH (3 eq, 2M) and the mixture was stirred at 50° C. for 1 h. The organic solvent evaporated, aqueous was acidified with HCl 1N and the acid extracted with EtOAc (3×). The organic was washed with brine, dried and solvent evaporated to afford 2-(3-bromophenyl)cyclopropanecarboxylic acid.

Step 3: 2-(trans)-{3'-[3-[(Cyclopropylamino)carbonyl]-4-oxo-1,8-naphthyridin-1(4H)-yl]1,1'-biphenyl-3-yl}cyclopropanecarboxylic acid A mixture of NAPHTHYRIDINONE 3 (1.0 eq), acid from step 2 (1.2 eq), Na$_2$CO$_3$ (3.5 eq.; 2M in H$_2$O) and PdCl$_2$(dppf) (0.05 eq) in n-propanol (0.1M) was stirred at 90° C. for 3 h. The mixture was cooled to rt, quenched with HCl and diluted with EtOAc. The combined organic extracts were washed with brine, dried over MgSO$_4$, filtered and concentrated. Flash chromatography (CH$_2$Cl$_2$:EtOAc: NH$_4$OH, 75:25:2.5) afforded the title compound as a white solid.

$^1$H NMR (500 MHz, ACETONE-D6) δ ppm 0.61 (m, 2H) 0.80 (m, 2H) 1.45 (m, 1 H) 1.52 (m, 1 H) 2.01 (m, 1 H) 2.54 (m, 1 H) 2.97 (dt, J=11.35, 3.47 Hz, 1 H) 7.25 (d, J=8.20 Hz, 1 H) 7.43 (t, J=7.57 Hz, 1 H) 7.63 (m, 4 H) 7.75 (t, J=7.88 Hz, 1 H) 7.95 (d, J=8.20 Hz, 1 H) 8.04 (s, 1 H) 8.75 (dd, J=4.41, 1.89 Hz, 1 H) 8.80 (dd, J=8.20, 1.89 Hz, 1 H) 8.96 (s, 1 H) 9.76 (s, 1 H).

EXAMPLE 3

2-{3'-[3-[(Cyclopropylamino)carbonyl]-4-oxo-1,8-naphthyridin-1(4H)-yl]-1,1'-biphenyl-3-yl}-2-methylpropanoic acid

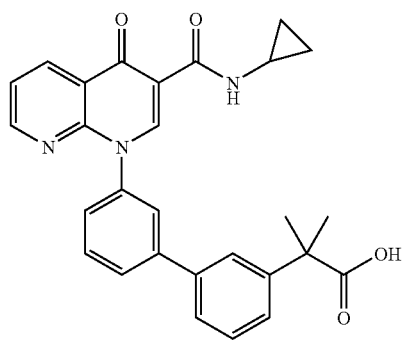

Step 1: Methyl 2-(3-bromophenyl)-2-methylpropanoate

To a Solution of LiHMDS (1M, THF, 2.1 eq) in THF (0.06M) was added methyl 3-bromophenylacetate (1 eq). After 15 min, MeI (4 eq) was added and the reaction mixture slowly warmed to rt and stirred for 18 h. The mixture was quenched with HCl 10%, diluted with EtOAc, washed with HCl 10%, brine, dried and solvent evaporated. Flash chromatography (Hexane:EtOAc:, 95: 5) afforded the title compound.

Step 2: 2-(3-Bromophenyl)-2-methylpropanoic acid

To a Solution of ester from step 1 in THF-MeOH (4:1, 0.5M) was added LiOH (3 eq, 2M) and the mixture was stirred at 50° C. for 1 h. The organic solvent evaporated, aqueous was acidified with HCl 1N and the acid extracted with EtOAc (3×). The organic was washed with brine, dried and solvent evaporated to afford the acid.

Step 3: 2-{3'-[3-[(Cyclopropylamino)carbonyl]-4-oxo-1,8-naphthyridin-1(4H)-yl]-1,1'-biphenyl-3-yl}-2-methylpropanoic acid A mixture of NAPHTHYRIDINONE 3 (1.0 eq), acid from step 2 (1.5 eq), $Na_2CO_3$ (3.5 eq.; 2M in $H_2O$) and $Pd(Ph_3)_4$ or PdCl2(dppf) or $Pd(OAc)_2(Ph3P)_3$ (0.05 eq) in n-propanol (0.1M) was stirred at 70–90° C. for 3 h. The mixture was cooled to rt, quenched with HCl and diluted with EtOAc. The combined organic extracts were washed with brine, dried over $MgSO_4$, filtered and concentrated. Flash chromatography ($CH_2Cl_2$:MeOH, 99:1) afforded the title compound as a white solid.

$^1$H NMR (500 MHz, acetone-d6): d 11.0 (s, OH), 9.76 (s, NH), 8.95 (s, 1H), 8.74 (dd, 1H), 8.71 (dd, 1H), 8.02 (s, 1H), 7:88 (d, 1H), 7.81 (s, 1H), 7.72 (t, 1H), 7.65 (m, 2H), 7.58 (dd, 1H), 7.46 (d, 1H), 2.94 (m, 1H), 1.61 (s, 6H), 0.77 (m, 2H), 0.58 (m, 2H). MS +ESI Q1 (M+1) 468.3

EXAMPLE 4

2-{3'-[3-[(Cyclopropylamino)carbonyl]-4-oxo-1,8-naphthyridin-1(4H)-yl]-1,1'-biphenyl-4-yl}-2-methylpropanoic acid

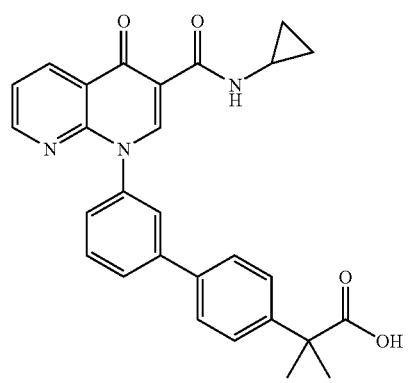

Prepared according to the procedure described in EXAMPLE 3, but using 4-bromophenylacetate as starting material. Flash chromatography ($CH_2Cl_2$:EtOAc, 40:60, 2% AcOH) afforded the title compound as a white solid.

$^1$H NMR (500 MHz, DMSO-d$_6$): δ 9.75 (d, 1H), 8.81 (s, 1H), 8.77 (m, 1H), 8.71 (d, 1H), 7.92 (s, 1H), 7.86 (d, 1H), 7.70 (d, 2H), 7.70–7.55 (m, 3H), 7.45 (d, 2H), 2.88 (m, 1H), 1.50 (s, 6H), 0.77 (m, 2H), 0.55 (m, 2H).

EXAMPLE 5

3-{3'-[3-[(Cyclopropylamino)carbonyl]-4-oxo-1,8-naphthyridin-1(4H)-yl]-1,1'-biphenyl-4-yl}-3-methylbutanoic acid

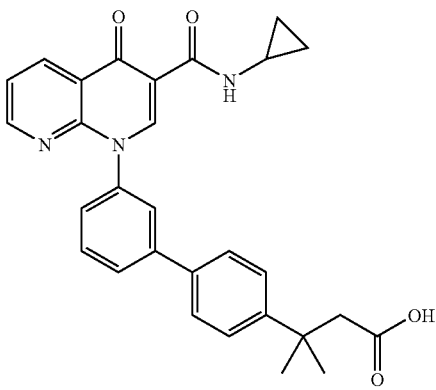

Prepared according to the procedure described in EXAMPLE 3, step 2 and 3 but using 3-(4-iodo-phenyl)-3-methyl-butyric acid methyl ester (prepared according to the procedure described in *J. Am. Chem. Soc.* 1948, 70, 370) as starting material. Flash chromatography ($CH_2Cl_2$:EtOAc, 40:60, 2% AcOH) afforded the title compound as a white solid.

$^1$H NMR (500 MHz, DMSO-d$_6$): δ 9.75 (d, 1H), 8.82 (s, 1H), 8.78 (dd, 1H), 8.72 (dd, 1H), 7.94 (s, 1H), 7.86 (d, 1H), 7.68–7.60 (m, 2H), 7.66 (d, 2H), 7.57 (d, 1H), 7.49 (d, 2H), 2.88 (m, 1H), 2.60 (s, 2H), 1.40 (s, 6H), 0.76 (m, 2H), 0.55 (m, 2H).

EXAMPLE 6

{3'-[3-[(Cyclopropylamino)carbonyl]-4-oxo-1,8-naphthyridin-1(4H)-yl]-1,1'-biphenyl-4-yl}(hydroxy)acetic acid

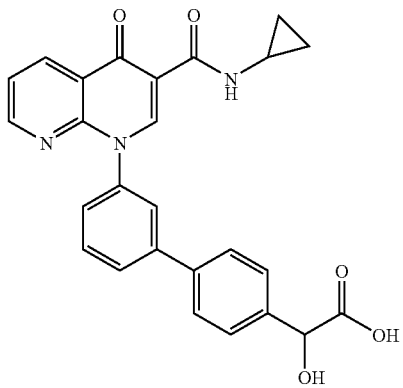

Prepared according to the procedure described in EXAMPLE 3, step 3, but using (4-bromomandelic acid) as starting material. Flash chromatography ($CH_2Cl_2$:MeOH, 9:1 to 8:2) then the residue was stirred vigorously in $CH_2Cl_2$/ether and isolated by filtration to afford the title compound as a white solid.

¹H NMR (500 MHz, acetone-d₆): δ 9.75 (d, 1H), 8.83 (s, 1H), 8.79 (dd, 1H), 8.74 (dd, 1H), 7.97 (s, 1H), 7.89 (d, 1H), 7.73 (d, 2H), 7.70 (t, 1H), 7.65 (dd, 1H), 7.61 (d, 1H), 7.52 (d, 2H), 5.03 (s, 1H), 2.92–2.90 (m, 1H), 0.80–0.77 (m, 2H), 0.59–0.56 (m, 2H).

EXAMPLE 7

1-{3'-[3-[(Cyclopropylamino)carbonyl]-4-oxo-1,8-naphthyridin-1(4H)-yl]-1,1'-biphenyl-4-yl}cyclopropanecarboxylic acid

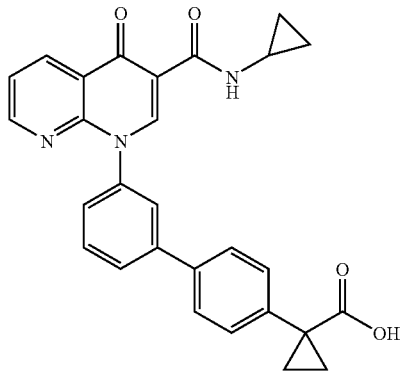

Step 1: 1-(4-Bromophenyl)cyclopropanecarbonitrile

A mixture of 4-bromophenylacetonitrile (1 eq), 1,2-bromochloroethane (1.5 eq), benzyltriethylammonium chloride (0.14 eq) in NaOH 50% (4M) was heated to 50° C. for 18 h. The mixture was cooled to rt, quenched with HCl 5% and diluted with ether. The combined organic extracts were washed with brine, dried over MgSO₄, filtered and concentrated. Flash chromatography (hexane:EtOAc, 95:5) afforded the title compound.

Step 2: 1-(4-Bromophenyl)cyclopropanecarboxylic acid

A mixture of nitrile (1 eq) from step 1, NaOH 25% (12 eq) in EtOH (0.5M) was heated to 100° C. for 5 h. The mixture was cooled to rt, quenched with AcOH and diluted with ether. The combined organic extracts were washed with brine, dried over MgSO₄, filtered and concentrated. Flash chromatography (hexane:EtOAc, 90:10 to 50:50) afforded the title compound.

Step 3: 1-{3'-[3-[(Cyclopropylamino)carbonyl]-4-oxo-1,8-naphthyridin-1(4H)-yl]-1,1'-biphenyl-4-yl}cyclopropanecarboxylic acid Prepared according to the procedure described in EXAMPLE 3, step 3 but using acid from step 2 as starting material. Flash chromatography (CH₂Cl₂:MeOH, 98:2) afforded the title compound as a white solid.

¹H NMR (500 MHz, acetone-d₆): δ 9.92 (d, 1H), 9.77 (d, 1H), 8.96 (s, 1H), 8.79 (dd, 1H), 8.74 (dd, 1H), 8.00 (s, 1H), 7.76–7.72 (m, 3H), 7.65 (dd, 1H), 7.61 (dd, 1H), 7.52 (d, 2H), 2.98–2.94 (m, 1H), 1.60–1.58 (m, 2H), 1.25–1.22 (m, 2H), 0.82–0.78 (m, 2H), 0.62–0.59 (m, 2H).

EXAMPLE 8

2-(cis)-{3'-[3-[(Cyclopropylamino)carbonyl]-4-oxo-1,8-naphthyridin-1(4H)-yl]-1,1'-biphenyl-4-yl}cyclopropanecarboxylic acid

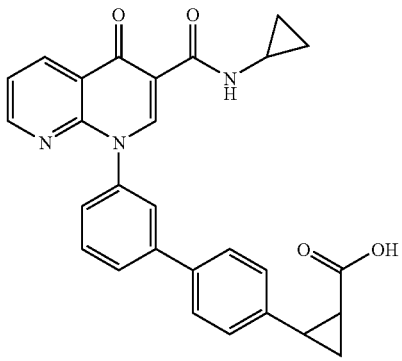

Step 1: Methyl 2-(cis)-3-(4-bromophenyl)prop-2-enoate

To a solution of bis(trifluoroethyl)(methoxycarbonylmethyl)phosphonate and 18-Crown-6 (5 eq) in THF (0.05M) at −78° C. was added KHMDS (1 eq, 0.5M, toluene) followed by 4-bromobenzaldehyde (1 eq). The reaction mixture was stirred at −78° C. 1 h, quenched with a saturated ammonium chloride solution and diluted with ether. The combined organic extracts were washed with brine, dried over Na₂SO₄, filtered and concentrated. Flash chromatography (Hexane:EtOAc; 9:1 to 7:3) afforded the title compound.

Step 2: Methyl 2-(cis)-(4-bromophenyl)cyclopropanecarboxylate

To a mixture of ester from step 1 and Pd(OAc)₂ (0.05 eq) in methylene chloride (1M) at 0° C. was added dropwise a solution of CH₂N₂ in ether until the reaction was completed by NMR analysis. Flash chromatography (Hexane:EtOAc; 100:0 to 90:10) afforded the title compound.

Step 3: Methyl 2-{3'-[3-[(cyclopropylamino)carbonyl]-4-oxo-1,8-naphthyridin-1(4H)-yl]-1,1'-biphenyl-4-yl}cyclopropanecarboxylate Prepared according to the procedure described in EXAMPLE 3, step 3 but using ester from Example 8, step 2 as starting material. The product was purified by flash chromatography (hexane:EtOAc, 60:40), then vigorous stirring in hexane/ether and isolation by filtration to afford the title compound as a white solid.

Step 4: 2-(cis)-{3'-[3-[(Cyclopropylamino)carbonyl]-4-oxo-1,8-naphthyridin-1(4H)-yl]-1,1'-biphenyl-4-yl}cyclopropanecarboxylic acid To a solution of ester in THF-EtOH (1:1, 0.05M) was added LiOH (5 eq, 2M) and the mixture was stirred at 60° C. for 4 h. The mixture was cooled to rt, extracted with ether. The aqueous was acidified with HCl 1N and the acid extracted with EtOAc (3×). The organic was washed with brine, dried and solvent evaporated. The residue was stirred vigorously in CH₂Cl₂/hexane/acetone and isolated by filtration to afford the title compound as an off-white solid.

¹H NMR (500 MHz, DMSO-d₆): δ 11.88 (br s, 1H), 9.75 (d, 1H), 8.80 (s, 1H), 8.79 (dd, 1H), 8.74 (dd, 1H), 7.95 (s, 1H), 7.87 (d, 1H), 7.63–7.70 (m, 4H), 7.59 (d, 1H), 7.35 (d,

2H), 2.89–2.93 (m, 1H), 2.62 (dd, 1H), 2.04–2.09 (m, 1H), 1.31–1.35 (m, 1H), 0.77–0.87 (m, 2H), 0.56–0.59 (m, 2H).

The optically active diastereoisomers of EXAMPLE 8 can be isolated separately by chromatography using chiral column; for example Chiral Pak AD eluting with hexane:EtOH or hexane:iPrOH containing 0.2% TFA.

Alternatively, the optically active intermediate can be obtained as follow:

(cis)-2-(4-Bromophenyl)cyclopropanecarboxylic acid

To a solution of ester from step 2 in THF-MeOH (4:1, 0.5M) was added LiOH (3 eq, 2M) and the mixture was stirred at 50° C. for 1 h. The organic solvent was evaporated, the aqueous layer was acidified with HCl 1N and the acid extracted with EtOAc (3×). The combinedorganic extracts were washed with brine, dried and evaporated to afford 2-(4-bromophenyl)cyclopropanecarboxylic acid. Optically active intermediates were obtained by separation on chiral column (Chiral Pak AD) using hexane:EtOH (90:10 with 0.2% TFA).

Another alternative is using chiral auxiliary as follows,

Step 1: (cis)-1-{[2-(4-Bromophenyl)cyclopropyl]carbonyl}-1H-imidazole

To a solution of (cis)-2-(4-bromophenyl)cyclopropanecarboxylic acid (1.0 eq.) in toluene (0.2M) was added CDI (1.5 eq.). The mixture was stirred for 18 h at 50° C. The solvent evaporated, the resulting residue stirred vigorously in hexane/CH$_2$Cl$_2$, filtered, the filtrate evaporated to afford the title compound as a white solid.

Step 2: (cis)-3-{[2-(4-Bromophenyl)cyclopropyl]carbonyl}-4-methyl-5-phenyl-1,3-oxazolidin-2-one A mixture of (cis)-1-{[2-(4-bromophenyl)cyclopropyl]carbonyl}-1H-imidazole (1 eq) from Step 1, (4R, 5S)-(+)-4-methyl-5-phenyl-2-oxazolidinone (1.2 eq) or (−)-isomer and DBU (added at 0° C., 1.2 eq) in CH$_3$CN (0.2M) was stirred at 0° C. for 4 h. The solvent evaporated and residue purified by flash chromatography (Hexane:EtOAc; 100:0 to 80:20) to afford each diastereoisomer.

Step 3: (cis)-2-(4-Bromophenyl)cyclopropanecarboxylic acid

To a solution of amide (either (+) or (−) isomer) from step 2 above) in THF—H$_2$O (4:1, 0.5M) at 0° C. was added LiOH (1.6 eq, 2M) and H$_2$O$_2$(35%, 4 eq). The mixture was stirred at 0° C. for 4 h. The organic solvent was evaporated, the mixture extracted with CH$_2$Cl$_2$, the aqueous was acidified with HCl 1N and the acid extracted with EtOAc (3×). The combined organic extracts were washed with brine, dried and solvent evaporated to afford either (+) or (−) optically active (cis)-2-(4-bromophenyl)cyclopropanecarboxylic acid.

Another alternative is an enantioselective cyclopropanation using for example a bis-oxazoline chiral ligand/copper complex and diazoacetate (Evans et al. *J. Am. Chem. Soc.* 1991, 113, 726) to prepare optically active ethyl 2-(cis)-(4-bromophenyl)cyclopropanecarboxylate from 4-bromostyrene. Selective hydrolysis of the mixture of cis and trans isomer with LiOH (1 eq based on trans isomer) gave 2-(trans)-(4-bromophenyl)cyclopropanecarboxylic acid (used in EXAMPLE 1) and the desired ethyl 2-(cis)-(4-bromophenyl)cyclopropanecarboxylate.

EXAMPLE 9

5-{3'-[3-[(Cyclopropylamino)carbonyl]-4-oxo-1,8-naphthyridin-1(4H)-yl]-1,1'-biphenyl-4-yl}-2,2-dimethyl-1,3-dioxolane-4-carboxylic acid

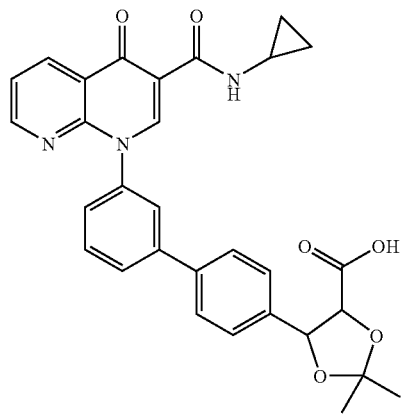

Step 1: Ethyl 3-(4-bromophenyl)-2,3-dihydroxypropanoate

Following a procedure described in J. Org. Chem, 1992, 57, 2768, using ethyl 4-bromocinnamate as starting material. The residue was purified by flash chromatography (Hexane: EtOAc; 50:50) to afford the title compound.

Step 2: Ethyl 5-(4-bromophenyl)-2,2-dimethyl-1,3-dioxolane-4-carboxylate

A solution of diol from step 1 (1 eq) in acetone (0.2M), dimethoxypropane (8 eq) and pTsOH (0.05 eq) was stirred at rt for 4 h. The solvent was evaporated, the residue dissolved in EtOAc and washed with aqueous NaHCO$_3$ sol. The organic extract was washed with brine, dried over Na$_2$SO$_4$, filtered and concentrated. Flash chromatography (hexane:EtOAc, 95:5 to 85:15) afforded the title compound.

Step 3: Ethyl 5-{3'-[3-[(cyclopropylamino)carbonyl]-4-oxo-1,8-naphthyridin-1(4H)-yl]1,1'-biphenyl-4-yl}-2,2-dimethyl-1,3-dioxolane-4-carboxylate A mixture of NAPHTHYRIDINONE 3 (1.0 eq), ester from step 2 (1.2 eq), Na$_2$CO$_3$ (2.5 eq.; 2M in H$_2$O) and Pd(OAc)$_2$(Ph$_3$P)$_3$ (0.05 eq) in DMF-H$_2$O (0.3M) was stirred at 80° C. for 4 h. The mixture was cooled to rt, diluted with EtOAc and filtered through Celite (washed with EtOAc). The organic extracts were washed with brine, dried over MgSO$_4$, filtered and concentrated. Flash chromatography (hexane:EtOAc, 30:70) afforded the title compound as a white solid.

Step 4: 5-{3'-[3-[(Cyclopropylamino)carbonyl]-4-oxo-1,8-naphthyridin-1(4H)-yl]-1,1'-biphenyl-4-yl}-2,2-dimethyl-1,3-dioxolane-4-carboxylic acid To a solution of ester from step 3 in THF-MeOH (1:1, 0.5M) was added LiOH (3 eq, 2M) and the mixture was stirred at 50° C. for 15 min. The organic solvent evaporated, aqueous was acidified with HCl 1N and the acid extracted with EtOAc (3×). The combined organic extract was washed with brine, dried and solvent evaporated, the residue triturated in hexane/ether then isolated by filtration to afford the title acid.

$^1$H NMR (500 MHz, acetone-d$_6$): δ 11.4 (br s, 1H), 9.76 (d, 1H), 8.97 (s, 1H), 8.79 (dd, 1H), 8.75 (dd, 1H), 8.02 (t, 1H), 7.94 (d, 1H), 7.83 (d, 2H), 7.76 (t, 1H), 7.60–7.68 (m, 4H), 5.27 (d, 1H), 4.40 (d, 1H), 2.95–2.99 (m, 1H), 1.58 (s, 3H), 1.53 (s, 3H), 0.79–0.82 (m, 2H), 0.59–0.63 (m, 2H).

EXAMPLE 10

1-{3'-[3-[(Cyclopropylamino)carbonyl]-4-oxo-1,8-naphthyridin-1(4H)-yl]-1,1'-biphenyl-3-yl}cyclopropanecarboxylic acid

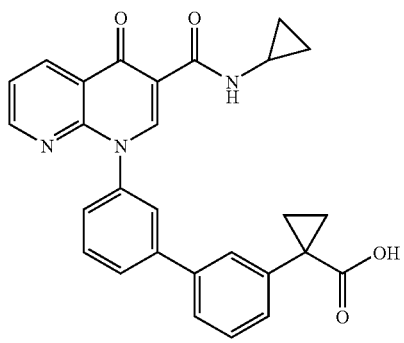

Prepared according to the procedure described in EXAMPLE 7, but using 3-bromophenylacetonitrile as starting material. The residue was purified by flash chromatography (CH$_2$Cl$_2$:MeOH, 96:4), triturated in hexane/CH$_2$Cl$_2$ and then isolated by filtration to afford the title compound as a white solid.

$^1$H NMR (500 MHz, CDCl$_3$): δ 9.88 (d, 1H), 9.06 (s, 1H), 8.79 (dd, 1H), 8.69 (dd, 1H), 7.70 (d, 1H), 7.60–7.52 (m, 3H), 7.49 (d, 1H), 7.44 (dd, 1H), 7.39–7.30 (m, 3H), 2.95 (m, 1H), 1.65 (m, 2H), 1.25 (m, 2H), 0.82 (m, 2H), 0.65 (m, 2H).

EXAMPLE 11

1-Cyano-3-{3'-[3-[(cyclopropylamino)carbonyl]-4-oxo-1,8-naphthyridin-1(4H)-yl]-1,1'-biphenyl-4-yl}-2,2-dimethylcyclopropanecarboxylic acid

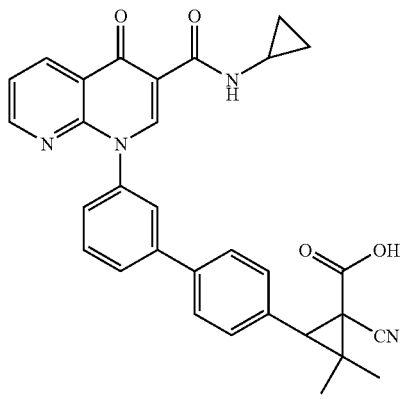

Step 1: tert-Butyl (2E)-3-(4-bromophenyl)-2-cyanoprop-2-enoate

A mixture of 4-bromobenzaldehyde (1 eq), t-butyl cyanoacetate (1 eq) and NH$_4$OAc (1 eq) in benzene (1M) was reflux for 4 h while removing water with a Dean-Stark trap. The mixture was cooled to rt, diluted with hexane and triturated. The title compound was isolated after filtration as a white solid.

Step 2: tert-Butyl 3-(4-bromophenyl)-1-cyano-2,2-dimethylcyclopropanecarboxylate Following a procedure described in Tetrahedron Lett. 1985, 1923, a mixture of 2-nitropropane (1 eq), K$_2$CO$_3$ (1 eq) and ester from step 1 (1 eq) in EtOH (1.2M) was stirred at 100° C. in a close bottle for 3 h. The mixture was cooled to rt, diluted with EtOAc, washed with a NH$_4$Cl sol., brine, dried over MgSO$_4$, filtered and concentrated. Flash chromatography (hexane:EtOAc, 95:5) afforded the title compound as oil.

Step 3: tert-Butyl 1-cyano-3-{3'-[3-[(cyclopropylamino)carbonyl]-4-oxo-1,8-naphthyridin-1(4H)-yl]-1,1'-biphenyl-4-yl}-2,2-dimethylcyclopropanecarboxylate Prepared according to the procedure described in EXAMPLE 7, step 3, but using ester from step 2. The residue was purified by flash chromatography (hexane:EtOAc, 60:40 to 30:70).

Step 4: 1-Cyano-3-{3'-[3-[(cyclopropylamino)carbonyl]-4-oxo-1,8-naphthyridin-1(4H)-yl]-1,1'-biphenyl-4-yl}-2,2-dimethylcyclopropanecarboxylic acid The ester from step 3 (1 eq) in CH$_2$Cl$_2$-TFA-DMS (3:2:1, 0.2M) was stirred at rt for 48 h. The volatiles were evaporated, the residue triturated in ether and then isolated by filtration to afford the title compound as a white solid.

$^1$H NMR (500 MHz, acetone-d$_6$): δ 9.73 (s, 1H), 8.94 (s, 1H), 8.77 (dd, 1H), 8.72 (dd, 1H), 8.01 (t, 1H), 7.92 (d, 1H), 7.81 (d, 2H), 7.73 (t, 1H), 7.64 (dd, 1H), 7.59 (dd, 1H), 7.51 (d, 2H), 2.93 (m, 1H), 2.9 (br s, OH), 1.52 (s, 3H), 1.36 (s, 3H), 0.78 (m, 2H), 0.58 (m, 2H).

EXAMPLE 12

2-{3'-[3-[(Cyclopropylamino)carbonyl]-4-oxo-1,8-naphthyridin-1(4H)-yl]-3-fluoro-1,1'-biphenyl-4-yl}cyclopropanecarboxylic acid

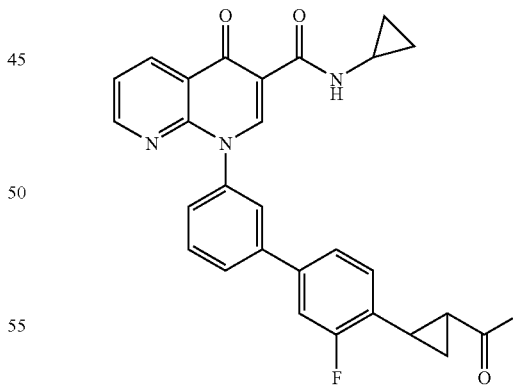

Step 1: Methyl 2-(4-bromo-2-fluorophenyl)cyclopropanecarboxylate

To a mixture of 4-bromo-2-fluorocinnamic acid and Pd(OAc)$_2$ (0.05 eq) in methylene chloride (1M) at 0° C. was added dropwise a solution of CH$_2$N$_2$ in ether until the reaction was completed by NMR analysis. The residue was purified by flash chromatography (hexane:EtOAc, 100:0 to 70:30).

Step 2: Methyl 2-{3'-[3-[(cyclopropylamino)carbonyl]-4-oxo-1,8-naphthyridin-1(4H)-yl]-3-fluoro-1,1'-biphenyl-4-yl}cyclopropanecarboxylate A mixture of NAPHTHYRIDINONE 3 (1.0 eq), ester from step 1 (1.3 eq), Na$_2$CO$_3$ (3.5 eq; 2M in H$_2$O), Pd(OAc)$_2$ (0.05 eq) and PPh$_3$ (0.15 eq) or PdCl$_2$dppf (0.05 eq) in n-propanol (0.1M) was stirred at 60–80° C. for 1–3 h. The mixture was cooled to rt, poured in water and extracted with EtOAc (2×). The combined organic extracts were washed with brine, dried over Na$_2$SO$_4$, filtered and concentrated. Flash chromatography (CH$_2$Cl$_2$:EtOAc; 90:10) afforded the title compound.

Step 3: 2-(trans)-{3'-[3-[(Cyclopropylamino)carbonyl]-4-oxo-1,8-naphthyridin-1(4H)-yl]-3-fluoro-1,1'-biphenyl-4-yl}cyclopropanecarboxylic acid To a solution of ester from above step 2 in THF-MeOH (2:1, 0.2M) was added LiOH (5 eq, 2M) and the mixture was stirred at rt for 6 h. The organic solvent evaporated, aqueous was acidified with AcOH and the acid extracted with EtOAc (3×). The organic was washed with brine, dried and solvent evaporated. The residue was triturated in CH$_2$Cl$_2$/ether and then isolated by filtration to afford the title compound as a solid.

$^1$H NMR (500 MHz, CDCl$_3$): δ 9.85 (d, 1H), 9.08 (s, 1H), 8.80 (dd, 1H), 8.70 (dd, 1H), 7.71 (d, 1H), 7.63 (t, 1H), 7.60 (s, 1H), 7.46 (dd, 1H), 7.40 (d, 1H), 7.28 (m, 2H), 7.01 (t, 1H), 2.97 (m, 1H), 2.66 (m, 1H), 1.93 (m, 1H), 1.62 (m, 1H), 1.40 (m, 1H), 0.84 (m, 2H), 0.66 (m, 2H).

Optically active (+) or (−)-(trans)-2-{3'-[3-[(cyclopropylamino)carbonyl]-4-oxo-1,8-naphthyridin-1(4H)-yl]-3-fluoro-1,1'-biphenyl-4-yl}cyclopropanecarboxylic acid was obtained using optically active (+) or (−)-(trans)-methyl 2-(4-bromo-2-fluorophenyl)cyclopropanecarboxylate prepared according to procedure described in EXAMPLE 29, step 5 to step 8.

EXAMPLE 13

(cis)-2-{3'-[3-[(Cyclopropylamino)carbonyl]-4-oxo-1,8-naphthyridin-1(4H)-yl]-1,1'-biphenyl-3-yl}cyclopropanecarboxylic acid

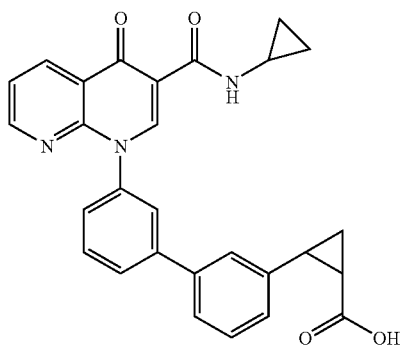

Prepared according to the procedure described in EXAMPLE 8, but using 3-bromobenzaldehyde as starting material.

$^1$H NMR (500 MHz, acetone-d$_6$): δ 9.78 (br s, 1H), 8.96 (s, 1H), 8.79 (d, 1H), 8.76 (d, 1H), 7.97 (s, 1H), 7.91 (d, 1H), 7.75 (t, 1H), 7.7 (s, 1H), 7.59–7.65 (m, 3H), 7.34–7.40 (m, 2H), 2.69 (dd, 1H), 2.12–2.15 (m, 1H), 1.67 (dd, 1H), 1.35–1.39 (m, 1H), 0.79–0.83 (m, 2H), 0.61 (br s, 2H).

EXAMPLE 14

2-{3'-Bromo-5'-[3-[(cyclopropylamino)carbonyl]-4-oxo-1,8-naphthyridin-1(4H)-yl]-1,1'-biphenyl-4-yl}cyclopropanecarboxylic acid

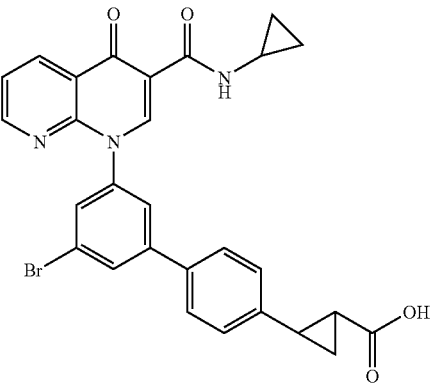

Step 1: N-Cyclopropyl-1-(3,5-dibromophenyl)-4-oxo-1,4-dihydro-1,8-naphthyridine-3-carboxamide Prepared according to the procedure described in NAPHTHYRIDINONE 2 but using 3,5-dibromoaniline as starting material.

Step 2: Ethyl 2-[4-(trimethylstannyl)phenyl]cyclopropanecarboxylate

A mixture of ethyl 2-(trans)-(4-bromophenyl)cyclopropanecarboxylate from EXAMPLE 1 step 1, hexamethylditin (3.5 eq) in 1,4-dioxane (0.2M) was stirred at 60° C. for 18 h, solvent evaporated and the residue purified by flash chromatography (hexane:EtOAc; 95:5) to afford the title compound.

Step 3: Ethyl 2-{3'-bromo-5'-[3-[(cyclopropylamino)carbonyl]-4-oxo-1,8-naphthyridin-1(4H)-yl]-1,1'-biphenyl-4-yl}cyclopropanecarboxylate A mixture of ester from step 2 (1.7 eq), dibromo from step 1 (1 eq), Pd$_2$(dba)3 (0.05 eq) and triphenylarsine (0.25 eq) in DMF (0.05M) was heated at 80° C. for 2 h. The mixture was cooled to rt, diluted with EtOAc and water, the organic was washed with brine, dried and solvent evaporated. The residue was purified by flash chromatography (CH$_2$Cl$_2$:MeOH; 99:1 to 90:10) to afford the title compound.

Step 4: 2-(trans)-{3'-Bromo-5'-[3-[(cyclopropylamino)carbonyl]-4-oxo-1,8-naphthyridin-1 (4H)-yl]-1,1'-biphenyl-4-yl}cyclopropanecarboxylic acid To a solution of ester from above step 3 in THF-MeOH—H$_2$O (2:1:0.5, 0.1M) was added LiOH (5 eq, 2M) and the mixture was stirred at 50° C. for 4 h. The organic solvent evaporated, aqueous was acidified with AcOH and the acid extracted with EtOAc (3×). The organic was washed with brine and solvent evaporated. The residue was purified by flash chromatography (CH$_2$Cl$_2$:MeOH; 99:1 to 90:10) to afford the title compound.

$^1$H NMR (500 MHz, DMSO-d$_6$): δ 9.71 (d, 1H), 8.84 (s, 1H), 8.80 (dd, 1H), 8.72 (dd, 1H), 8.08 (s, 1H), 8.01 (s, 1H), 7.91 (s, 1H), 7.71 (d, 2H), 7.65 (dd, 1H), 7.29 (d, 2H), 2.91–2.89 (m, 1H), 2.46–2.43 (m, 1H), 1.88–1.85 (m, 1H), 1.47–1.45 (m, 1H), 1.43–1.38 (m, 1H), 0.81–0.77 (m, 2H), 0.57–0.56 (m, 2H).

Optically active precursors are obtained by separation on chiral column (Chiral Pak AD) eluting with hexane:EtOH (35:65) containing 0.2% TFA.

EXAMPLE 15

2-{3'-[3-[(Cyclopropylamino)carbonyl]-4-oxo-1,8-naphthyridin-1(4H)-yl]-3-methyl-1,1'-biphenyl-4-yl}cyclopropanecarboxylic acid

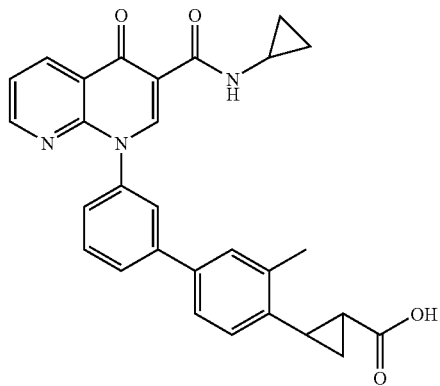

Step 1: Ethyl (2E)-3-(4-bromo-2-methylphenyl)prop-2-enoate

To a solution of 4-bromo-2-methylbenzaldehyde (1 eq) and triethylphosphonoacetate (1.1 eq) in THF (0.3M) at rt was added dropwise potassium t-butoxide (1.1 eq, 1M, THF). The mixture was stirred at rt 3 h, quenched with HCl 10%, diluted with ether, washed with a NaHCO$_3$ Solution, brine, dried over MgSO$_4$, filtered and concentrated. Flash chromatography (Hexane:EtOAc; 90:10 to 70:30) afforded the title compound.

Step 2: 2-(trans)-{3'-[3-[(Cyclopropylamino)carbonyl]-4-oxo-1,8-naphthyridin-1(4H)-yl]-3'-methyl-1,1'-biphenyl-4-yl}cyclopropanecarboxylic acid Prepared according to the procedure described in EXAMPLE 12, but using ester from step 1 as starting material.

$^1$H NMR (500 MHz, CDCl$_3$): δ 9.82 (d, 1H), 9.10 (s, 1H), 8.80 (dd, 1H), 8.70 (dd, 1H), 7.60 (m, 1H), 7.48 (m, 2H), 7.40 (m, 2H), 7.22 (d, 1H), 7.02 (s, 1H), 6.97 (m, 1H), 2.98 (m, 1H), 2.55 (m, 1H), 2.30 (s, 3H), 1.95 (m, 1H), 1.65 (m, 1H), 1.40 (m, 1H), 0.85 (m, 2H), 0.65 (m, 2H).

EXAMPLE 16

2-{3'-[3-[(Cyclopropylamino)carbonyl]-4-oxo-1,8-naphthyridin-1(4H)-yl]-2-methyl-1,1'-biphenyl-4-yl}cyclopropanecarboxylic acid

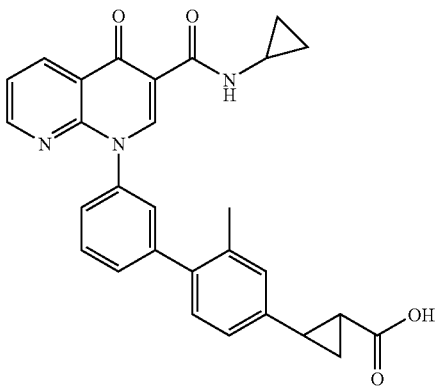

Prepared according to the procedure described in EXAMPLE 15, but using 4-bromo-3-methylbenzaldehyde as starting material.

Results in the title compound 2-(trans)-{3'-[3-[(Cyclopropylamino)carbonyl]-4-oxo-1,8-naphthyridin-1(4H)-yl]-2-methyl-1,1'-biphenyl-4-yl}cyclopropanecarboxylic acid.

$^1$H NMR (500 MHz, CDCl$_3$): δ 9.88 (s, 1H), 9.10 (s, 1H), 8.80 (d, 1H), 8.70 (d, 1H), 7.72 (d, 1H), 7.60 (m, 2H), 7.45 (dd, 1H), 7.40 (m, 3H), 7.05 (d, 1H), 2.98 (m, 1H), 2.55 (m, 1H), 2.45 (s, 3H), 1.78 (m, 1H), 1.60 (m, 1H), 1.40 (m, 1H), 0.85 (m, 2H), 0.75 (m, 2H).

EXAMPLE 17

2-{3-Chloro-3'-[3-[(cyclopropylamino)carbonyl]-4-oxo-1,8-naphthyridin-1(4H)-yl]1,1'-biphenyl-4-yl}cyclopropanecarboxylic acid

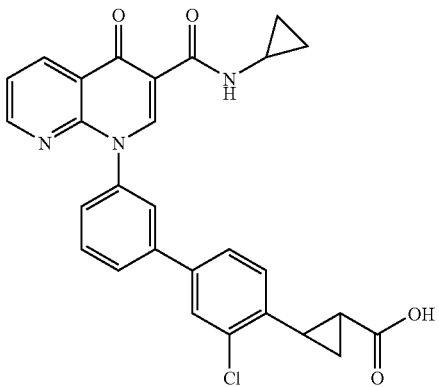

Prepared according to the procedure described in EXAMPLE 15, but using 4-bromo-2-chlorobenzaldehyde as starting material.

$^1$H NMR (500 MHz, CDCl$_3$): δ 9.88 (s, 1H), 9.10 (s, 1H), 8.80 (d, 1H), 8.70 (d, 1H), 7.72 (d, 1H), 7.65 (m, 3H), 7.45 (m, 3H), 7.05 (d, 1H), 2.95 (m, 1H), 2.70 (m, 1H), 1.80 (m, 1H), 1.65 (m, 1H), 1.35 (m, 1H), 0.85 (m, 2H), 0.65 (m, 2H).

Results in the title compound 2-(trans)-{3-Chloro-3'-[3-[(cyclopropylamino)carbonyl]-4-oxo-1,8-naphthyridin-1(4H)-yl]-1,1'-biphenyl-4-yl}cyclopropanecarboxylic acid.

EXAMPLE 18

2-(cis)-{3'-[3-[(Cyclopropylamino)carbonyl]-4-oxo-1,8-naphthyridin-1(4H)-yl]-3-fluoro-1,1'-biphenyl-4-yl}cyclopropanecarboxylic acid

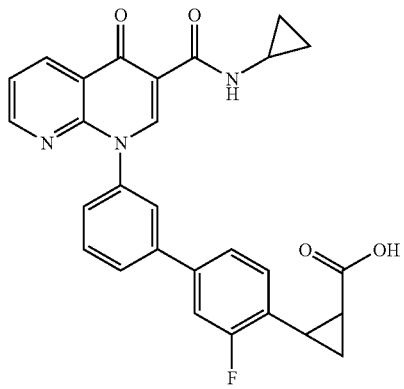

Prepared according to the procedure described in EXAMPLE 8, but using 4-bromo-2-fluorobenzaldehyde as starting material.

$^1$H NMR (500 MHz, DMSO-d$_6$): δ 11.91 (br s, 1H), 9.75 (d, 1H), 8.83 (s, 1H), 8.79 (dd, 1H), 8.74 (dd, 1H), 8.02 (s, 1H), 7.93 (d, 1H), 7.70 (t, 1H), 7.62–7.66 (m, 2H), 7.57 (d, 1H), 7.54 (d, 1H), 7.36 (t, 1H), 2.88–2.94 (m, 1H), 2.55 (q, 1H), 2.08–2.13 (m, 1H), 1.53 (dd, 1H), 1.36–1.40 (m, 1H), 0.77–0.81 (m, 2H), 0.56–0.59 (m, 2H).

EXAMPLE 19

3'-[3-[(Cyclopropylamino)carbonyl]-4-oxo-1,8-naphthyridin-1(4H)-yl]-1,1'-biphenyl-4-carboxylic acid

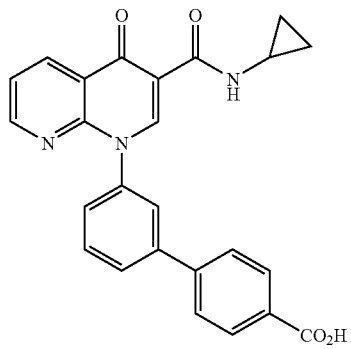

Step 1: Ethyl 3'-[3-[(cyclopropylamino)carbonyl]-4-oxo-1,8-naphthyridin-1(4H)-yl]-1,1'-biphenyl-4-carboxylate A mixture of NAPHTHYRIDINONE 3 (1 eq), ethyl 4-bromobenzoate (3 eq), Na$_2$CO$_3$ (3.5 eq.; 2M in H$_2$O), Pd(PPh$_3$)$_4$ (0.15 eq.) in n-propanol-DMF (1:1, 0.1M) was stirred at 80° C. for 2 h. The mixture was cooled to rt, quenched with brine and diluted with EtOAc. The organic extracts were washed with brine, dried over Na$_2$SO$_4$, filtered and concentrated. The residue was triturated in ether/EtOAc and then isolated by filtration to afford the title compound as a white solid.

Step 2: 3'-[3-[(Cyclopropylamino)carbonyl]-4-oxo-1,8-naphthyridin-1(4H)-yl]-1,1'-biphenyl-4-carboxylic acid To a solution of ester from above step 2 in THF-MeOH—CH$_2$Cl$_2$ (2:2:0.5, 0.2M) was added LiOH (5 eq, 2M) and the mixture was stirred at rt for 6 h. The organic solvent evaporated, aqueous was acidified with HCl 1N and the acid extracted with EtOAc (3×). The organic was washed with brine, dried and solvent evaporated. Flash chromatography (CH$_2$Cl$_2$:MeOH; 80:20 with NH$_3$) afforded the title compound.

$^1$H NMR (500 MHz, DMSO-d$_6$): δ 11.2 (s, OH), 9.75 (s, NH), 8.77 (dd, 1H), 8.73 (dd, 1H), 8.13 (d, 2H), 8.07 (s, 1H), 7.98 (d, 1H), 7.91 (d, 2H), 7.77 (t, 2H), 7.70 (d, 1H), 7.60 (dd, 1H), 2.94 (m, 1H), 0.78 (m, 2H), 0.57 (m, 2H). MS +ESI Q1 (M+1) 426.2

EXAMPLE 20

2-{3'-[3-(Morpholin-4-ylcarbonyl)-4-oxo-1,8-naphthyridin-1(4H)-yl]-1,1'-biphenyl-4-yl}cyclopropanecarboxylic acid

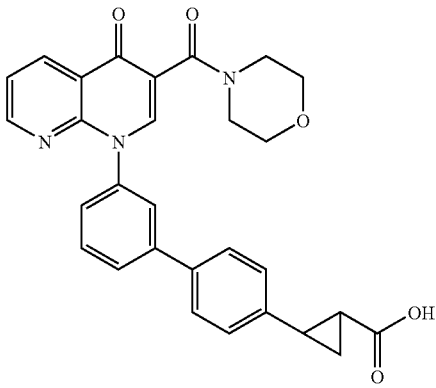

Step 1: 1-(3-Bromophenyl)-3-(morpholin-4-ylcarbonyl)-1,8-naphthyridin-4(1H)-one

A solution of acid from NAPHTHYRIDINONE 1, step 3 (1 eq) in THF (0.1M) was added oxalyl chloride (1.5 eq) and 2 drops of DMF. The mixture was heated to reflux for 1 h, cooled to rt and transferred into a solution of morpholine (3 eq, deprotonated with NaH in THF at 0° C.). The mixture was stirred at it for 18 h, quenched with a solution of NH$_4$Cl and diluted with EtOAc. The organic was washed with brine, dried and solvent evaporated. The residue was triturated in ether/EtOAc and then isolated by filtration to afford the title.

Step 2: Ethyl 2-[4-(4,4,5,5-tetramethyl-1,3,2-dioxaborolan-2-yl)phenyl]cyclopropanecarboxylate Prepared according to the procedure described in NAPHTHYRIDINONE 3, but using ethyl 2-(trans)-(4-bromophenyl)cyclopropanecarboxylate from EXAMPLE 1, step 1, as starting material.

Step 3: 2-[4-(4,4,5,5-Tetramethyl-1,3,2-dioxaborolan-2-yl)phenyl]cyclopropanecarboxylic acid To a solution of ester from step 2 in THF-H₂O (0.2M) was added LiOH (3 eq, 2M) and the mixture was stirred at it for 18 h. The organic solvent evaporated, aqueous was acidified with HCl 1N and the acid extracted with EtOAc (3×). The organic was washed with brine, dried and solvent evaporated to afford the title carboxylic acid.

Step 4: 2-(trans)-{3'-[3-(Morpholin-4-ylcarbonyl)-4-oxo-1,8-naphthyridin-1(4H)-yl]-1,1'-biphenyl-4-yl}cyclopropanecarboxylic acid A mixture of acid from step 2 (1 eq), amide from step 1 (1 eq), Na₂CO₃ (3.5 eq.; 2M in H₂O), Pd(PPh₃)₄ (0.15 eq.) in n-propanol-DMF (1:1, 0.1M) was stirred at 80° C. for 2 h. The mixture was cooled to rt, quenched with brine and diluted with EtOAc. The organic extracts were washed with brine, dried over Na₂SO₄, filtered and concentrated. The residue was purified by flash chromatography (CHCl₃:THF; 50:50), triturated in ether/acetone and then isolated by filtration to afford the title compound as a solid.

¹H NMR (500 MHz, CDCl₃): δ 10.5 (s, NH), 8.80 (dd, 1H), 8.71 (dd, 1H), 8.37 (s, 1H), 7.73 (d, 1H), 7.68 (s, 1H), 7.63 (t, 1H), 7.55 (d, 2H), 7.45 (m, 2H), 7.17 (d, 2H), 3.83 (br s, 6H), 3.53 (br s, 2H), 2.59 (m, 1H), 1.93 (m, 1H), 1.65 (m, 1H), 1.38 (m, 1H). MS +ESI Q1 (M+1) 496.1

EXAMPLE 21

2-{3'-[4-Oxo-3-({[5-(trifluoromethyl)-1,3,4-thiadiazol-2-yl]amino}carbonyl)-1,8-naphthyridin-1(4H)-yl]-1,1'-biphenyl-4-yl}cyclopropanecarboxylic acid

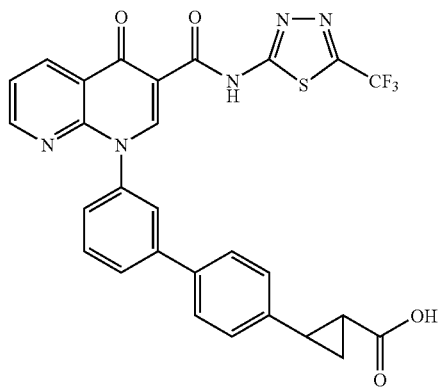

Step 1: 1-(3-Bromophenyl)-4-oxo-N-[5-(trifluoromethyl)-1,3,4-thiadiazol-2-yl]-1,4-dihydro-1,8-naphthyridine-3-carboxamide A solution of acid from NAPHTHYRIDINONE 1, step 3 (1 eq) in DMF (0.1M) was added HATU (4 eq), diisopropylethylamine (8 eq) followed by 5-(trifluoromethyl)-1,3,4-thiadiazol-2-amine (4 eq). The mixture was stirred at rt for 12 h then heated at 80° C. for 2 h, cooled to rt and diluted with water. The residue then isolated by filtration washed with ether, triturated in acetone to afford the title compound.

Step 2: 2-(trans)-{3'-[4-Oxo-3-({[5-(trifluoromethyl)-1,3,4-thiadiazol-2-yl]amino}carbonyl)-1,8-naphthyridin-1(4H)-yl]-1,1'-biphenyl-4-yl}cyclopropanecarboxylic acid Prepared according to the procedure described in EXAMPLE 20, step 2, 3 and 4, but using amide from step 1 as starting material. Purified by flash chromatography (CHCl₃:MeOH; 80:20 with NH₃).

¹H NMR (500 MHz, DMSO-d₆): δ 13.8 (s, OH), 9.95 (s, NH), 9.10 (s, 1H), 8.83 (m, 2H), 7.98 (s, 1H), 7.88 (d, 1H), 7.71 (d, 2H), 7.69 (m, 2H), 7.64 (d, 1H), 7.28 (d, 2H), 2.43 (m, 1H), 1.86 (m, 1H), 1.46 (m, 1H), 1.38 (m, 1H). MS +ESI Q1 (M+1) 578.2

EXAMPLE 22

2-{3'-[3-({[2-(Methylthio)ethyl]amino}carbonyl)-4-oxo-1,8-naphthyridin-1(4H)-yl]-1,1'-biphenyl-4-yl}cyclopropanecarboxylic acid

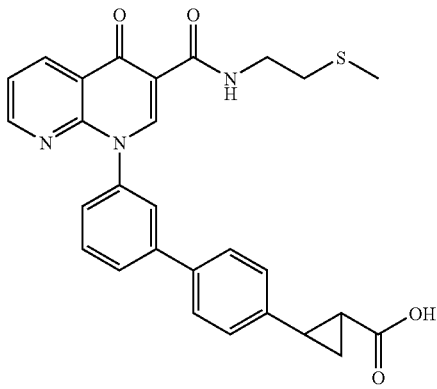

Step 1: 1-(3-Bromophenyl)-N-[2-(methylthio)ethyl]-4-oxo-1,4-dihydro-1,8-naphthyridine-3-carboxamide Prepared according to the procedure described in EXAMPLE 21, step 1, but using 2-(methylthio)ethanamine as starting material.

Step 2: Ethyl 2-{3'-[3-({[2-(methylthio)ethyl]amino}carbonyl)-4-oxo-1,8-naphthyridin-1(4H)-yl]-1,1'-biphenyl-4-yl}cyclopropanecarboxylate A mixture of amide from step 1 (1 eq), ethyl 2-(trans)-(4-bromophenyl)cyclopropanecarboxylate from EXAMPLE 1, step 1 (1 eq), Na₂CO₃ (3.5 eq.; 2M in H₂O), Pd(PPh₃)₄ (0.05 eq) in n-propanol (0.1M) was stirred at 80° C. for 3 h. The mixture was cooled to rt, quenched with brine and diluted with EtOAc. The organic extracts were washed with brine, dried over Na₂SO₄, filtered and concentrated. The residue was triturated in ether/MeOH, isolated by filtration and washed with ether to afford the title compound as a solid.

Step 3: 2-(trans)-{3'-[3-({[2-(Methylthio)ethyl]amino}carbonyl)-4-oxo-1,8-naphthyridin-1(4H)-yl]-1,1'-biphenyl-4-yl}cyclopropanecarboxylic acid To a solution of ester from above step 2 in THF-MeOH—H₂O (2:1:0.5, 0.1M) was added LiOH (5 eq, 2M) and the mixture was stirred at rt for 18 h. The organic solvent evaporated, aqueous was acidified with HCl 1N and the acid extracted with EtOAc (3×). The organic was washed with brine, dried and solvent evaporated. The residue was triturated ether/MeOH and then isolated by filtration to afford the title compound as a solid.

¹H NMR (500 MHz, CDCl₃): δ 10.21 (s, OH), 9.16 (s, NH), 8.89 (dd, 1H), 8.76 (dd, 1H), 7.78 (d, 1H), 7.65 (t, 1H), 7.63 (s, 1H), 7.53 (d, 2H), 7.51 (dd, 1H), 7.43 (d, 1H), 7.20

(d, 2H), 3.76 (td, 2H), 2.82 (t, 2H), 2.60 (m, 1H), 2.21 (s, 3H), 1.96 (m, 1H), 1.66 (m, 1H), 1.42 (m, 1H). MS +ESI Q1 (M+1) 500.2

EXAMPLE 23

2-{3'-[3-({[2-(Methylsulfonyl)ethyl]amino}carbonyl)-4-oxo-1,8-naphthyridin-1(4H)-yl]-1,1'-biphenyl-4-yl}cyclopropanecarboxylic acid

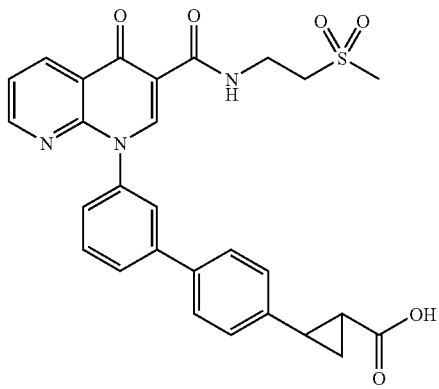

To a solution of EXAMPLE 22 (1 eq) in THF-MeOH—H$_2$O (2:1:1, 0.1M) was added Oxone (2 eq). The mixture was stirred at rt for 18 h and diluted with water. The residue was isolated by filtration, washed with ether to afford the title compound as a solid.

$^1$H NMR (500 MHz, DMSO-d$_6$): δ 12.4 (s, OH), 9.97 (s, NH), 8.83 (s, 1H), 8.78 (dd, 1H), 8.75 (dd, 1H), 7.95 (s, 1H), 7.87 (d, 1H), 7.66 (d, 2H), 7.64 (m, 2H), 7.59 (d, 1H), 7.28 (d, 2H), 3.82 (td, 2H), 3.42 (t, 2H), 3.05 (s, 3H), 2.44 (m, 1H), 1.87 (m, 1H), 1.46 (m, 1H), 1.40 (s, 1H). MS +ESI Q1 (M+1) 532.1.

Results in the title compound 2-(trans)-{3'-[3-({[2-(Methylsulfonyl)ethyl]amino}carbonyl)-4-oxo-1,8-naphthyridin-1(4H)-yl]-1,1'-biphenyl-4-yl}cyclopropanecarboxylic acid.

EXAMPLE 24

2-{3'-[4-Oxo-3-{[(2,2,2-trifluoroethyl)amino]carbonyl}-1,8-naphthyridin-1(4H)-yl]-1,1'-biphenyl-4-yl}cyclopropanecarboxylic acid

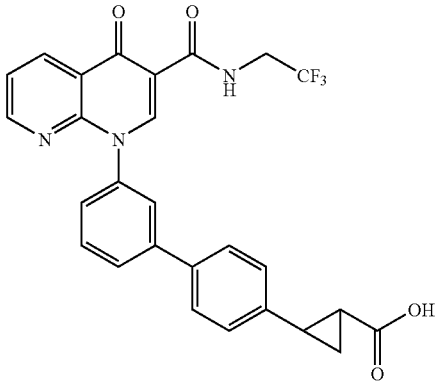

Prepared according to the procedure described in EXAMPLE 22, but using 2,2,2-trifluoroethanamine as starting material.

$^1$H NMR (500 MHz, CDCl$_3$): δ 11.3 (s, OH), 10.34 (s, NH), 9.11 (s, 1H), 8.88 (dd, 1H), 8.77 (dd, 1H), 7.78 (d, 1H), 7.68 (t, 1H), 7.65 (s, 1H), 7.56 (d, 2H), 7.52 (dd, 1H), 7.44 (dd, 1H), 7.22 (d, 2H), 4.21 (br qt, 2H), 2.62 (m, 1H), 1.97 (m, 1H), 1.70 (m, 1H), 1.45 (m, 1H). MS +ESI Q1 (M+1) 508.1.

Results in the title compound 2-(trans)-{3'-[4-Oxo-3-{[(2,2,2-trifluoroethyl)amino]carbonyl}-1,8-naphthyridin-1(4H)-yl]-1,1'-biphenyl-4-yl}cyclopropanecarboxylic acid.

EXAMPLE 25

2-(5-{3-[3-[(Cyclopropylamino)carbonyl]-4-oxo-1,8-naphthyridin-1(4H)-yl]phenyl}thien-2-yl)cyclopropanecarboxylic acid

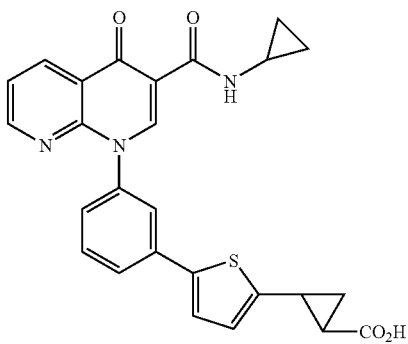

Prepared according to the procedure described in EXAMPLE 15, but 5-bromothiophene-2-carbaldehyde as starting material. $^1$H NMR (500 MHz, CDCl$_3$): δ 10.21 (s, OH), 9.77 (s, NH), 9.04 (s, 1H), 8.79 (dd, 1H), 8.69 (dd, 1H), 7.66 (d, 1H), 7.54 (m, 2H), 7.45 (dd, 1H), 7.28 (d, 1H), 7.13 (dd, 1H), 6.77 (dd, 1H), 2.97 (m, 1H), 2.68 (m, 1H), 1.93 (m, 1H), 1.65 (m, 1H), 1.36 (m, 1H), 0.83 (m, 2H), 0.66 (m, 2H). MS +ESI Q1 (M+1) 472.2.

Results in the title compound 2-(trans)-(5-{3-[3-[(Cyclopropylamino)carbonyl]-4-oxo-1,8-naphthyridin-1(4H)-yl]phenyl}thien-2-yl)cyclopropanecarboxylic acid.

EXAMPLE 26

2-{3'-[3-{[(Cyclopropylmethyl)amino]carbonyl}-4-oxo-1,8-naphthyridin-1(4H)-yl]-1,1'-biphenyl-4-yl}cyclopropanecarboxylic acid

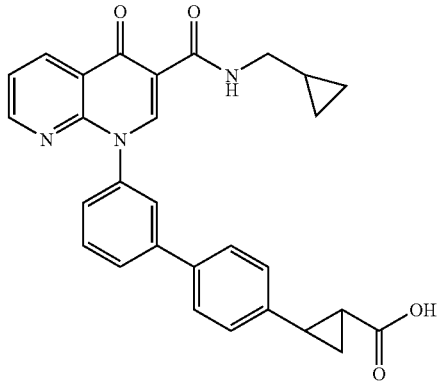

Prepared according to the procedure described in EXAMPLE 22, but using 1-cyclopropylmethanamine as starting material.

$^1$H NMR (500 MHz, DMSO-d$_6$): δ 9.83 (s, NH), 8.82 (s, 1H), 8.79 (dd, 1H), 8.75 (dd, 1H), 7.96 (s, 1H), 7.87 (d, 1H), 7.65 (m, 3H), 7.57 (d, 2H), 7.28 (d, 2H), 3.38 (t, 2H), 2.45 (m, 1H), 1.87 (m, 1H), 1.47 (m, 1H), 1.40 (m, 1H), 1.08 (m, 1H), 0.49 (m, 2H), 0.26 (m, 2H). MS +ESI Q1 (M+1) 480.1.

Results in the title compound 2-(trans)-{3'-[3-{[(Cyclopropylmethyl)amino]carbonyl}-4-oxo-1,8-naphthyridin-1(4H)-yl]1,1'-biphenyl-4-yl}cyclopropanecarboxylic acid.

EXAMPLE 27

2-{3'-[3-{[(1-Cyanocyclopropyl)amino]carbonyl}-4-oxo-1,8-naphthyridin-1(4H)-yl]-1,1'-biphenyl-4-yl}cyclopropanecarboxylic acid

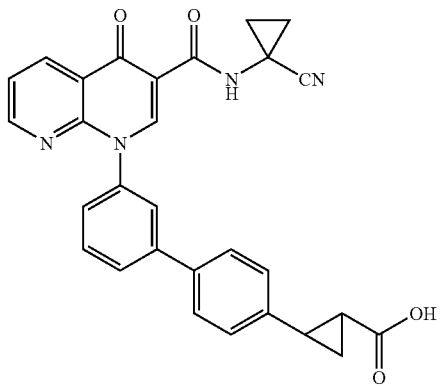

Prepared according to the procedure described in EXAMPLE 21, but using 1-aminocyclopropanecarbonitrile as starting material.

$^1$H NMR (500 MHz, CDCl$_3$): δ 11.51 (s, OH), 10.36 (s, NH), 9.11 (s, 1H), 8.84 (dd, 1H), 8.76 (dd, 1H), 7.78 (d, 1H), 7.67 (t, 1H), 7.63 (s, 1H), 7.57 (d, 2H), 7.53 (dd, 1H), 7.41 (d, 1H), 7.22 (d, 2H), 2.67 (m, 1H), 1.98 (m, 1H), 1.74 (m, 1H), 1.66 (m, 2H), 1.45 (m, 1H), 1.40 (m, 2H). MS +ESI Q1 (M+1) 519.2.

Results in the title compound 2-(trans)-{3'-[3-{[(1-Cyanocyclopropyl)amino]carbonyl}-4-oxo-1,8-naphthyridin-1(4H)-yl]-1,1'-biphenyl-4-yl}cyclopropanecarboxylic acid.

EXAMPLE 28

3-{3'-[3-[(Isopropylamino)carbonyl]-4-oxo-1,8-naphthyridin-1(4H)-yl]-1,1'-biphenyl-4-yl}-3-methylbutanoic acid

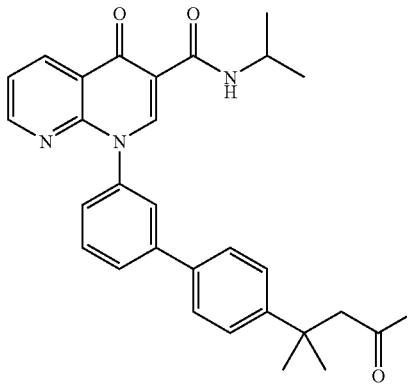

Prepared according to the procedure described in EXAMPLE 5 but using NAPHTHYRIDINONE 4 as starting material.

$^1$H NMR (500 MHz, CDCl$_3$): δ 9.76 (d, 1H), 9.11 (s, 1H), 8.85 (d, 1H), 8.73 (d, 1H), 7.77 (d, 1H), 7.65 (m, 2H), 7.58 (d, 2H), 7.47 (m, 3H), 7.41 (d, 1H), 4.33 (m, 1H), 2.71 (s, 2H), 1.51 (s, 6H), 1.33 (dd, 6H).

EXAMPLE 29

(+)-(trans)-2-{3-fluoro-3'-[4-oxo-3-{[(2,2,2-trifluoroethyl)amino]carbonyl}-1,8-naphthyridin-1(4H)-yl]biphenyl-4-yl}cyclopropanecarboxylic acid

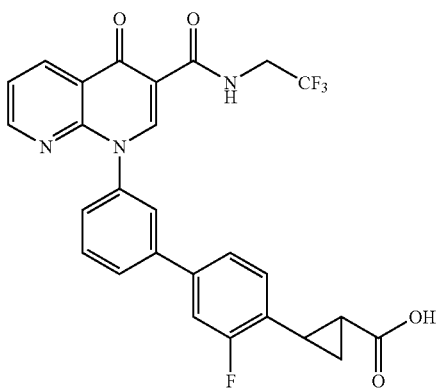

Step 1: Ethyl 1-(3-bromophenyl)-1,4-dihydro[1,8]naphthyridin-4-one-3-carboxylate A mixture of ethyl 2-chloronicotinoyl acetate (purchased or prepared following a procedure described in J. Het. Chem., 30, 855, 1993) (1 eq), triethylamine (4 eq) and ethyl 3,3-dimethylaminoacrylate (1.5 eq) in acetonitrile (0.5M) was heated to reflux for 3 h, cooled to 40–50° C. and 3-bromoaniline (1 eq) was added. The reaction was heated to reflux overnight, cooled to rt, diluted with water (2 volume). The product was isolated by filtration and washed with water, ether or acetonitrile-water (1:1).

$^1$H NMR (Acetone-$d_6$) δ 1.32 (t, 3H), 4.29 (q, 2H), 7.54–7.63 (m, 2H), 7.69 (dd, 1H), 7.78 (dd, 1H), 7.93 (s, 1H), 8.66–8.71 (m, 3H).

Step 2: 1-(3-Bromophenyl)-1,4-dihydro[1,8]naphthyridin-4-one-3-carboxylic acid

A suspension of ethyl 1-(3-bromophenyl)-1,4-dihydro[1,8]naphthyridin-4-one-3-carboxylate from Step 1 (1 eq) in a mixture of tetrahydrofuran-methanol (0.15M) and 1N aqueous sodium hydroxide (2 eq) was heated at ca 50° C. with stirring for 20 minutes. After cooling, the mixture was diluted with water and acidified with 1N aqueous HCl. After stirring for 45 minutes, the precipitate was filtered, washed well with water and dried to afford the title acid as a cream-colored solid.

$^1$H NMR (Acetone-$d_6$) δ 7.65 (t, 1H), 7.76 (m, 2H), 7.84 (d, 1H), 7.99 (s, 1H), 8.87 (m, 2H), 9.01 (s, 1H).

Step 3: 1-(3-bromophenyl)-N-(2,2,2-trifluoroethyl)-1,4-dihydro-1,8-naphthyridin-4-one-3-carboxamide To a suspension of 1-(3-bromophenyl)-1,4-dihydro[1,8]naphthyridin-4-one-3-carboxylic acid from Step 2 (0.1 eq) and triethylamine (3 eq) in tetrahydrofuran (0.08M) at 0° C. was added isobutyl chloroformate (1.8 eq). After stirring at 0° C. for 2 hours, 2,2,2-trifluoroethylamine (5 eq) was added and the mixture was allowed to warm up to room temperature and stirred overnight. The mixture was then partitioned between ethyl acetate and water, the organic phase was dried and evaporated to a solid which was stirred in ether at room temperature for 3 hours and filtered to afford the N-(2,2,2-trifluoroethyl)-1-(3-bromophenyl)-1,4-dihydro[1,8]naphthyridin-4-one-3-carboxamide as a white solid.

Alternatively:

A suspension of 1-(3-bromophenyl)-1,4-dihydro[1,8]naphthyridin-4-one-3-carboxylic acid from Step 2 (1 eq) in DMF (0.1M) was added HATU (4 eq), diisopropylethylamine (8 eq) followed by 2,2,2-trifluoroethylamine (4 eq). The mixture was stirred at rt for 12 h then heated at 80° C. for 2 h, cooled to it and diluted with water. The residue then isolated by filtration washed with ether, triturated in acetone to afford the title compound.

Step 4: N-(2,2,2-trifluoroethyl)-1-[3-(4,4,5,5-tetramethyl-1,3,2-dioxaborolan-2-yl)phenyl]-1,4-dihydro-1,8-naphthyridin-4-one-3-carboxamide A mixture of 1-(3-bromophenyl)-N-(2,2,2-trifluoroethyl)-1,4-dihydro-1,8-naphthyridin-4-one-3-carboxamide (1.0 eq), pinacol diborane (1.5 eq), KOAc (4 eq) and $PdCl_2$(dppf) (0.05 eq) in DMF (0.2M) was stirred at 70–80° C. for 3 h. The mixture was cooled to rt, diluted with EtOAc and a $NH_4$Cl solution. The organic extracts were washed with $H_2O$, brine, dried over $MgSO_4$, filtered and concentrated. Crystallization from EtOAc-Ether-Hexane (1:1:2) and flash chromatography ($CH_2Cl_2$:EtOAc, 50:50) of the mother liquor afforded the title compound as a white solid.

Step 5: 4-bromo-2-fluoro-1-vinylbenzene

To a suspension of methyltriphenylphosphonium bromide (1.1 eq) in tetrahydrofuran (0.13M) at −78° C., was added n-butyllithium (2.5M in hexanes, 1.1 eq) dropwise over 20 min. The reaction mixture was stirred at −78° C. for 15 min, warm to 0° C., stirred for 15 min and cooled back to −78° C. A solution of 4-bromo-2-fluoro-benzaldehyde (1 eq) in 100 mL THF was added dropwise over 30 min. Final mixture was allowed to warm slowly to rt and stirred for 1 h. The resulting mixture was quenched with a saturated $NH_4$Cl solution and diluted with 2 volume of hexane. The organic extract was washed with brine, dried over $MgSO_4$, filtered and concentrated. The residue was diluted with Hexane/EtOAc (9:1) and filtered on a pad of Silica gel. The fractions were combined and concentrated to afford the desired material.

Step 6: (+)-ethyl 2-(4-bromo-2-fluorophenyl)cyclopropanecarboxylate

To a suspension of copper(I) trifluoromethanesulfonate benzene complex (0.01 eq) in chloroform (100 mL) at rt, was added (R,R)-2,2'-isopropylidene-bis(4-tert-butyl-2-oxazoline) (0.01 eq). The mixture was stirred at for 1 h then cannulated through glass wool in a solution of styrene from step 5 (1.2 eq) in chloroform (0.1M) at 4° C. To this solution was added a solution of ethyl diazoacetate (0.8 eq) in of chloroform (1M) dropwise over 3 h. The final mixture was stirred overnight at 4° C. The mixture was concentrated. Flash chromatography (Hexane, EtOAc; 95:5) afforded the desired compound. (84:16, trans:cis isomers, methodology described in Evans et al. *J. Am. Chem. Soc.* 1991, 113, 726).

Step 7: (+)-2-(4-bromo-2-fluorophenyl)cyclopropanecarboxylic acid

To a solution of (+)-ethyl 2-(4-bromo-2-fluorophenyl)cyclopropanecarboxylate (mix esters, 1 eq) in tetrahydrofuran-methanol (2:1) was added lithium hydroxide (0.84 eq). The reaction was stirred at rt for 2 days. The resulting mixture was concentrated, diluted with water, extracted with ether(2×) to obtain the cis ester. The aqueous phase was acidified using HCl 10%, extracted with ether (2×) to obtain the (+)-trans acid. The organic extract containing the trans acid were combined and washed with brine, dried over $MgSO_4$, filtered and concentrated.

Step 8: (+)-methyl 2-(4-bromo-2-fluorophenyl)cyclopropanecarboxylate

To a solution of (+)-2-(4-bromo-2-fluorophenyl)cyclopropanecarboxylic acid from step 7 (1 eq) in methylenechloride was added an ethereal solution of diazomethane until reaction is completed by TLC. The resulting mixture was concentrated. The crude ester was used as such in the next step.

Step 9: (+)-methyl 2-{3-fluoro-3'-[4-oxo-3-{[(2,2,2-trifluoroethyl)amino]carbonyl}-1,8-naphthyridin-1(4H)-yl]biphenyl-4-yl}cyclopropanecarboxylate To a solution of (+)-methyl 2-(4-bromo-2-fluorophenyl) cyclopropanecarboxylate from step 8 (1.2 eq) and boronate ester from step 4 (1 eq) in DMF-iPrOH (1:1, 0.1M), was added tris(dibenzylideneacetone)dipalladium(0) (0.055 eq), 2-(dimethylamino)-2'-(dicyclohexylphosphino)biphenyl (0.13 eq) and a sodium carbonate solution (2M, 4 eq) The reaction mixture was heated at 78° C. for 2 h. The reaction mixture was filtered on Celite and silica gel (1:1) and washed with EtOAc. The filtrate was concentrated in vacuo and remaining solvents were distilled in vacuo. The resulting yellow solid is stirred vigourously in ether. The residue then isolated by filtration and washed with ether. Mother liquors were further purified by flash chromatography (toluene/EtOAc, 100:0 to 70:30).

Step 10: (+)-2-{3-fluoro-3'-[4-oxo-3-{[(2,2,2-trifluoroethyl)amino]carbonyl}-1,8-naphthyridin-1(4H)-yl]biphenyl-4-yl}cyclopropanecarboxylic acid To a solution of ester from step 9 in THF-MeOH—H$_2$O (7:3:1, 0.05M) was added LiOH (1.1 eq, 1M) and the mixture was stirred at 50° C. for 3 h, then at room temperature for 24 h. The organic solvent evaporated, aqueous was acidified with HCl 1N and the acid extracted with EtOAc (3×). The organic was washed with brine, dried and solvent evaporated to afford 2-(3-bromophenyl)cyclopropanecarboxylic acid. The resulting solid is stirred vigorously in hexane-ether-acetone for 1 h then collected by filtration.

The enantiomer: EXAMPLE 65, (−)-2-{3-fluoro-3'-[4-oxo-3-{[(2,2,2-trifluoroethyl)amino]carbonyl}-1,8-naphthyridin-1(4H)-yl]biphenyl-4-yl}cyclopropanecarboxylic acid can be obtained using (S,S)-2,2'-isopropylidene-bis(4-tert-butyl-2-oxazoline) in step 6.

$^1$H NMR (500 MHz, CDCl$_3$): δ 10.31 (s, NH), 9.10 (s, 1H), 8.9 (dd, 1H), 8.78 (m, 1H), 7.78 (dd, 1H), 7.71 (t, 1H), 7.64 (br s, 1H), 7.53 (m, 1H), 7.47 (dd, 1H), 7.35 (m, 2H), 7.09 (t, 1H), 4.16 (m, 2H), 3.77 (m, 1H), 2.00 (m, 1H), 1.71 (m, 1H), 1.52 (m, 1H). MS +ESI Q1 (M+1) 525.9

EXAMPLE 30

1-({3'-[3-[(cyclopropylamino)carbonyl]-4-oxo-1,8-naphthyridin-1(4H)-yl]biphenyl-4-yl}methyl)cyclobutanecarboxylic acid

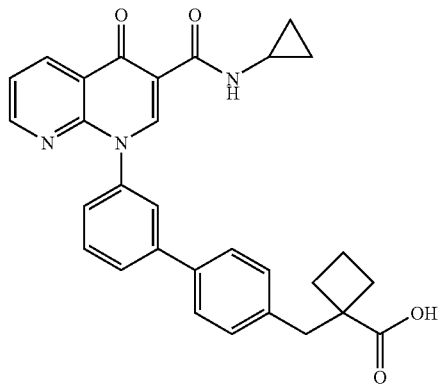

Step 1: ethyl 1-(4-bromobenzyl)cyclobutanecarboxylate

To a solution of LDA (1.2 eq) in THF at −78° C. was added ethyl cyclobutanecarboxylate (1 eq) and reaction mixture was warmed up to −40° C. for 10 min. The reaction was cooled back to −78° C. for 1 h, then 4-bromobenzyl bromide (1.1 eq) was added as a solid to the mixture. The reaction mixture was warmed to 0° C. in an ice bath. The reaction was quenched with a saturated solution of NH$_4$Cl and extract 3× with ethyl acetate, dried with MgSO$_4$ and evaporated to dryness. Flash chromatography with 95:5 hexanes:ethyl acetate afforded ethyl 1-(4-bromobenzyl)cyclobutanecarboxylate.

Step 2: ethyl 1-({3'-[3-[(cyclopropylamino)carbonyl]-4-oxo-1,8-naphthyridin-1(4H)-yl]biphenyl-4-yl}methyl)cyclobutanecarboxylate A mixture of NAPHTHYRIDINONE 3 (1.0 eq), ester from step 1 (1.5 eq), Na$_2$CO$_3$ (3.5 eq; 2M in H$_2$O), Pd(OAc)$_2$ (0.05 eq.) and PPh$_3$ (0.15 eq.) or PdCl$_2$dppf (0.05 eq) in n-propanol-DMF (1:1, 0.1M) was stirred at 70° C. for 2 h. The mixture was cooled to it, quenched with AcOH and diluted with EtOAc. The combined organic extracts were washed with brine, dried over Na$_2$SO$_4$, filtered and concentrated. Flash chromatography (CH$_2$Cl$_2$/MeOH, 99:1) afforded the title compound.

Step 3: 1-({3'-[3-[(cyclopropylamino)carbonyl]-4-oxo-1,8-naphthyridin-1(4H)-yl]biphenyl-4-yl}methyl)cyclobutanecarboxylic acid To a solution of ester from above step 2 in THF-MeOH—H$_2$O (2:1:0.5, 0.1M) was added LiOH (5 eq, 2M) and the mixture was stirred at 50° C. for 4 h. The organic solvent evaporated, aqueous was acidified with AcOH and the acid extracted with EtOAc (3×). The organic was washed with brine, dried and solvent evaporated. The residue was purified by flash chromatography (CH$_2$Cl$_2$/MeOH, 10% NH$_4$OH, 85:15) to afford the title compound as a white solid.

$^1$H NMR (500 MHz, acetone-d$_6$): δ 9.87 (s, NH), 9.1 (s, 1H), 8.84 (dd, 1H), 8.72 (dd, 1H), 7.72 (d, 1H), 7.61 (m, 2H), 7.49 (m, 3H), 7.39 (d, 1H), 7.27 (m, 1H), 3.18 (s, 2H), 3.05 (m, 1H), 2.5 (m, 2H), 2.12 (m, 2H), 1.95 (m, 2H), 0.90 (m, 2H), 0.70 (m, 2H). MS 492.0 (−)

The following compounds were prepared according to the procedures described previously. Indicated is their respective (M+1)$^+$ value obtained from a low resolution mass spectrometer under electron-spray or chemical ionization conditions. * indicate a (M−1)− value.

| EX. | Chemical name | LRMS (M + 1)$^+$ |
| --- | --- | --- |
| 31 | (trans)-2-{3'-[3-[(cyclopropylamino)carbonyl]-4-oxo-1,8-naphthyridin-1(4H)-yl]biphenyl-4-yl}-2-methylcyclopropanecarboxylic acid | 480.2 |
| 32 | (trans)-2-{3'-[3-[(cyclopropylamino)carbonyl]-4-oxo-1,8-naphthyridin-1(4H)-yl]biphenyl-2-yl}cyclopropanecarboxylic acid | 466.2 |
| 33 | 3-methyl-3-{3'-[4-oxo-3-{[(2,2,2-trifluoroethyl)amino]carbonyl}-1,8-naphthyridin-1(4H)-yl]biphenyl-4-yl}butanoic acid | 524.3 |
| 34 | (trans)-2-{3'-[4-oxo-3-{[(2,2,2-trifluoroethyl)amino]carbonyl}-1,8-naphthyridin-1(4H)-yl]biphenyl-2-yl}cyclopropanecarboxylic acid | 506.3* |
| 35 | (trans)-2-{3'-[4-oxo-3-{[(2,2,3,3,3-pentafluoropropyl)amino]carbonyl}-1,8-naphthyridin-1(4H)-yl]biphenyl-4-yl}cyclopropanecarboxylic acid | 588.0 |
| 36 | (trans)-2-{3'-[3-[(cyclopropylamino)carbonyl]-4-oxo-1,8-naphthyridin-1(4H)-yl]biphenyl-4-yl}-1-fluorocyclopropanecarboxylic acid | 482.2* |

-continued

| EX. | Chemical name | LRMS (M + 1)+ |
|---|---|---|
| 37 | (+)-(trans)-2-{3-chloro-3'-[3-[(cyclopropylamino)carbonyl]-4-oxo-1,8-naphthyridin-1(4H)-yl]biphenyl-4-yl}cyclopropanecarboxylic acid | 500.2 |
| 38 | (−)-(trans)-2-{3'-[4-oxo-3-{[(2,2,2-trifluoroethyl)amino]carbonyl}-1,8-naphthyridin-1(4H)-yl]biphenyl-4-yl}cyclopropanecarboxylic acid | 506.2* |
| 39 | (+)-(trans)-ethyl 2-{3'-[3-[(cyclopropylamino)carbonyl]-4-oxo-1,8-naphthyridin-1(4H)-yl]biphenyl-4-yl}cyclopropanecarboxylate | 494.3 |
| 40 | (+)-(trans)-isopropyl 2-{3'-[3-[(cyclopropylamino)carbonyl]-4-oxo-1,8-naphthyridin-1(4H)-yl]biphenyl-4-yl}cyclopropanecarboxylate | 508.5 |
| 41 | tert-butyl 3-{3'-[3-[(cyclopropylamino)carbonyl]-4-oxo-1,8-naphthyridin-1(4H)-yl]biphenyl-4-yl}-2,2-dimethylpropanoate | 538.5 |
| 42 | 3-{3'-[3-[(cyclopropylamino)carbonyl]-4-oxo-1,8-naphthyridin-1(4H)-yl]biphenyl-4-yl}-2,2-dimethylpropanoic acid | 482.2 |
| 43 | 3-{3'-[3-[(cyclopropylamino)carbonyl]-4-oxo-1,8-naphthyridin-1(4H)-yl]biphenyl-3-yl}-2,2-dimethylpropanoic acid | 482.2 |
| 44 | 1-({3'-[3-[(cyclopropylamino)carbonyl]-4-oxo-1,8-naphthyridin-1(4H)-yl]biphenyl-3-yl}methyl)cyclobutanecarboxylic acid | 494.3 |
| 45 | 3-{3'-[3-[(cyclopropylamino)carbonyl]-4-oxo-1,8-naphthyridin-1(4H)-yl]biphenyl-2-yl}-2,2-dimethylpropanoic acid | 482.2 |
| 46 | 1-({3'-[3-[(cyclopropylamino)carbonyl]-4-oxo-1,8-naphthyridin-1(4H)-yl]biphenyl-2-yl}methyl)cyclobutanecarboxylic acid | 494.4 |
| 47 | (+)-(trans)-2-{3'-[3-[(tert-butylamino)carbonyl]-4-oxo-1,8-naphthyridin-1(4H)-yl]biphenyl-4-yl}cyclopropanecarboxylic acid | 482.2 |
| 48 | (+)-(trans)-2-{3'-[3-[(cyclobutylamino)carbonyl]-4-oxo-1,8-naphthyridin-1(4H)-yl]biphenyl-4-yl}cyclopropanecarboxylic acid | 480.2 |
| 49 | 3-{3'-[3-[(cyclopropylamino)carbonyl]-4-oxo-1,8-naphthyridin-1(4H)-yl]biphenyl-4-yl}bicyclo[1.1.1]pentane-1-carboxylic acid | 492.2 |
| 50 | 4-{3'-[3-[(cyclopropylamino)carbonyl]-4-oxo-1,8-naphthyridin-1(4H)-yl]biphenyl-4-yl}-4-hydroxypentanoic acid | 498.1 |
| 51 | (trans)-2-{3'-[3-{[(±)-cis-(2-fluorocyclopropyl)amino]carbonyl}-4-oxo-1,8-naphthyridin-1(4H)-yl]-(+)-biphenyl-4-yl}cyclopropanecarboxylic acid | 484.3 |
| 52 | (+)-(trans)-2-{3'-[3-{[(dicyclopropylmethyl)amino]carbonyl}-4-oxo-1,8-naphthyridin-1(4H)-yl]biphenyl-4-yl}cyclopropanecarboxylic acid | 520.4 |
| 53 | 4-{3'-[3-[(cyclopropylamino)carbonyl]-4-oxo-1,8-naphthyridin-1(4H)-yl]biphenyl-4-yl}-2,2-dimethylbutanoic acid | 496.2 |
| 54 | (+)-(trans)-2-{3'-[3-{[(1-hydroxycyclopropyl)amino]carbonyl}-4-oxo-1,8-naphthyridin-1(4H)-yl]biphenyl-4-yl}cyclopropanecarboxylic acid | 482.0 |
| 55 | (+)-(trans)-2-{3'-[4-oxo-3-{[(1-phenylcyclopropyl)amino]carbonyl}-1,8-naphthyridin-1(4H)-yl]biphenyl-4-yl}cyclopropanecarboxylic acid | 542.3 |
| 56 | 4-{3'-[3-[(cyclopropylamino)carbonyl]-4-oxo-1,8-naphthyridin-1(4H)-yl]biphenyl-4-yl}-3,3-dimethylbutanoic acid | 496.2 |
| 57 | (+)-(trans)-2-{3'-[3-{[(1-cyclopropyl-1-methylethyl)amino]carbonyl}-4-oxo-1,8-naphthyridin-1(4H)-yl]biphenyl-4-yl}cyclopropanecarboxylic acid | 508.3 |
| 58 | 1-({3'-[4-oxo-3-{[(2,2,2-trifluoroethyl)amino]carbonyl}-1,8-naphthyridin-1(4H)-yl]biphenyl-4-yl}methyl)cyclobutanecarboxylic acid | 534.2* |
| 59 | (+)-(trans)-2-{3'-[3-{[(cyclopropylmethyl)amino]carbonyl}-4-oxo-1,8-naphthyridin-1(4H)-yl]biphenyl-4-yl}cyclopropanecarboxylic acid | 480.1 |
| 60 | (−)-(trans)-2-{3-fluoro-3'-[3-{[(1-hydroxycyclopropyl)amino]carbonyl}-4-oxo-1,8-naphthyridin-1(4H)-yl]biphenyl-4-yl}cyclopropanecarboxylic acid | 500.1 |
| 61 | (trans)-2-{3'-[4-oxo-3-{[((±)-2,2,2-trifluoro-1-methylethyl)amino]carbonyl}-1,8-naphthyridin-1(4H)-yl]-(+)-biphenyl-4-yl}cyclopropanecarboxylic acid | 522.4 |
| 62 | (+)-(trans)-2-{3'-[3-{[(1-methylcyclopropyl)amino]carbonyl}-4-oxo-1,8-naphthyridin-1(4H)-yl]biphenyl-4-yl}cyclopropanecarboxylic acid | 480.2 |
| 63 | 2,2-dimethyl-4-{3'-[4-oxo-3-{[(2,2,2-trifluoroethyl)amino]carbonyl}-1,8-naphthyridin-1(4H)-yl]biphenyl-4-yl}butanoic acid | 538.2 |
| 64 | 2,2-dimethyl-3-{3'-[4-oxo-3-{[(2,2,2-trifluoroethyl)amino]carbonyl}-1,8-naphthyridin-1(4H)-yl]biphenyl-4-yl}propanoic acid | 524.4 |
| 65 | (−)-(trans)-2-{3-fluoro-3'-[4-oxo-3-{[(2,2,2-trifluoroethyl)amino]carbonyl}-1,8-naphthyridin-1(4H)-yl]biphenyl-4-yl}cyclopropanecarboxylic acid | 525.9 |
| 66 | (−)-(trans)-2-{3-chloro-3'-[3-[(cyclopropylamino)carbonyl]-4-oxo-1,8-naphthyridin-1(4H)-yl]biphenyl-4-yl}cyclopropanecarboxylic acid | 500.2 |
| 67 | (+)-(trans)-2-{3'-[4-oxo-3-{[(2,2,2-trifluoroethyl)amino]carbonyl}-1,8-naphthyridin-1(4H)-yl]biphenyl-4-yl}cyclopropanecarboxylic acid | 506.1* |

29 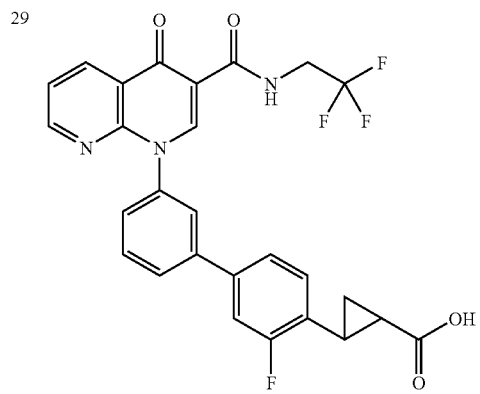
30 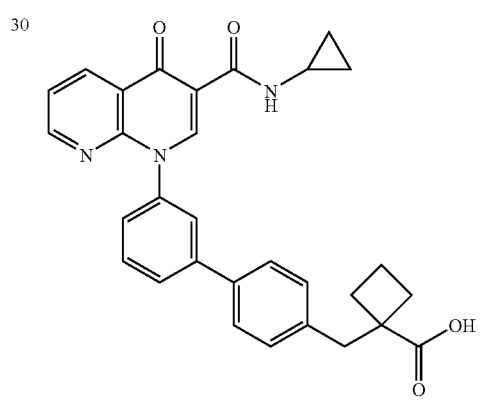
31 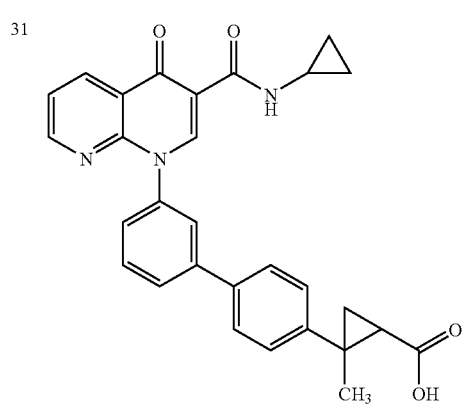
32 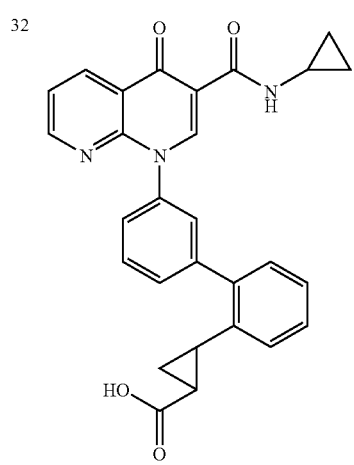
33 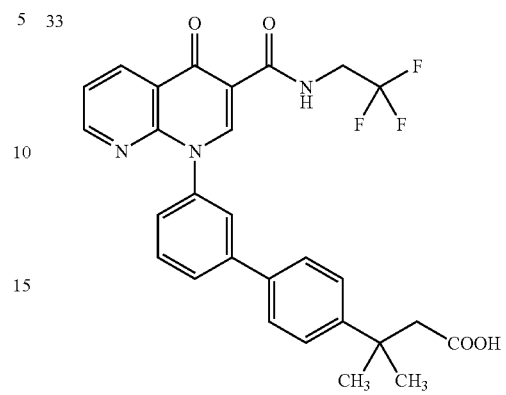
34 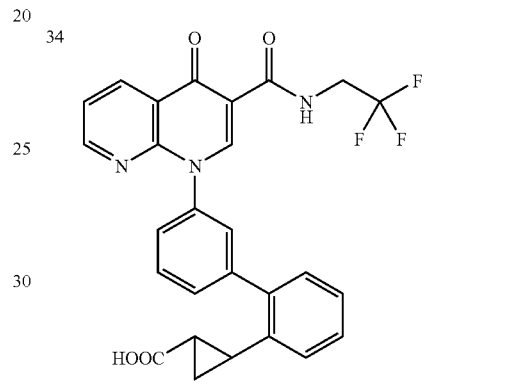
35 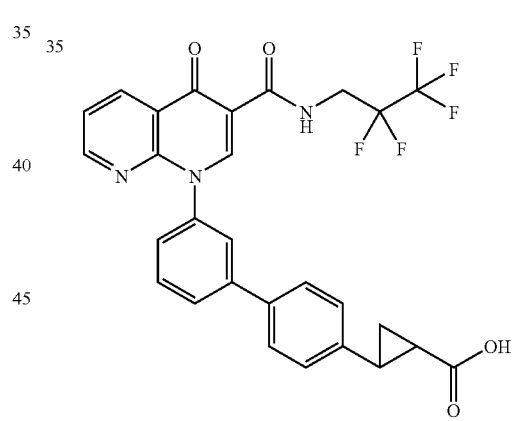
36 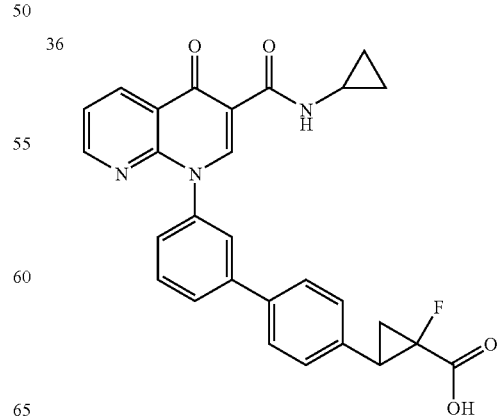

37
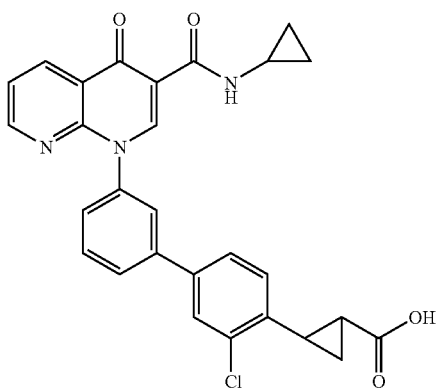
38
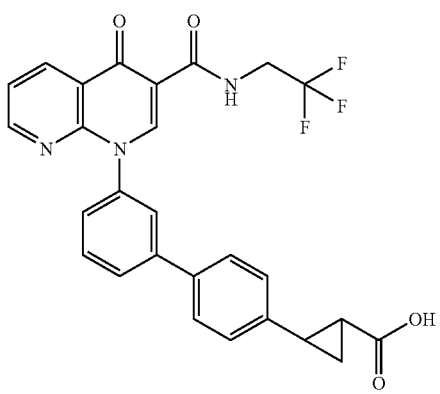
39
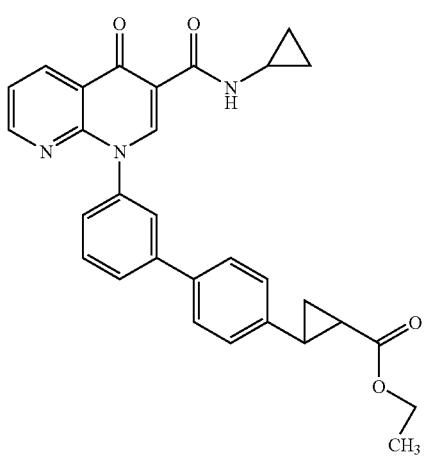
40
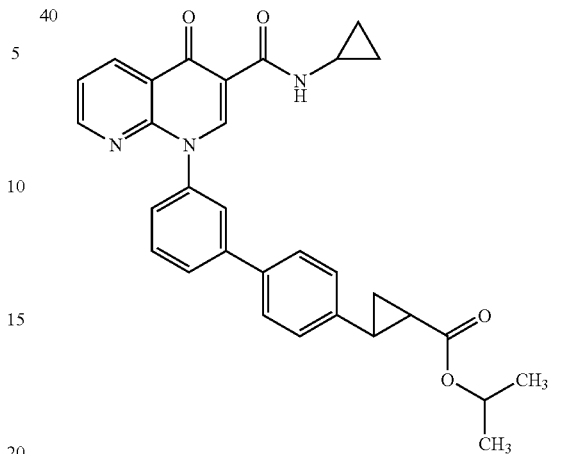
41
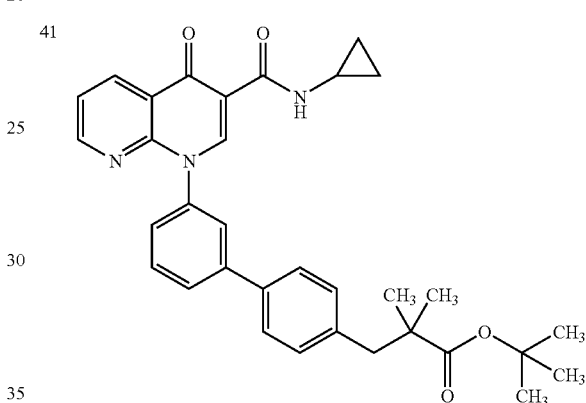
42
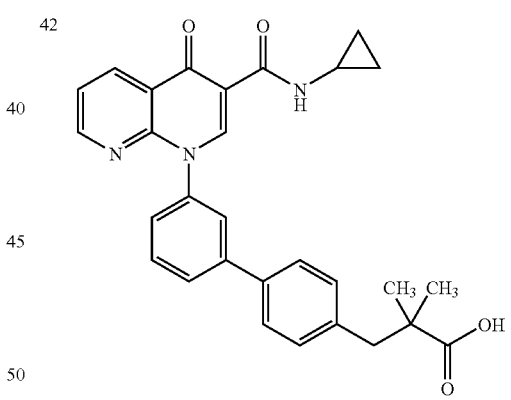
43
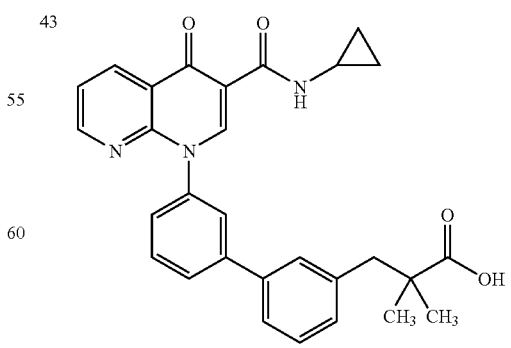

-continued
44 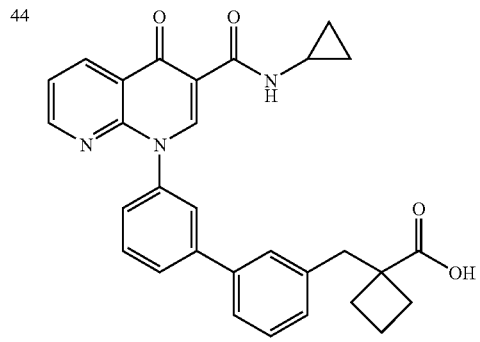
45 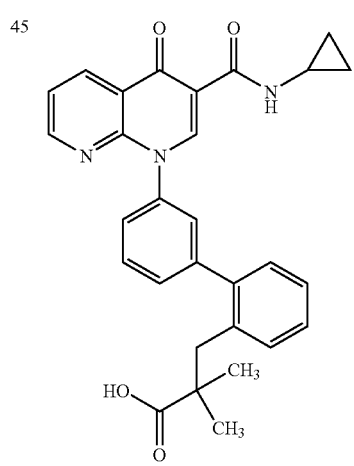
46 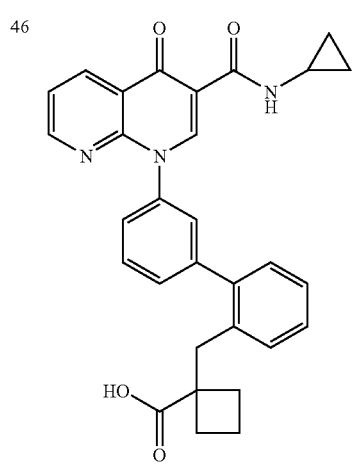
47 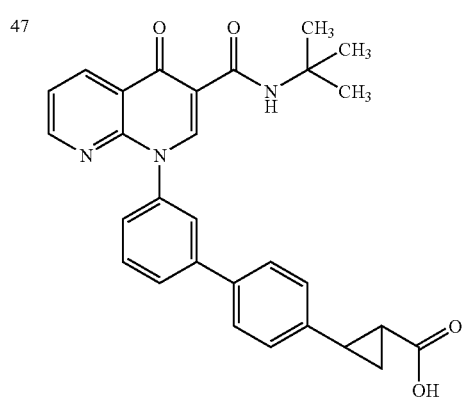
-continued
48 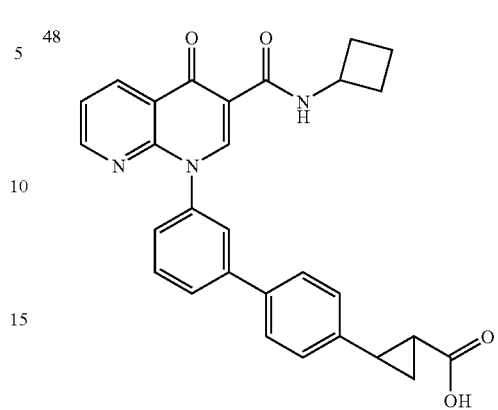
49 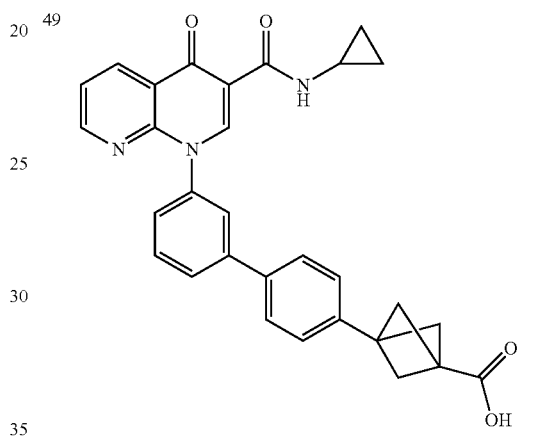
50 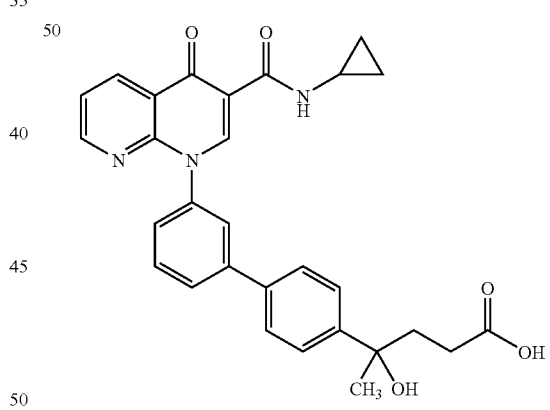
51 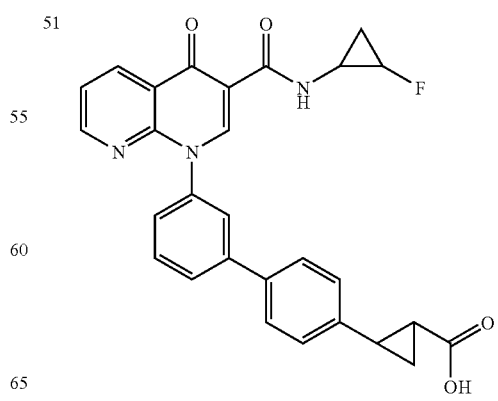

-continued
52
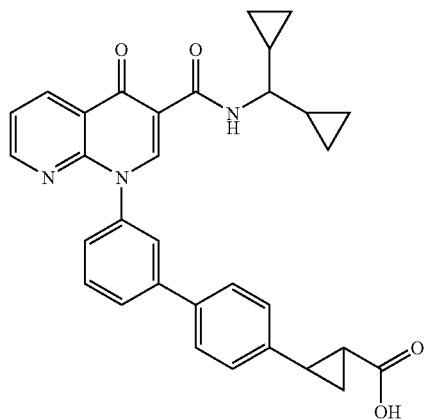
53
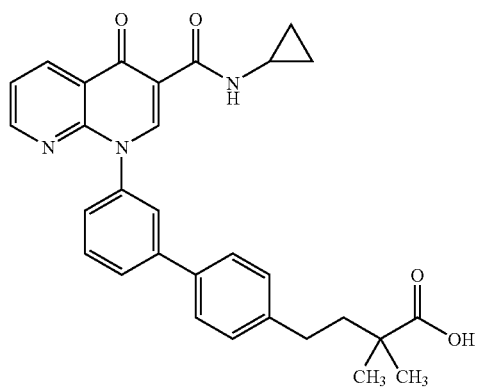
54
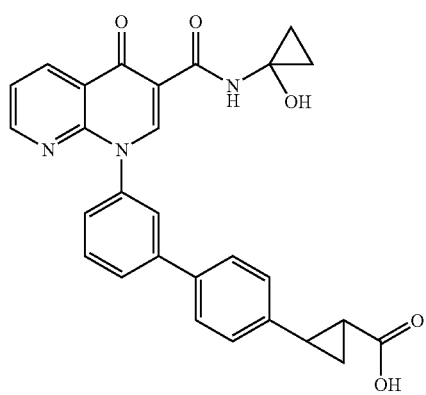
-continued
55
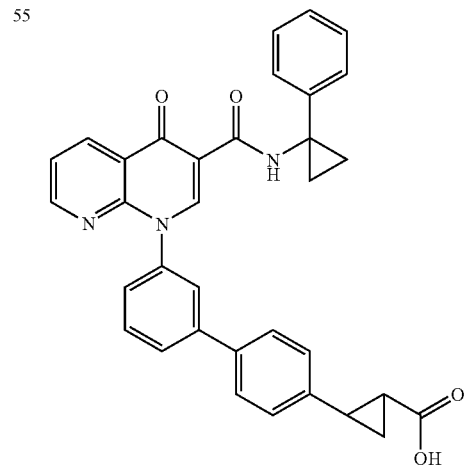
56
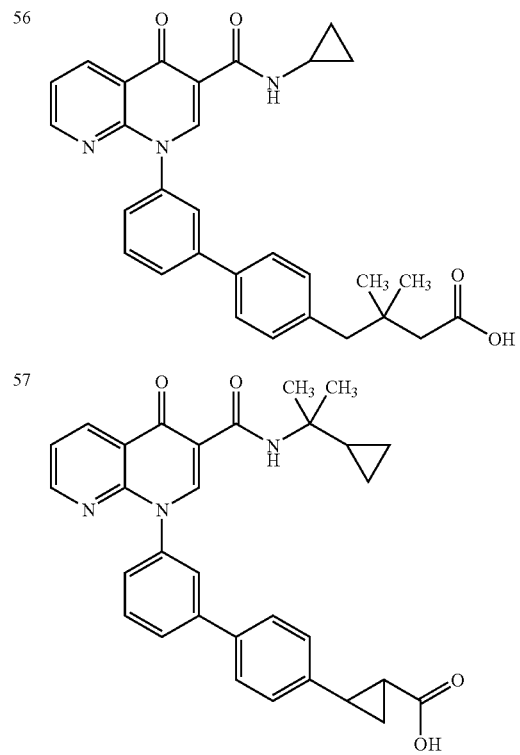
57
58
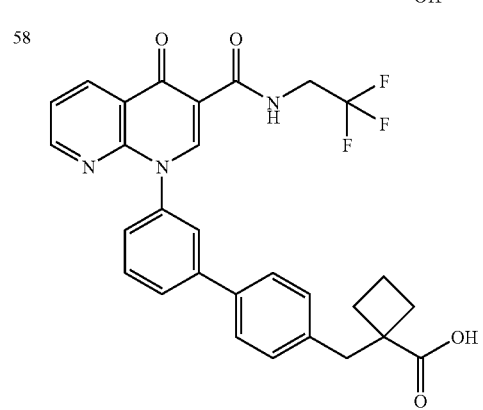

71
-continued
59
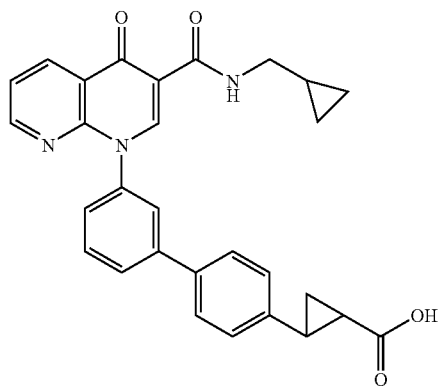
60
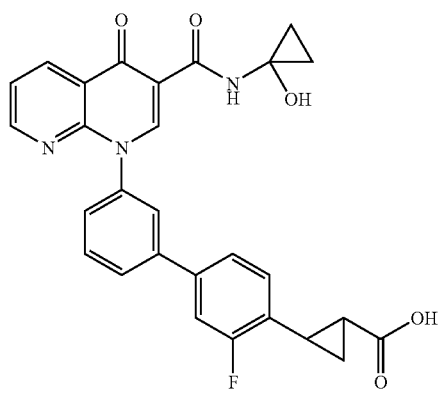
61
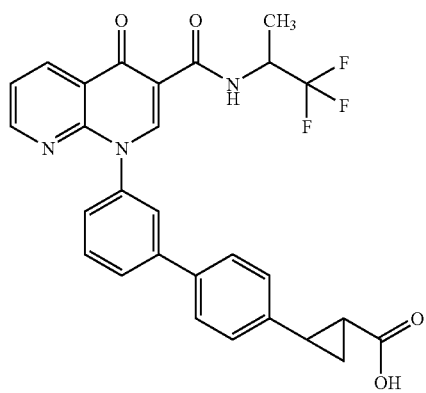
62
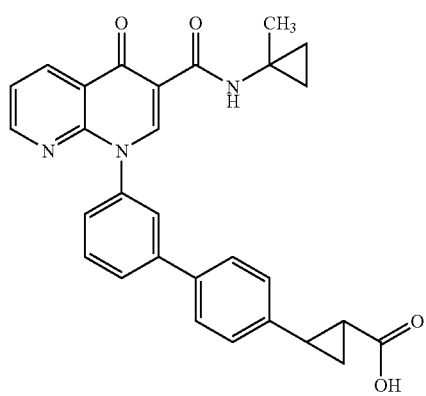
72
-continued
63
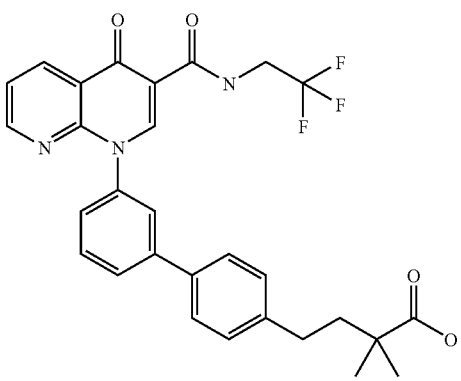
64
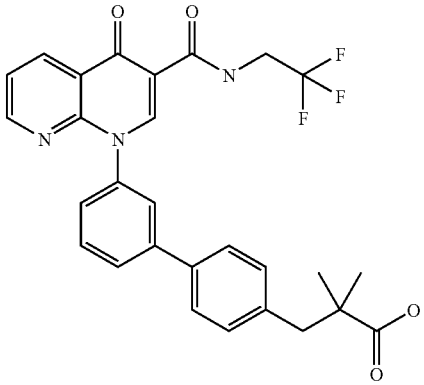
65
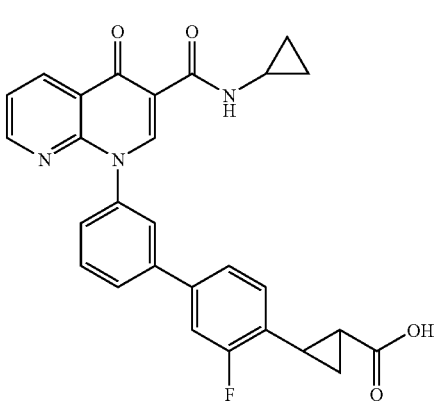
66
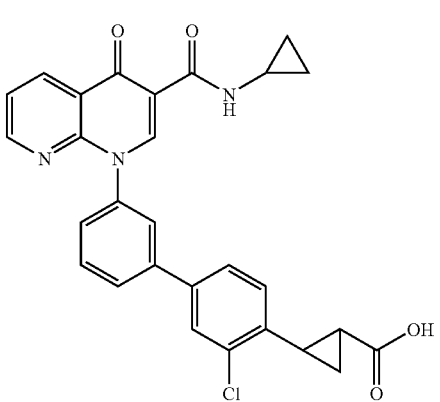

-continued

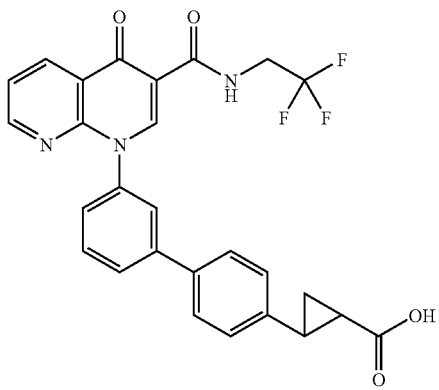

Other variations or modifications, which will be obvious to those skilled in the art, are within the scope and teachings of this invention. This invention is not to be limited except as set forth in the following claims.

What is claimed is:

1. A compound represented by Formula (I):

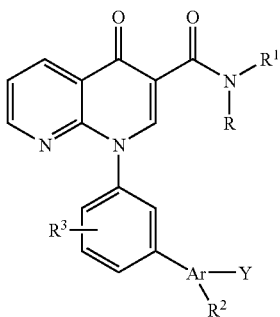

(I)

or a pharmaceutically acceptable salt thereof, wherein

Ar is phenyl, pyridyl, pyrimidyl, indolyl, quinolinyl, thienyl, pyridonyl, oxazolyl, oxadiazolyl, thiadiazolyl, or imidazolyl; or oxides thereof when Ar is a heteroaryl;

Y is —$C_{3-4}$cycloalkyl($C_{1-4}$alkyl)$_m$—COOH, wherein the $C_{3-4}$cycloalkyl is optionally substituted with halogen, alkoxy, hydroxy or nitrile, and the ($C_{1-4}$alkyl) substituents are optionally linked to form a $C_{3-4}$cycloalkyl; wherein n is 0, 1, 2, 3 or 4, m is 0, 1 or 2;

R is H or —$C_{1-6}$alkyl;

$R^1$ is H, or —$C_{1-6}$alkyl, —$C_{3-6}$cycloalkyl, —$C_{1-6}$alkoxy, —$C_{2-6}$alkenyl, —$C_{3-6}$alkynyl, heteroaryl, or heterocycle group, optionally substituted with 1–3 independent halo$C_{1-6}$alkyl, —$C_{1-6}$alkyl, —$C_{1-6}$alkoxy, OH, amino, —($C_{0-6}$alkyl)—$SO_p$—($C_{1-6}$alkyl), nitro, CN, =N—O—$C_{1-6}$alkyl, —O—N=$C_{1-6}$alkyl, or halogen substituents, wherein p is 0, 1 or 2;

$R^2$ is H, halogen, —CN, —$NO_2$, —$C_{1-6}$alkyl, —$C_{3-6}$cycloalkyl, —O—$C_{3-6}$cycloalkyl, O—$C_{1-6}$alkyl, O—$C_{3-6}$cycloalkyl—$C_{1-6}$alkyl($C_{3-6}$cycloalkyl)($C_{3-6}$cycloalkyl), —$C_{1-6}$alkoxy, phenyl, heteroaryl, heterocycle, amino, —C(O)—$C_{1-6}$alkyl, —C(O)—O—$C_{1-6}$alkyl, $C_{1-6}$alkoxy, phenyl, heteroaryl, heterocycle, amino, —C(O)—$C_{1-6}$alkyl, —C(O)—O—$C_{1-6}$alkyl, —$C_{1-6}$alkyl(=N—OH), —C(N=NOH)$C_{1-6}$alkyl, —$C_{0-6}$alkyl(oxy)$C_{1-6}$alkyl-phenyl, —$SO_k$NH($C_{0-6}$alkyl), or —($C_{0-6}$alkyl)—$SO_k$—($C_{1-6}$alkyl), wherein the phenyl, heteroaryl or heterocycle is optionally substituted with halogen, —$C_{1-6}$alkyl, $C_{1-6}$alkoxy, hydroxy, amino, or —C(O)—O—$C_{1-6}$alkyl, and wherein the alkyl or cycloalkyl is optionally substituted with 1–6 independently selected halogens or —OH, and wherein k is 0, 1, or 2;

$R^3$ is selected from H, halogen, CN, —$C_{1-6}$alkyl, —$C_{3-6}$cycloalkyl, nitro, —C(O)—$C_{1-6}$alkyl, —C(O)—O—$C_{0-6}$alkyl, —$SO_{n'}$NH($C_{0-6}$alkyl), or —($C_{0-6}$alkyl)—$SO_{n'}$—($C_{1-6}$alkyl), O—$C_{1-6}$alkyl, O—$C_{3-6}$cycloalkyl, wherein n' is 0, 1, or 2 and wherein the alkyl and cycloalkyl is optionally substituted with 1–6 independently selected halogen or OH.

2. A compound represented by Formula (I):

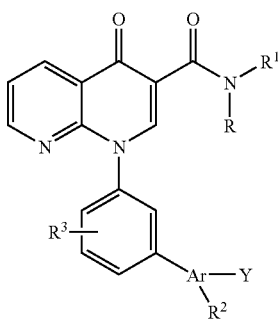

(I)

or a pharmaceutically acceptable salt thereof, wherein

Y is cyclopropyl-COOH;

Ar is phenyl,

R is H or —$C_{1-6}$alkyl;

$R^1$ is H, or —$C_{1-6}$alkyl, —$C_{3-6}$cycloalkyl, —$C_{1-6}$alkoxy, —$C_{2-6}$alkenyl, —$C_{3-6}$alkynyl, heteroaryl, or heterocycle group, optionally substituted with 1–3 independent halo$C_{1-6}$alkyl, —$C_{1-6}$alkyl, —$C_{1-6}$alkoxy, OH, amino, —($C_{0-6}$alkyl)—$SO_p$—($C_{1-6}$alkyl), nitro, CN, =N—O—$C_{1-6}$alkyl, —O—N=$C_{1-6}$alkyl, or halogen substituents, wherein p is 0, 1 or 2;

$R^2$ is H, halogen, —CN, —$NO_2$, —$C_{1-6}$alkyl, —$C_{3-6}$cycloalkyl, —O—$C_{3-6}$cycloalkyl, O—$C_{1-6}$alkyl, O—$C_{3-6}$cycloalkyl—$C_{1-6}$alkyl($C_{3-6}$cycloalkyl)($C_{3-6}$cycloalkyl), —$C_{1-6}$alkoxy, phenyl, heteroaryl, heterocycle, amino, —C(O)—$C_{1-6}$alkyl, —C(O)—O—$C_{1-6}$alkyl, —$C_{1-6}$alkyl(=N—OH), —C(N=NOH)$C_{1-6}$alkyl, —$C_{0-6}$alkyl(oxy)$C_{1-6}$alkyl-phenyl, —$SO_k$NH ($C_{0-6}$alkyl), or —($C_{0-6}$alkyl)—$SO_k$—($C_{1-6}$alkyl), wherein the phenyl, heteroaryl or heterocycle is optionally substituted with halogen, —$C_{1-6}$alkyl, —$C_{1-6}$alkoxy, hydroxy, amino, or —C(O)—O—$C_{1-6}$alkyl, and wherein the alkyl or cycloalkyl is optionally substituted with 1–6 independently selected halogens or —OH, and wherein k is 0, 1, or 2;

$R^3$ is selected from H, halogen, CN, —$C_{1-6}$alkyl, —$C_{3-6}$cycloalkyl, nitro, —C(O)—$C_{1-6}$alkyl, —C(O)—O—$C_{0-6}$alkyl, —$SO_{n'}$NH($C_{0-6}$alkyl), or —($C_{0-6}$alkyl)—$SO_{n'}$—($C_{1-6}$alkyl), O—$C_{1-6}$alkyl, O—$C_{3-6}$cycloalkyl, wherein n' is 0, 1, or 2 and wherein the alkyl and cycloalkyl is optionally substituted with 1–6 independently selected halogen or OH.

3. The compound according to claim 2, or a pharmaceutically acceptable salt thereof, wherein R[1] is —C$_{3-6}$cycloalkyl optionally substituted with 1–3 independent —C$_{1-6}$alkyl, —C$_{1-6}$alkoxy, OH, amino, —(C$_{0-6}$alkyl)—SO$_p$—(C$_{1-6}$alkyl), nitro, CN, =N—O—C$_{1-6}$alkyl, —O—N=C$_{1-6}$alkyl, or halogen substituents.

4. The compound according to claim 2, or a pharmaceutically acceptable salt thereof, wherein
R is hydrogen.

5. The compound according to claim 2, or a pharmaceutically acceptable salt thereof, wherein
R[2] is hydrogen or —C$_{1-3}$alkyl.

6. The compound according to claim 2, or a pharmaceutically acceptable salt thereof, wherein
R[1] is —C$_{3-6}$cycloalkyl optionally substituted with methyl or halo; and
R is hydrogen.

7. The compound according to claim 2, or a pharmaceutically acceptable salt thereof, wherein
R[1] is cyclopropyl optionally substituted with methyl or halo; and
R and R[2] are hydrogen.

8. A compound represented by Formula (I):

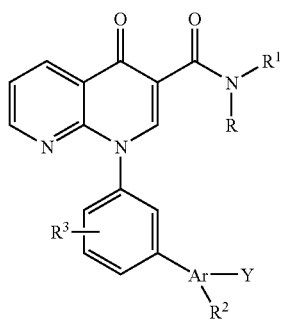

(I)

or a pharmaceutically acceptable salt thereof, wherein
R and R[3] are hydrogen;
R[1] is —C$_{3-6}$cycloalkyl optionally substituted with methyl or halo, or —C$_{1-3}$alkyl optionally substituted with 1–3 halo; and Ar is phenyl;
R[2] is hydrogen or halo; and
Y is —CH$_3$—C$_{3-4}$cycloalkyl —COOH or —C$_{3-4}$cycloalkyl —COOH.

9. A compound represented by Formula (I):

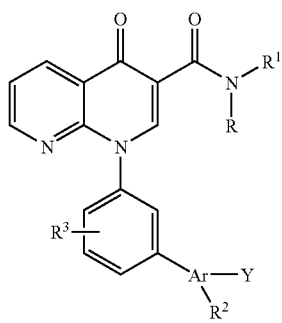

(I)

or a pharmaceutically acceptable salt thereof, wherein

Ar is phenyl, pyridyl, pyrimidyl, indolyl, quinolinyl, thienyl, pyridonyl, oxazolyl, oxadiazolyl, thiadiazolyl, or imidazolyl; or oxides thereof when Ar is a heteroaryl;
Y is —C$_{3-6}$cycloalkyl(C$_{1-4}$alkyl)$_m$—COOH, wherein the C$_{3-6}$cycloalkyl is optionally substituted with halogen, alkoxy, hydroxy or nitrile, and the (C$_{1-4}$alkyl) substituents are optionally linked to form a C$_{3-6}$cycloalkyl; wherein n is 0, 1, 2, 3 or 4, m is 0, 1;
R is H or —C$_{1-6}$alkyl;
R[1] is H, or —C$_{1-6}$alkyl, —C$_{3-6}$cycloalkyl, —C$_{1-6}$alkoxy, —C$_{2-6}$alkenyl, —C$_{3-6}$alkynyl, heteroaryl, or heterocycle group, optionally substituted with 1–3 independent haloC$_{1-6}$alkyl, —C$_{1-6}$alkyl, —C$_{1-6}$alkoxy, OH, amino, —(C$_{0-6}$alkyl)—SO$_p$—(C$_{1-6}$alkyl), nitro, CN, =N—O—C$_{1-6}$alkyl, —O—N=C$_{1-6}$alkyl, or halogen substituents, wherein p is 0, 1 or 2;
R[2] is H, halogen, —CN, —NO$^2$, —C$_{1-6}$alkyl, —C$_{3-6}$cycloalkyl, —O—C$_{3-6}$cycloalkyl, O—C$_{1-6}$alkyl, O—C$_{3-6}$cycloalkyl—C$_{1-6}$alkyl(C$_{3-6}$cycloalkyl)(C$_{3-6}$cycloalkyl), —C$_{1-6}$alkoxy, phenyl, heteroaryl, heterocycle, amino, —C(O)—C$_{1-6}$alkyl, —C(O)—O—C$_{1-6}$alkyl, —C$_{1-6}$alkyl(=N—OH), —C(N=NOH)C$_{1-6}$alkyl, —C$_{0-6}$alkyl(oxy)C$_{1-6}$alkyl-phenyl, —SO$_k$NH(C$_{0-6}$alkyl), or —(C$_{0-6}$alkyl)—SO$_k$—(C$_{1-6}$alkyl), wherein the phenyl, heteroaryl or heterocycle is optionally substituted with halogen, —C$_{1-6}$alkyl, —C$_{1-6}$alkoxy, hydroxy, amino, or —C(O)—O—C$_{1-6}$alkyl, and wherein the alkyl or cycloalkyl is optionally substituted with 1–6 independently selected halogens or —OH, and wherein k is 0, 1, or 2;
R[3] is selected from H, halogen, CN, —C$_{1-6}$alkyl, —C$_{3-6}$cycloalkyl, nitro, —C(O)—C$_{1-6}$alkyl, —C(O)—O—C$_{1-6}$alkyl, —SO$_{n'}$NH(C$_{0-6}$alkyl), or —(C$_{1-6}$alkyl)—SO$_{n'}$—(C$_{1-6}$alkyl), O—C$_{1-6}$alkyl, O—C$_{3-6}$cycloalkyl, wherein n' is 0, 1, or 2 and wherein the alkyl and cycloalkyl is optionally substituted with 1–6 independently selected halogen or OH.

10. A compound which is:

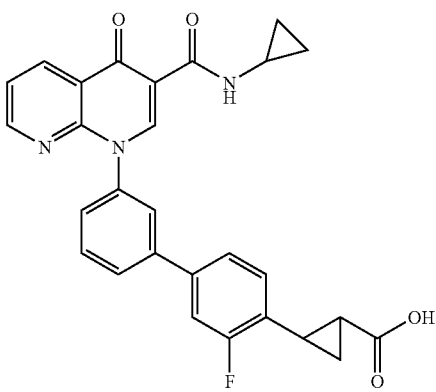

or a pharmaceutically acceptable salt thereof.

11. A pharmaceutical composition comprising
a therapeutically effective amount of the compound according to claim 10 or a pharmaceutically acceptable salt thereof; and a pharmaceutically acceptable carrier.

12. A compound which is
2-(trans)-{3'-[3-[(cyclopropylamino)carbonyl]-4-oxo-1,8-naphthyridin-1(4H)-y]-3-fluoro-1,1'-biphenyl-4-yl}cyclopropanecarboxylic acid;
or a pharmaceutically acceptable salt thereof.

13. A pharmaceutical composition comprising
a therapeutically effective amount of the compound according to claim 12 or a pharmaceutically acceptable salt thereof; and a pharmaceutically acceptable carrier.

14. A compound which is 2-(cis)-{3'-[3-[(cyclopropylamino)carbonyl]-4-oxo-1,8-naphthyridin-1(4H)-yl]-3-fluoro-1,1'-biphenyl-4-yl}cyclopropanecarboxylic acid; or a pharmaceutically acceptable salt thereof.

15. A pharmaceutical composition comprising
a therapeutically effective amount of the compound according to claim 14 or a pharmaceutically acceptable salt thereof; and a pharmaceutically acceptable carrier.

* * * * *